United States Patent
Do et al.

(10) Patent No.: US 10,463,352 B2
(45) Date of Patent: Nov. 5, 2019

(54) SYSTEMS AND METHODS FOR TISSUE CONTAINMENT AND RETRIEVAL

(71) Applicant: Applied Medical Resources Corporation, Rancho Santa Margarita, CA (US)

(72) Inventors: Alexandra Do, San Clemente, CA (US); Tracy Breslin, Rancho Santa Margarita, CA (US); Emily Yin, Anaheim, CA (US); Serene Wachli, Rancho Santa Margarita, CA (US); Charles C. Hart, Rancho Santa Margarita, CA (US); Jacob J. Filek, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 199 days.

(21) Appl. No.: 15/347,660

(22) Filed: Nov. 9, 2016

(65) Prior Publication Data
US 2017/0049427 A1  Feb. 23, 2017

Related U.S. Application Data

(63) Continuation of application No. PCT/US2015/045705, filed on Aug. 18, 2015.
(Continued)

(51) Int. Cl.
*A61B 17/00* (2006.01)
*A61B 17/34* (2006.01)
*A61B 17/02* (2006.01)

(52) U.S. Cl.
CPC .... *A61B 17/00234* (2013.01); *A61B 17/3423* (2013.01); *A61B 17/3431* (2013.01);
(Continued)

(58) Field of Classification Search
CPC ............ A61B 17/3423; A61B 17/3431; A61B 17/3439; A61B 2017/00287;
(Continued)

(56) References Cited

U.S. PATENT DOCUMENTS

| 1,550,403 A | 8/1925 | Turkus |
| 2,013,892 A | 9/1935 | Lucas |

(Continued)

FOREIGN PATENT DOCUMENTS

| DE | 4405831 A1 | 8/1995 |
| DE | 102013217513 A1 | 3/2015 |

(Continued)

OTHER PUBLICATIONS

European Patent Office, Invitation to Pay Additional Fees for International Application No. PCT/US2017/014402, titled "Systems and Methods for Tissue Removal", dated Apr. 6, 2017, 10pgs.
(Continued)

*Primary Examiner* — Martin T Ton
(74) *Attorney, Agent, or Firm* — Shirin Bozorgui

(57) ABSTRACT

Systems and methods for tissue containment and retrieval are disclosed. The containment system includes a primary chamber interconnected with a secondary channel extending from the primary chamber. A tissue specimen is mobilized inside a body cavity and placed into the primary chamber through a first opening. The first opening is pulled through a first incision or orifice and the narrower secondary channel is placed at a second incision or orifice. A second opening at the end of the secondary channel permits observation via a scope inserted through the second opening of the tissue specimen in the primary chamber undergoing morcellation via the first opening. Other systems and methods for deployment, containment, debulking and sealing of the second opening to create a closed system for the safe retrieval of the tissue specimen are provided.

20 Claims, 30 Drawing Sheets

Related U.S. Application Data

(60) Provisional application No. 62/038,740, filed on Aug. 18, 2014.

(52) U.S. Cl.
CPC . *A61B 17/3439* (2013.01); *A61B 2017/00287* (2013.01); *A61B 2017/0225* (2013.01); *A61B 2017/3433* (2013.01)

(58) Field of Classification Search
CPC .... A61B 2017/0225; A61B 2017/3433; A61B 2017/3425; A61B 2017/3427; A61B 2017/3429
USPC ........................................................ 606/114
See application file for complete search history.

(56) References Cited

U.S. PATENT DOCUMENTS

| | | | |
|---|---|---|---|
| 2,812,758 | A | 11/1957 | Blumenschein |
| 3,244,169 | A | 4/1966 | Baxter |
| 3,762,417 | A | 10/1973 | Textor |
| 3,807,393 | A | 4/1974 | McDonald |
| 4,120,301 | A | 10/1978 | Lovick |
| 4,553,537 | A | 11/1985 | Rosenberg |
| 4,573,452 | A | 3/1986 | Greenberg |
| 5,037,379 | A | 8/1991 | Clayman et al. |
| 5,143,082 | A | 9/1992 | Kindberg et al. |
| 5,213,114 | A | 5/1993 | Bailey, Jr. |
| 5,215,521 | A | 5/1993 | Cochran et al. |
| 5,215,101 | A | 6/1993 | Jacobs et al. |
| 5,224,930 | A | 7/1993 | Spaeth et al. |
| 5,231,974 | A | 8/1993 | Giglio et al. |
| 5,308,327 | A | 5/1994 | Heaven et al. |
| 5,312,416 | A | 5/1994 | Spaeth et al. |
| 5,320,627 | A | 6/1994 | Sorensen et al. |
| 5,330,483 | A | 7/1994 | Heaven et al. |
| 5,337,754 | A | 8/1994 | Heaven et al. |
| 5,354,303 | A | 10/1994 | Spaeth et al. |
| 5,368,545 | A | 11/1994 | Schaller et al. |
| 5,465,731 | A | 11/1995 | Bell et al. |
| 5,486,183 | A | 1/1996 | Middleman et al. |
| RE35,164 | E | 3/1996 | Kindberg et al. |
| 5,520,610 | A | 5/1996 | Giglio et al. |
| 5,611,803 | A | 3/1997 | Heaven et al. |
| 5,618,296 | A | 4/1997 | Sorenson et al. |
| 5,636,639 | A | 6/1997 | Turturro et al. |
| 5,647,372 | A | 7/1997 | Tovey et al. |
| 5,649,550 | A | 7/1997 | Crook |
| 5,669,927 | A | 9/1997 | Boebel et al. |
| 5,769,794 | A | 6/1998 | Conlan et al. |
| 5,785,677 | A * | 7/1998 | Auweiler ......... A61B 17/00234 128/850 |
| 5,788,709 | A | 8/1998 | Riek et al. |
| 5,810,721 | A | 9/1998 | Mueller et al. |
| 5,836,936 | A | 11/1998 | Cuschieri |
| 5,895,392 | A | 4/1999 | Riek et al. |
| 5,957,884 | A | 9/1999 | Hooven |
| 5,971,995 | A | 10/1999 | Rousseau |
| 6,036,681 | A | 3/2000 | Hooven |
| 6,039,748 | A | 3/2000 | Savage et al. |
| 6,045,566 | A | 4/2000 | Pagedas |
| 6,048,309 | A | 4/2000 | Flom et al. |
| 6,059,793 | A | 5/2000 | Pagedas |
| 6,142,935 | A | 11/2000 | Flom et al. |
| 6,162,172 | A | 12/2000 | Cosgrove et al. |
| 6,206,889 | B1 | 3/2001 | Bernardo |
| 6,228,095 | B1 | 5/2001 | Dennis |
| 6,254,534 | B1 | 7/2001 | Butler et al. |
| 6,258,102 | B1 | 7/2001 | Pagedas |
| 6,270,505 | B1 | 8/2001 | Yoshida et al. |
| 6,350,267 | B1 | 2/2002 | Stefanchik |
| 6,382,211 | B1 | 5/2002 | Crook |
| 6,387,102 | B2 | 5/2002 | Pagedas |
| 6,406,440 | B1 | 6/2002 | Stefanchik |
| 6,569,105 | B1 | 5/2003 | Kortenbach et al. |
| 6,685,628 | B2 | 2/2004 | Vu |
| 6,814,700 | B1 | 11/2004 | Mueller et al. |
| 6,958,037 | B2 | 10/2005 | Ewers et al. |
| 7,041,055 | B2 | 5/2006 | Young et al. |
| 7,238,154 | B2 | 7/2007 | Ewers et al. |
| 7,297,106 | B2 | 11/2007 | Yamada et al. |
| 7,377,898 | B2 | 5/2008 | Ewers et al. |
| 7,491,168 | B2 | 2/2009 | Raymond et al. |
| 7,537,564 | B2 | 5/2009 | Bonadio et al. |
| 7,547,310 | B2 | 6/2009 | Whitfield |
| 7,670,346 | B2 | 3/2010 | Whitfield |
| 7,758,500 | B2 | 7/2010 | Boyd et al. |
| 7,758,501 | B2 | 7/2010 | Frasier et al. |
| 7,762,969 | B2 | 7/2010 | Bilsbury |
| 7,896,877 | B2 | 3/2011 | Hall et al. |
| 7,955,292 | B2 | 6/2011 | Leroy et al. |
| 7,981,130 | B2 | 7/2011 | Seeh |
| 7,998,068 | B2 | 8/2011 | Bonadio et al. |
| 8,016,771 | B2 | 9/2011 | Orban, III |
| 8,016,839 | B2 | 9/2011 | Wilk |
| 8,038,611 | B2 | 10/2011 | Raymond et al. |
| 8,075,567 | B2 | 12/2011 | Taylor et al. |
| 8,100,928 | B2 | 1/2012 | Nohilly et al. |
| 8,114,119 | B2 | 2/2012 | Spivey et al. |
| 8,152,820 | B2 | 4/2012 | Mohamed et al. |
| 8,157,834 | B2 | 4/2012 | Conlon |
| 8,337,510 | B2 | 12/2012 | Rieber et al. |
| 8,366,754 | B2 | 2/2013 | Teague et al. |
| 8,409,112 | B2 | 4/2013 | Wynne et al. |
| 8,409,216 | B2 | 4/2013 | Parihar et al. |
| 8,414,596 | B2 | 4/2013 | Parihar et al. |
| 8,425,533 | B2 | 4/2013 | Parihar et al. |
| 8,517,935 | B2 | 8/2013 | Marchek et al. |
| 8,579,914 | B2 | 11/2013 | Menn et al. |
| 8,597,180 | B2 | 12/2013 | Copeland et al. |
| 8,622,897 | B2 | 1/2014 | Raymond et al. |
| 8,721,538 | B2 | 5/2014 | Bucholz |
| 8,721,658 | B2 | 5/2014 | Kahle et al. |
| 8,734,336 | B2 | 5/2014 | Bonadio et al. |
| 8,777,849 | B2 | 7/2014 | Haig et al. |
| 8,821,377 | B2 | 9/2014 | Collins |
| 8,857,440 | B2 | 10/2014 | Gundlapalli et al. |
| 8,864,658 | B2 | 10/2014 | Wilkins et al. |
| 8,920,431 | B2 | 12/2014 | Shibley et al. |
| 8,956,286 | B2 | 2/2015 | Shibley et al. |
| 8,961,408 | B2 | 2/2015 | Wilkins et al. |
| 8,961,409 | B2 | 2/2015 | O'Prey et al. |
| 9,039,610 | B2 | 5/2015 | Wilkins et al. |
| 9,044,210 | B1 | 6/2015 | Hoyte et al. |
| 9,168,031 | B2 | 10/2015 | Copeland et al. |
| 2004/0097960 | A1 | 5/2004 | Terachi et al. |
| 2004/0158261 | A1 | 8/2004 | Vu |
| 2005/0171405 | A1 | 8/2005 | Rowland et al. |
| 2005/0267492 | A1 | 12/2005 | Poncet et al. |
| 2006/0200169 | A1 | 9/2006 | Sniffin |
| 2006/0200170 | A1 | 9/2006 | Aranyi |
| 2007/0051375 | A1 | 3/2007 | Milliman |
| 2007/0135780 | A1 | 6/2007 | Pagedas |
| 2007/0161866 | A1 | 7/2007 | Fowler, Jr. et al. |
| 2007/0161867 | A1 | 7/2007 | Fowler, Jr. et al. |
| 2009/0138024 | A1 | 5/2009 | Ichihara et al. |
| 2009/0264710 | A1 | 10/2009 | Chana et al. |
| 2010/0219091 | A1 | 9/2010 | Turner |
| 2011/0054260 | A1 | 3/2011 | Albrecht et al. |
| 2011/0184311 | A1 | 7/2011 | Parihar et al. |
| 2011/0184435 | A1 | 7/2011 | Parihar et al. |
| 2011/0190779 | A1 | 8/2011 | Gell et al. |
| 2011/0319719 | A1 | 12/2011 | O'Prey et al. |
| 2012/0078264 | A1 | 3/2012 | Taylor et al. |
| 2012/0083795 | A1 | 4/2012 | Fleming et al. |
| 2012/0109144 | A1 | 5/2012 | Chin et al. |
| 2012/0157777 | A1 | 6/2012 | Okoniewski |
| 2012/0238823 | A1 | 9/2012 | Hagerty et al. |
| 2012/0316572 | A1 | 12/2012 | Rosenblatt et al. |
| 2013/0103042 | A1 | 4/2013 | Davis |
| 2013/0103043 | A1 | 4/2013 | Cabrera |

(56) References Cited

U.S. PATENT DOCUMENTS

| | | | |
|---|---|---|---|
| 2013/0131457 A1 | 5/2013 | Seckin | |
| 2013/0138115 A1 | 5/2013 | Seckin | |
| 2013/0184536 A1 | 7/2013 | Shibley et al. | |
| 2013/0284186 A1 | 10/2013 | Touati | |
| 2014/0052018 A1 | 2/2014 | Hawkins | |
| 2014/0058210 A1 | 2/2014 | Raymond et al. | |
| 2014/0058403 A1 | 2/2014 | Menn et al. | |
| 2014/0135788 A1 | 5/2014 | Collins | |
| 2014/0235952 A1 | 8/2014 | Haig et al. | |
| 2014/0236110 A1 | 8/2014 | Taylor et al. | |
| 2014/0296649 A1 | 10/2014 | Fehling et al. | |
| 2014/0316210 A1 | 10/2014 | Koehler et al. | |
| 2014/0330285 A1 | 11/2014 | Rosenblatt et al. | |
| 2015/0005584 A1 | 1/2015 | Wilkins et al. | |
| 2015/0018625 A1 | 1/2015 | Miraki et al. | |
| 2015/0094541 A1 | 4/2015 | Wilkins et al. | |
| 2015/0119647 A1 | 4/2015 | Vaillancourt et al. | |
| 2015/0305728 A1* | 10/2015 | Taylor | A61B 17/00234 606/114 |
| 2015/0320409 A1* | 11/2015 | Lehmann | A61B 17/221 600/109 |
| 2016/0135798 A1* | 5/2016 | Macleod | A61B 17/00234 606/114 |
| 2016/0302783 A1* | 10/2016 | Greenberg | A61B 17/00234 |

FOREIGN PATENT DOCUMENTS

| | | |
|---|---|---|
| EP | 1 312 318 A1 | 5/2003 |
| EP | 1 935 356 A1 | 10/2004 |
| EP | 2 138 113 A2 | 12/2009 |
| EP | 2 359 758 A2 | 8/2011 |
| EP | 2 668 907 A2 | 12/2013 |
| WO | WO 00/32116 | 6/2000 |
| WO | WO 03/061480 A1 | 7/2003 |
| WO | WO 03/071926 A2 | 9/2003 |
| WO | WO 2004/075730 A2 | 9/2004 |
| WO | WO 2008/083222 A2 | 7/2008 |
| WO | WO 2011/143410 A1 | 11/2011 |
| WO | WO 2013/093030 A2 | 6/2013 |
| WO | WO 2013/150391 A1 | 10/2013 |
| WO | WO 2015/164591 A1 | 10/2015 |

OTHER PUBLICATIONS

The International Bureau of WIPO, International Preliminary Report on Patentability for International Application No. PCT/US2017/014402, entitled "Systems and Methods for Tissue Removal," dated Aug. 2, 2018, 11pgs.

European Patent Office, The International Search Report and Written Opinion for International Application No. PCT/US2017/014402, entitled "Systems and Methods for Tissue Removal," dated Jun. 6, 2017, 20 pgs.

European Patent Office, The International Search Report and Written Opinion for International Application No. PCT/US2015/045705, dated Apr. 18, 2016, entitled "Systems and Methods for Tissue Containment and Retrieval."

European Patent Office, The International Search Report and Written Opinion for International Application No. PCT/US2015/056978, entitled "Systems and Methods for Tissue Removal," dated Jan. 15, 2016.

European Patent Office, The International Search Report and Written Opinion for International Application No. PCT/US2015/027274, entitled "Suture Clinch with Traction Enhanced," dated Jul. 10, 2015.

European Patent Office, The International Search Report and Written Opinion for International Application No. PCT/US2016/029154, entitled "Systems and Methods for Tissue Removal," dated Aug. 19, 2016, 17 pgs.

The International Bureau of WIPO, International Preliminary Report on Patentability for International Application No. PCT/US2015/027274, entitled "Systems and Methods for Tissue Removal," dated Nov. 3, 2016, 9 pgs.

The International Bureau of WIPO, International Preliminary Report on Patentability for International Application No. PCT/US2015/045705, entitled "Systems and Methods for Tissue Containment and Retrieval," dated Mar. 2, 2017, 10 pgs.

The International Bureau of WIPO, International Preliminary Report on Patentability for International Application No. PCT/US2015/056978, entitled "Systems and Methods for Tissue Removal," dated May 26, 2017, 10 pgs.

The International Bureau of WIPO, International Preliminary Report on Patentability for International Application No. PCT/US2016/029154, entitled "Systems and Methods for Tissue Removal," dated Nov. 2, 2017, 11pgs.

* cited by examiner

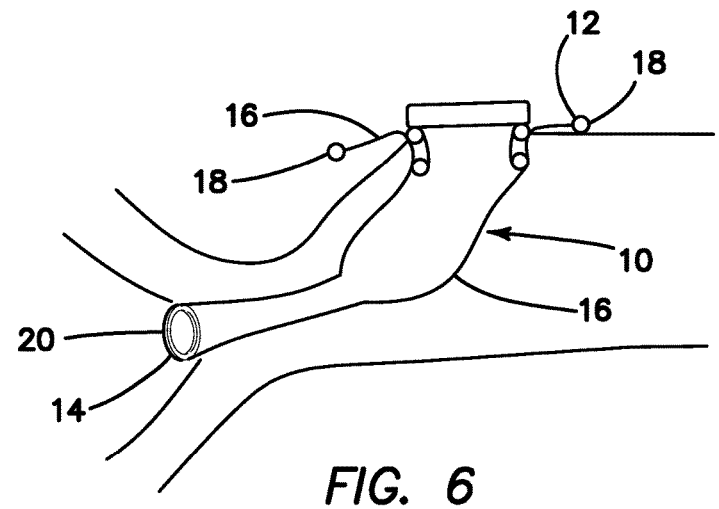
FIG. 6
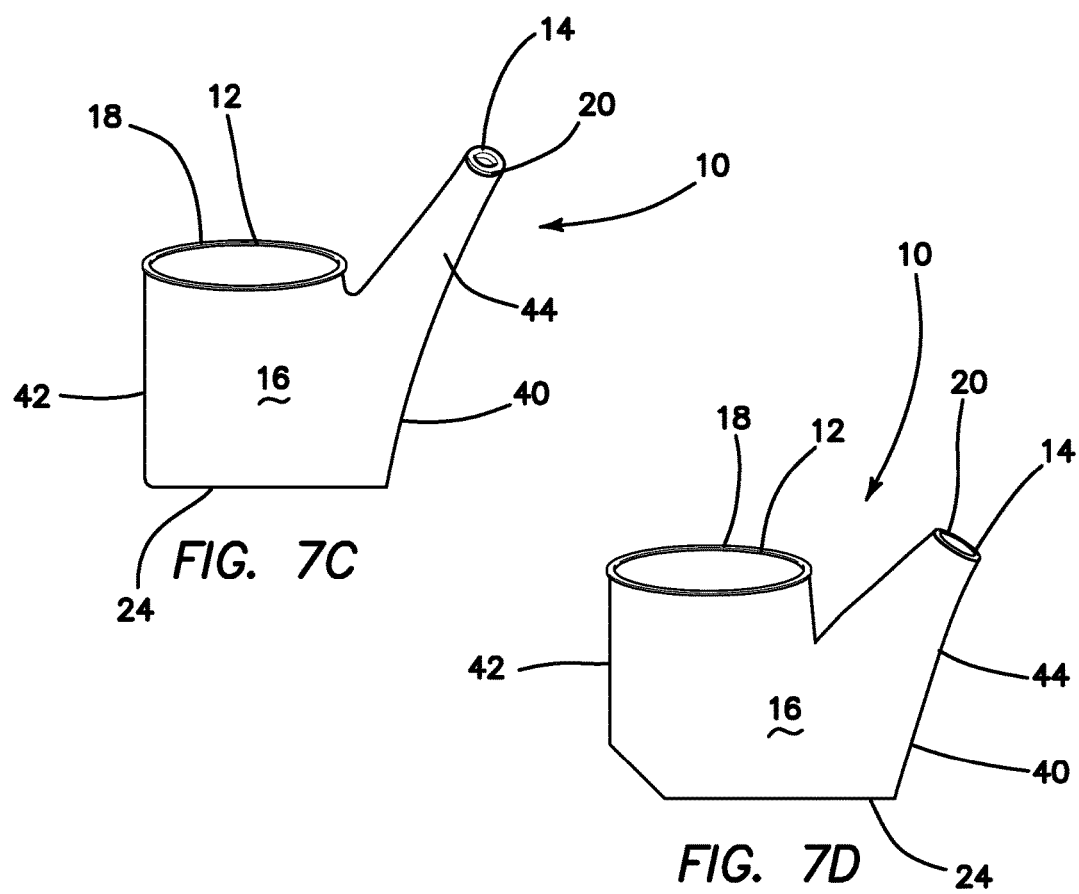
FIG. 7C
FIG. 7D

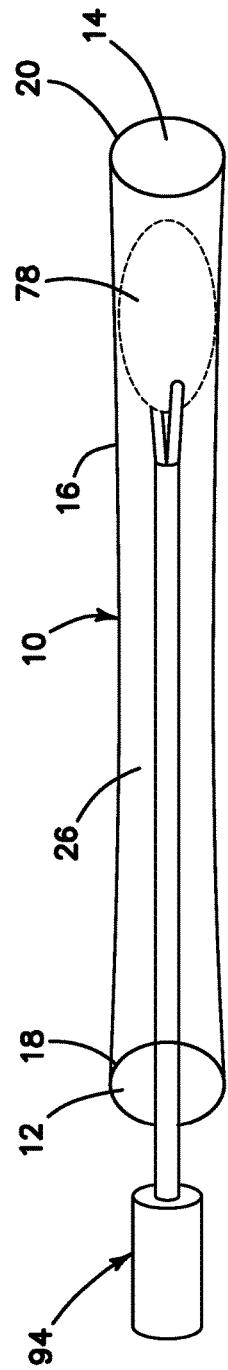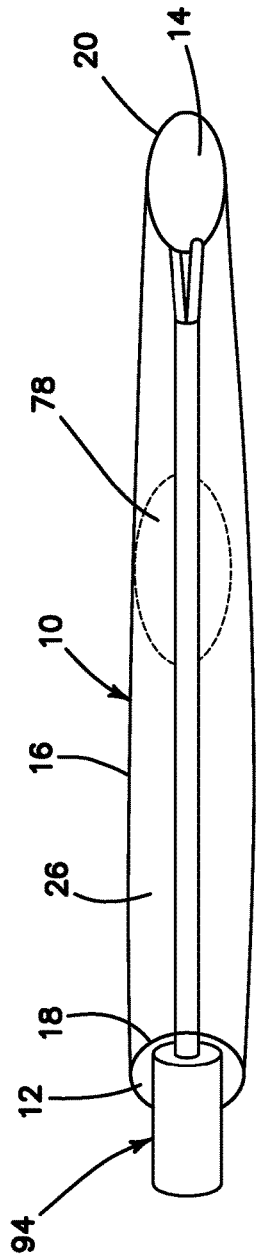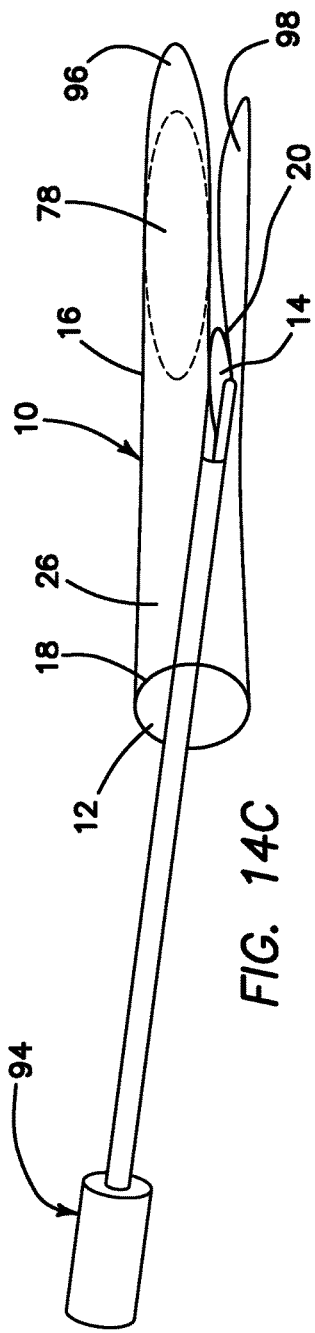

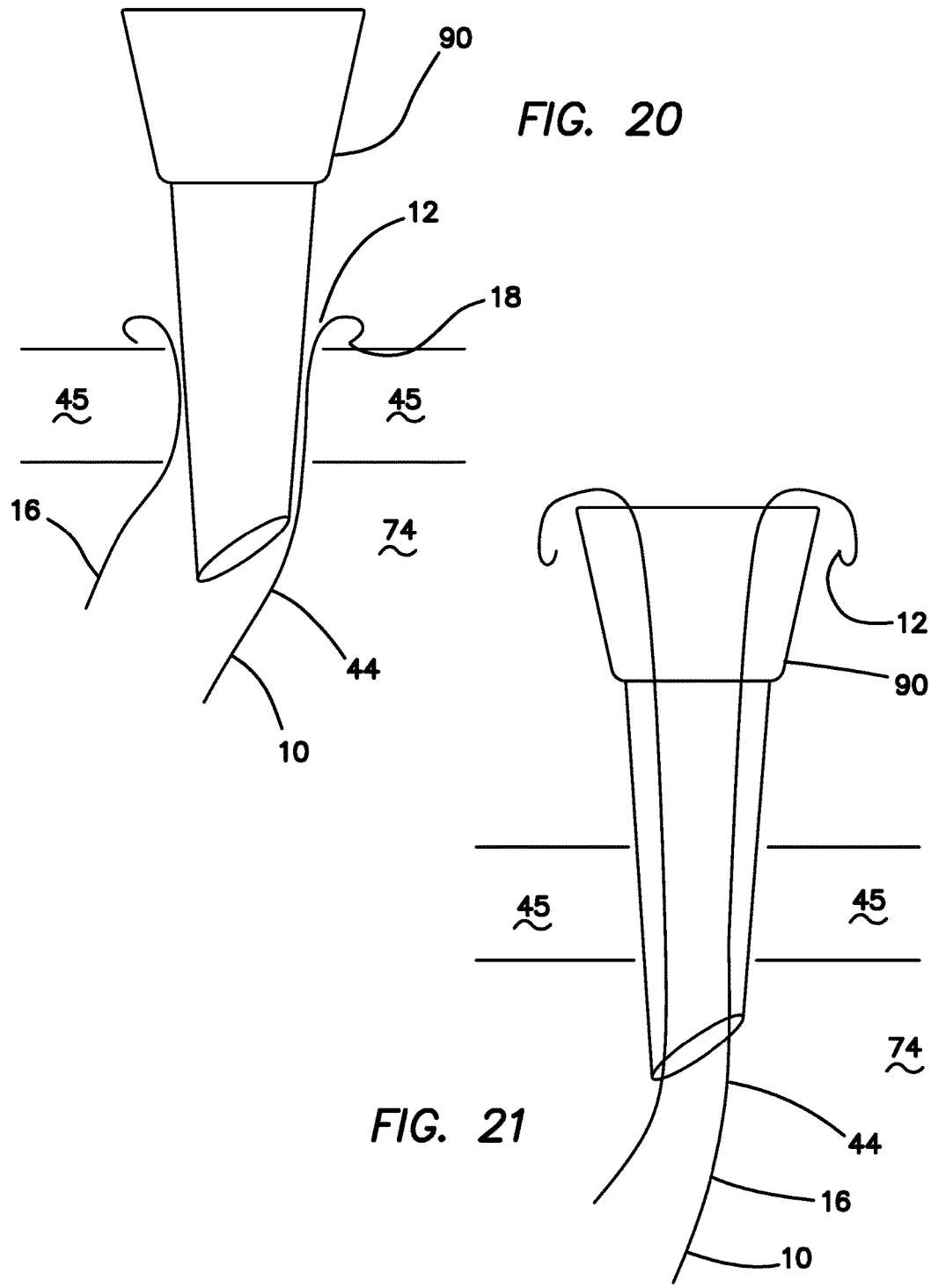

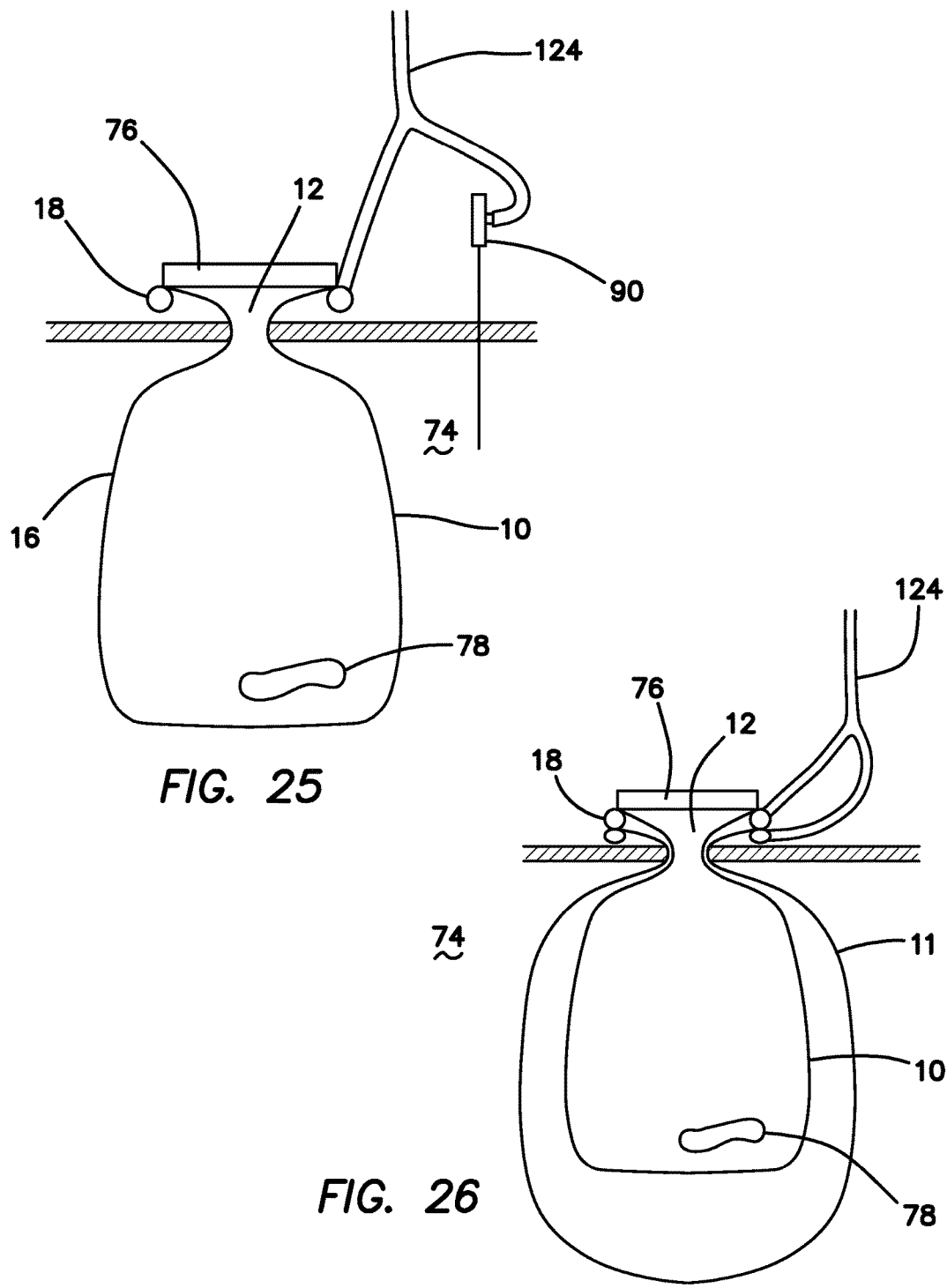

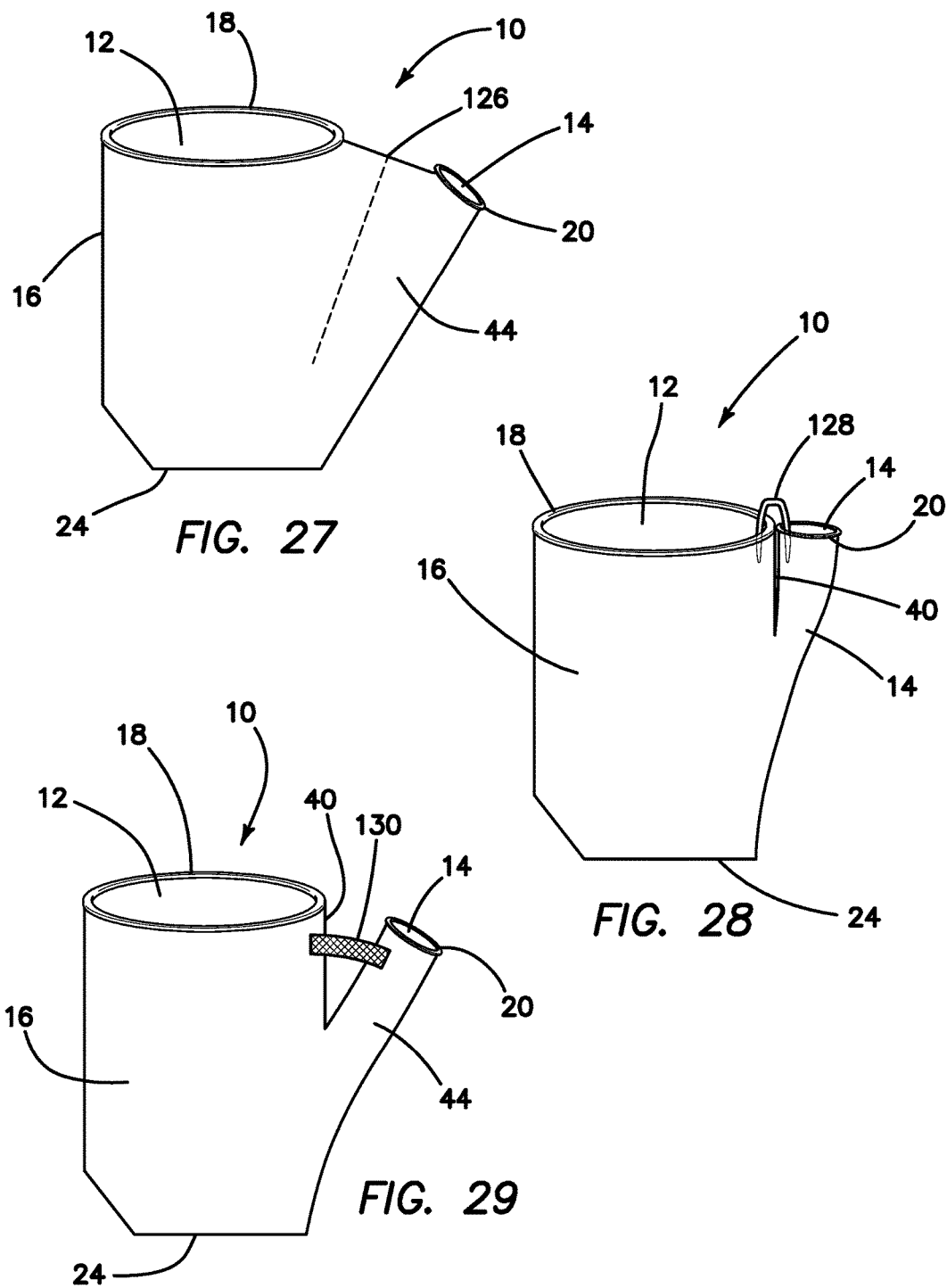

SYSTEMS AND METHODS FOR TISSUE CONTAINMENT AND RETRIEVAL

CROSS-REFERENCE TO RELATED APPLICATIONS

This application is a continuation of International Application No. PCT/US2015/045705 filed on Aug. 18, 2015 entitled "Systems and methods for tissue containment and retrieval" which claims priority to and benefit of U.S. Provisional Patent Application Ser. No. 62/038,740 filed on Aug. 18, 2014 entitled "Power morcellation system" all of which are incorporated herein by reference in their entirety.

FIELD OF THE INVENTION

This application relates to medical devices, in particular, systems and methods for the surgical removal of tissue through small incision sites and/or body orifices including specimen containment bags are described.

BACKGROUND OF THE INVENTION

Where needed, a small incision is made in a patient to access surgically targeted tissue located inside a body cavity. Surgically targeted tissue may also be approached through a body orifice without an initial incision. Sometimes the targeted tissue is approached directly through the incision or body orifice. Other times, an access device system is placed and/or positioned into, across, at, and/or within the incision and/or body orifice to retract tissue, enlarge, reshape, and/or isolate the incision or body orifice. The access device system serves as a portal for accessing targeted tissue that is located in or adjacent to the body cavity or body orifice. The targeted tissue is detached from adjacent and surrounding tissue employing known surgical techniques and procedures. Once freed, the targeted tissue is ready for removal through the small incision or body orifice. If the targeted tissue is too large to be removed in whole, then it is reduced in size and removed in parts through the small incision. Ideally, the surgeon will "core" or "peel" the targeted tissue to keep it in one piece as much as possible. However, more likely than not, the targeted tissue will be reduced into multiple pieces.

Reducing the size of the targeted tissue is called morcellation. A morcellation procedure includes cutting the targeted tissue into smaller pieces manually with a scalpel or knife, for example, or employing a power morcellator to cut the targeted tissue so that it is removable through the small incision. Pieces of the targeted tissue are removed from the patient through the small incision. As the targeted tissue is being reduced in size in order to fit through the small incision, small pieces of tissue may be cut off and left behind in the patient. As such, morcellation is contraindicated in cases of malignancy or endometriosis. If cancer is morcellated, it can spread malignant tissue and upstage cancer and increase patient mortality.

A hysterectomy is an example of a surgical procedure that may involve morcellation. More than 500,000 hysterectomies are performed annually on women in the United States. Common reasons that a woman may have a hysterectomy are the presence of fibroids, cancer, endometriosis or prolapse. Of these hysterectomies, about 200,000 are performed laparoscopically. When the uterus is too large (>300 g) to be removed through the vagina or if the cervix is still in place, the specimen must be reduced in size to be removed through an abdominal incision or through the vagina. During myomectomy (fibroid removal), large fibroids may also need to be extracted using a morcellation procedure. During morcellation, the targeted tissue (usually a uterus and sometimes adnexal structures) is brought to the abdominal wall surface within the pelvic cavity such as with a tissue grasper and is reduced in size using a blade and removed through the incision from the pelvic cavity. In another variation, the targeted tissue is removed through a body orifice such as through the vagina. Fibroids, or uterine leiomyoma, account for about 30-40% of hysterectomies. These are benign tumors of the uterus that can lead to heavy and painful bleeding. In the past there has been a mild concern that these tumors could be undetected cancer, or Leiomyosarcoma, and it was believed to affect about 1 in 10,000 women. More recent data has come out to support a much higher risk of undetected malignancy in these tumors, putting the range at 1:1000 to 1:400. Because of this elevated risk, many surgeons have begun changing their technique to try to enclose the specimen to do a closed morcellation process by morcellating in a bag to contain errant pieces, rather than morcellating without a bag in a process called open morcellation. Many GYN societies, including the American Association of Gynecologic Laparoscopists (AAGL), the American Congress of Obstetricians and Gynecologists (ACOG), and the Society of Gynecologic Oncology (SGO), have released statements warning of the potential danger of open morcellation. On Apr. 17, 2014, the FDA issued a statement discouraging the use of open power morcellation for hysterectomies and myomectomies for women undergoing these procedures for fibroids. The FDA also increased their estimated of malignant likelihood to 1 in 350. For these reasons, systems and methods are needed to safely and effectively reduce tissue specimens. The present invention sets forth such safe systems and methods for both manual morcellation and power morcellation performed in closed system.

SUMMARY OF THE INVENTION

According to one aspect of the invention a tissue containment bag is provided. The tissue containment bag includes a first opening and a second opening interconnected by a sidewall of flexible material. The sidewall defines a first interior compartment and a base configured for receiving a tissue specimen through the first opening into the first interior compartment and supporting the tissue specimen on the base. The sidewall forms an elongated hollow, sleeve-like neck extension defining a second interior compartment having a proximal end interconnected with the first interior compartment and a distal end interconnected with the second opening. The second opening is in fluidic communication with the second interior compartment. The second interior compartment is in fluidic communication with the first interior compartment and the first interior compartment is in fluidic communication with the first opening. The proximal end of the neck extension is connected to the sidewall of the first interior compartment at a first side. The neck extension extends laterally in a direction away from a first longitudinal axis defined by the radial plane of the first opening when the bag is in an undeflected configuration. A second longitudinal axis is defined by the radial plane of the second opening when in an undeflected configuration. The sidewall at the first interior compartment has a width perpendicular to the first longitudinal axis and a length along the first longitudinal axis. The neck extension has a width perpendicular to the second longitudinal axis and a length along the second extension. The width of the neck extension is smaller than the width of the first interior compartment.

The proximal end of the neck extension at the first interior compartment defines an entryway intersection between the first compartment and the second compartment.

According to another aspect of the invention, a tissue containment bag is provided. The tissue containment bag includes a first opening and a second opening interconnected by a sidewall of flexible material. The sidewall defines a first interior compartment and a base configured for receiving a tissue specimen through the first opening into the first interior compartment and supporting the tissue specimen on the base. The sidewall forms an elongated hollow, sleeve-like neck extension defining a second interior compartment having a proximal end interconnected with the first interior compartment and a distal end interconnected with the second opening. The second opening is in fluidic communication with the second interior compartment. The second interior compartment is in fluidic communication with the first interior compartment and the first interior compartment is in fluidic communication with the first opening. The proximal end of the neck extension is connected to the base of the first interior compartment. The neck extension extends in a direction along a first longitudinal axis defined by the radial plane of the first opening when the bag is in an undeflected configuration. A second longitudinal axis is defined by the radial plane of the second opening when in an undeflected configuration. The sidewall at the first interior compartment has a width perpendicular to the first longitudinal axis and a length along the first longitudinal axis. The neck extension has a width perpendicular to the second longitudinal axis and a length along the second extension. The width of the neck extension is smaller than the width of the first interior compartment. The proximal end of the neck extension at the first interior compartment defines an entryway intersection between the first compartment and the second compartment.

According to another aspect of the invention, a containment vessel is provided. The containment vessel includes a first opening at a first end, a second opening at a second end and a sidewall interconnecting the first opening and the second opening. The sidewall defines an interior extending between the first opening and the second opening. The sidewall has a diameter and cross-section perpendicular to a longitudinal axis and a length. The containment vessel further includes at least one fastener connected to the sidewall around the interior at a location between the first opening and the second opening. The fastener is configured to reduce the diameter of the sidewall at the location of the fastener.

According to another aspect of the invention, a method for deploying a tissue containment bag inside a body cavity is provided. The method includes the step of providing a tissue containment bag having a first opening and a second opening interconnected by a sidewall of flexible material. The sidewall defines a first interior compartment and a base configured for receiving a tissue specimen through the first opening into the first interior compartment and supporting the tissue specimen on the base. The sidewall forms an elongated hollow, sleeve-like neck extension defining a second interior compartment having a proximal end interconnected with the first interior compartment and a distal end interconnected with the second opening. The second opening is in fluidic communication with the second interior compartment. The second interior compartment is in fluidic communication with the first interior compartment and the first interior compartment is in fluidic communication with the first opening. The proximal end of the neck extension is connected to the first interior compartment. The neck extension extends outwardly from the first interior compartment when in a deployed configuration. The neck extension has a retracted delivery configuration. The method includes the step of inserting the tissue containment bag into a body cavity while in a delivery configuration. The method includes the step of moving the neck extension from the delivery configuration to a deployed configuration inside the body cavity.

According to another aspect of the invention, a method for removing a tissue specimen from a body cavity is provided. The method includes the step of providing a tissue containment bag having a first opening at a first end, a second opening at a second end and a sidewall interconnecting the first opening and the second opening. The sidewall defines an interior extending between the first opening and the second opening having a diameter and cross-section perpendicular to a longitudinal axis. The tissue containment bag has a resilient, compressible ring connected to the sidewall coaxial with the second opening that is configured to keep the second opening in an open configuration. The method includes the step of inserting the second opening and ring of the tissue containment bag through a body orifice or incision into the body cavity. The method includes the step of inserting a tissue specimen through the second opening into the interior of the tissue containment bag. The method includes the step of moving the second opening and ring into the interior of the tissue containment bag past the tissue specimen located inside the containment bag toward the first opening to pouch the tissue specimen inside the containment bag.

According to another aspect of the invention a method for performing a hysterectomy on a patient is provided. The method includes the step of making an abdominal incision to access a body cavity. The method includes the step of mobilizing a uterus inside the body cavity. The method includes the step of providing a tissue containment bag having a first opening and a second opening interconnected by a sidewall of flexible material. The sidewall defines a first interior compartment and a base configured for receiving a tissue specimen through the first opening into the first interior compartment and supporting the tissue specimen on the base. The sidewall forms an elongated hollow, sleeve-like neck extension defining a second interior compartment having a proximal end interconnected with the first interior compartment and a distal end interconnected with the second opening. The second opening is in fluidic communication with the second interior compartment. The second interior compartment is in fluidic communication with the first interior compartment and the first interior compartment is in fluidic communication with the first opening. The proximal end of the neck extension is connected to the first interior compartment. The neck extension extends outwardly from the first interior compartment when in a deployed configuration. The method includes the step of inserting the tissue containment bag into the body cavity. The method includes the step of inserting the uterus through the first opening and into the first interior compartment of the tissue containment bag. The method includes the step of moving the neck extension into a deployed configuration. The method includes the step of pulling the second opening of the tissue containment bag through the vaginal canal to outside of the patient while the first interior compartment remains in the body cavity. The method includes the step of pulling the first opening of the tissue containment bag through the abdominal incision while the first interior compartment remains in the body cavity. The method includes the step of simultaneously debulking the uterus inside the tissue containment bag through either one of the first opening or second opening while observing the uterus inside first interior compartment through the other one of the first opening or second opening. The method includes the step of removing the uterus from the patient.

According to another aspect of the invention a method for removing a tissue specimen from a body cavity is provided. The method includes the step of making an abdominal incision to access a body cavity. The method includes the step of mobilizing a tissue specimen inside the body cavity. The method includes the step of providing a tissue containment bag having a first opening and a second opening interconnected by a sidewall of flexible material. The sidewall defines an interior compartment. The sidewall has an external first pocket on one side of the sidewall and an external second pocket on an opposite side. The first pocket and second pocket are located near the second opening. The method includes the step of inserting the tissue containment bag into the body cavity. The method includes the step of inserting the tissue specimen into the interior compartment through the first opening of the tissue containment bag. The method includes the step of folding the sidewall distal to the first pocket and placing the rolled sidewall into the first pocket. The method includes the step of tucking the first pocket into the second pocket.

According to another aspect of the invention, a method for extracting a tissue specimen from inside a body cavity is provided. The method includes the step of providing a containment vessel having a first opening at a first end, a second opening at a second end, and a sidewall interconnecting the first opening and the second opening. The sidewall has a diameter and cross-section perpendicular to a longitudinal axis and defines an interior and length extending between the first opening and the second opening. The containment vessel has a plurality of fasteners connected to the sidewall around the interior and spaced apart along the length of the containment vessel between the first opening and the second opening. Each fastener is configured to individually reduce the diameter of the sidewall at the location of the fastener when activated. The method includes the step of inserting at least the second opening of the containment vessel into the body cavity. The method includes the step of placing a tissue specimen having a first diameter through the second opening into the interior of the containment vessel. The method includes the step of reducing the diameter of the tissue specimen to a second diameter by reducing the diameter of the containment vessel by activating one or more fastener in the location of the tissue specimen. The method includes the step of removing the tissue specimen having the reduced second diameter.

BRIEF DESCRIPTION OF THE DRAWINGS

FIG. 6 is a schematic of a containment bag inside a patient according to the present invention.
FIG. 7C is a top perspective view of a containment bag according to the present invention.
FIG. 7D is a top perspective view of a containment bag according to the present invention.

FIG. 14A is a schematic of a grasper pulling a specimen into a containment bag according to the present invention.

FIG. 14B is a schematic of a specimen inside a containment bag and a grasper grabbing the second opening of the containment bag according to the present invention.

FIG. 14C is a schematic of a specimen inside a containment bag and a grasper pulling to invert the second opening of the containment bag proximally past the specimen to pouch the specimen inside the containment bag according to the present invention.

FIG. 20 is a schematic view of a trocar inserted into an opening of a containment bag at a tissue wall according to the present invention.

FIG. 21 is a schematic view of a proximal end and opening of a containment bag pulled through the lumen of a trocar at a tissue wall according to the present invention.

FIG. 25 is a schematic view of an insufflation system for a containment bag and body cavity according to the present invention.

FIG. 26 is a schematic view of a double-walled containment bag and insufflation system according to the present invention.

FIG. 27 is a top perspective view of a containment bag with perforation according to the present invention.

FIG. 28 is a top perspective view of a containment bag with clip retention according to the present invention.

FIG. 29 is a top perspective view of a containment bag with adhesive retention according to the present invention.

DETAILED DESCRIPTION OF THE INVENTION

Figure 1A:
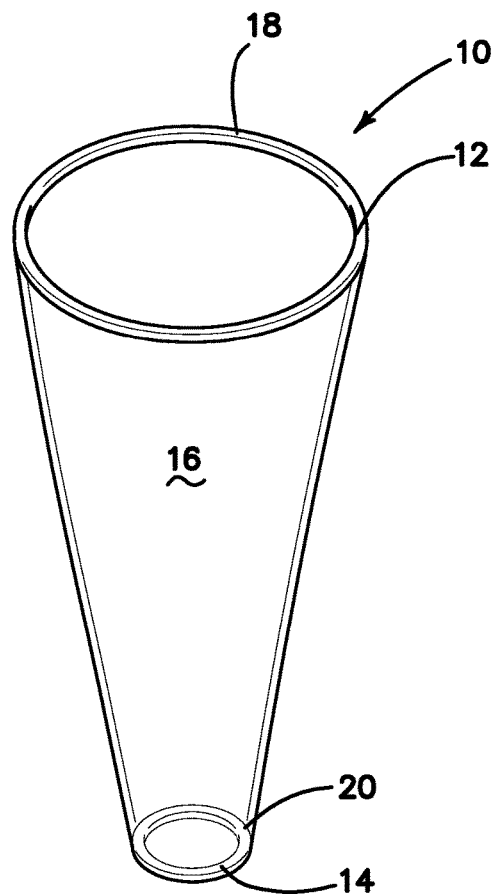
FIG. 1A is a top perspective view of a containment bag according to the present invention.
Figure 1B:
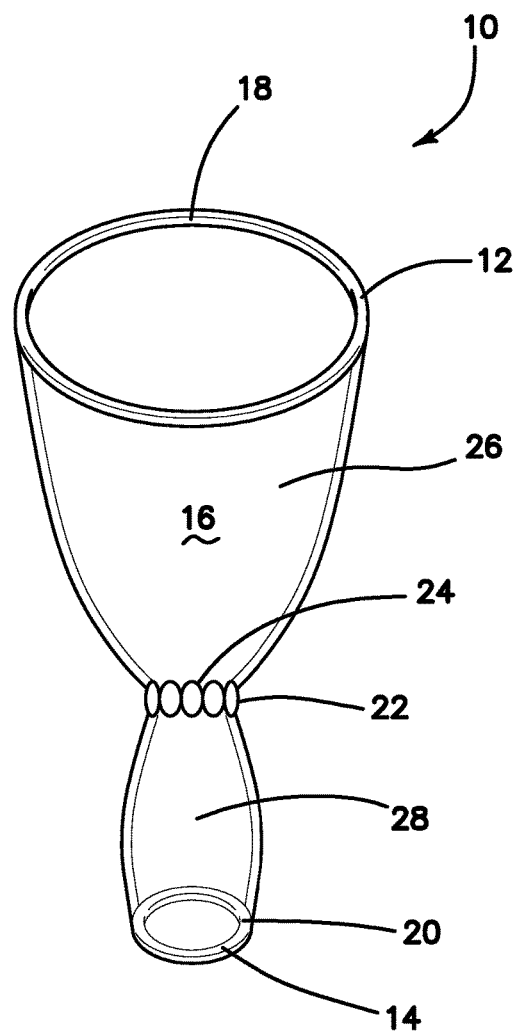
FIG. 1B is a top perspective view of a containment bag according to the present invention.

Turning now to FIGS. 1A-1B, there is shown a containment bag 10 according to the present invention. The containment bag 10 includes a first opening 12, also called a mouth, and a second opening 14 interconnected by a sidewall 16. A first ring 18 is provided at the first opening 12 and a second ring 20 is provided at the second opening 14. The rings 18, 20 are connected to the sidewall 16 by enclosing the rings 18, 20 in a pocket formed by the sidewall 16 heat sealed onto itself and/or with adhesive. The sidewall 16 is formed of any suitable flexible material including but not limited to polymer, fabric, polymer reinforced with fabric, mesh, nylon, fibers and the like. The first opening 12 is larger than the second opening 14 and the sidewall 16 forms a frusto-conical configuration. Accordingly, the first ring 18 is larger than the second ring 20. The sidewall 16 is formed by heat-sealing the sidewall material longitudinally forming one or more seams along the length of the bag 10. As shown in FIG. 1B, the bag 10 may optionally include at least one fastener 22 connected to sidewall 16 at a location between the two rings 18, 20. In one variation, the fastener 22 includes a cincture, belt, girdle or cinch comprising a string, tape or other means known in the art that girds the sidewall 16 at least in part and can be pulled to reduce the diameter of the sidewall 16 in the location of the fastener 22. Other types of fasteners 22 are within the scope of the present invention. Multiple fasteners 22 may be also employed and spaced apart along the longitudinal axis of the bag 10 as will be described in greater detail below. The single fastener 22 functions to reduce the diameter of the bag 10 at a location approximately midway between the two openings 12, 14 and as a result creates a base 24 also called a bottom or floor or semi-floor for the bag 10 upon which a surgical tissue specimen may be supported. In general, the fastener 22 also functions to close the sidewall 16 and create two compartments or chambers in the bag 10 a first proximal compartment 26 and a second distal compartment 28 separated by the cinch. The fastener 22 can advantageously be released such that lumen of the bag 10 is uninterrupted from the first opening 12 to the second opening 14. A first tether and tag may be attached to the first ring 18 and a second tether and tag may be attached to the second ring 20 to facilitate placement of the bag 10 and to facilitate removal of the bag 10. As shown in FIGS. 1A and 1B, the first opening 12 and second opening 14 are coaxial or substantially located along the longitudinal axis of the bag 10 when the bag 10 is in a normal undeflected orientation forming a sleeve-like, tubular structure.

In use for a surgical procedure that involves detaching a uterus or other surgical target and its subsequent morcellation, the containment bag 10 according to the present invention is employed. In use, an incision is first made in the patient's abdominal region, typically, in the umbilicus. A retractor is inserted into the incision.

The retractor (not shown) typically comprises a first ring and a second ring interconnected by a flexible sidewall. The sidewall defines a lumen interconnected between an opening of the first ring and an opening of the second ring of the retractor. The second ring is resilient and compressible. When compressed the second ring forms an oval elongated shape and is inserted through the incision in the abdominal wall and into an abdominal cavity which may have already been expanded by insufflation gasses to create a surgical working space. When the second ring is no longer compressed into a low-profile condition it freely expands into its original high-profile configuration due to its own resiliency as a result of being made of suitable materials, construction and design. The sidewall of the retractor connects the second ring to the first ring. When the second ring is located inside the patient, the sidewall traverses the incision and the abdominal wall while the first ring resides above the abdominal wall outside the patient. Because the sidewall is relatively loose, the small incision tends to bow the sidewall inwardly toward the retractor lumen. The first ring is configured to be rolled down to retract and enlarge the opening in the abdominal wall. The first ring is flipped about itself to roll the sidewall material onto the first ring of the retractor reducing the length of the retractor. As the length of the retractor is decreased the second ring is drawn closer to the first ring. Continued rolling of the first ring reduces the length of the sidewall increases tension on the sidewall moving it outwardly toward its cylindrical shape and thereby, retracting tissue in contact with the outer surface of the sidewall and, thereby, enlarging the opening in the abdominal wall. The first ring has an elongated, oblong, oval cross-sectional shape which facilitates rolling of the sidewall and prevents unrolling of the sidewall compared to a ring having a circular cross-section. The sidewall is made of polyurethane laminate or similar material including woven or reinforced polymeric material to resist cuts and breaks through the sidewall. Various examples of access systems to be included or integrated into the morcellation system of the present invention in which the entire access systems, portions of the access systems or combinations of access systems and/or components thereof arranged to provide a channel and/or a protective region in accordance with various embodiments of the present invention are described in U.S. patent application Ser. No. 13/865,854, filed Apr. 18, 2013; 61/880,641, filed Sep. 20, 2013; Ser. No. 12/578,422, filed Oct. 13, 2009, 61/104,963, Oct. 13, 2008; Ser. No. 12/358,080, filed Jan. 22, 2009; Ser. No. 11/374,188, filed Mar. 13, 2006; Ser. No. 11/683,821, filed Mar. 8, 2007; Ser. No. 12/396,624, filed Mar. 3, 2009; Ser. No. 14/209,161, filed Mar. 13, 2014; Ser. No. 12/873,115, filed Aug. 31, 2010; Ser. No. 12/840,989, filed Jul. 21, 2010; Ser. No. 11/548,758, filed Oct. 12, 2006; Ser. No. 10/516,198, filed Nov. 30, 2004; and Ser. No. 10/666,579, filed Sep. 17, 2003; the entire disclosures of which are hereby incorporated by reference as if set forth in full herein. Also, U.S. Provisional Patent Application No. 61/970,436 filed on Mar. 26, 2014, 61/983,413 filed on Apr. 23, 2014, 62/014,038 filed on Jun. 18, 2014, 62/024,698 filed on Jul. 15, 2014, 62/079,171 filed Nov. 13, 2014, 62/081,297 filed on Nov. 18, 2014, 61/982,997 filed on Apr. 23, 2014 and 62/107,107 filed Jan. 23, 2015 are all incorporated by reference in their entireties.

After the retractor is inserted into the incision and the opening at the incision is enlarged, an access port cap/platform is attached to the first ring of the retractor covering and sealing the opening created by the retractor. The access port cap may include one or more access ports including an insufflation port and/or be made of penetrable material such as gel that seals around an inserted instrument. Insufflation gas is delivered across the incision sealed with the access port cap to insufflate the patient's abdominal cavity and create an expanded surgical working space. The body cavity is insufflated by delivering gas across the access port cap into the abdominal cavity. Instruments such as graspers, scissors, scopes, and electrocautery/electrosurgical instruments are inserted through the access port to detach the uterus. The instruments are removed and the access port cap/platform is removed.

In use, the bag 10 is inserted through the incision in the umbilicus. The access port cap/platform is re-attached to the first ring of the retractor and the body cavity is re-insufflated to allow for visualization of the procedure via a scope inserted through the access port cap/platform or secondary incision. The detached tissue specimen such as the uterus is inserted into the first opening 12 of the bag 10 with graspers while inside the abdominal cavity. The first opening 12 is larger than the second opening 14 of the bag 10 making it easy to introduce the tissue specimen. Also, the rings 18, 20 are flexible and can be compressed into a low-profile configuration suitable for insertion through a small port and/or incision. The tether attached to the first ring 18 is pulled to bring the larger first ring 18 through the umbilicus incision. The access port cap/platform is removed and the first ring 18 of the bag 10 and a portion of the sidewall 16 near the first ring 18 is pulled out of the first incision. A portion of the sidewall 16 overlays the first ring of the retractor and the access port cap/platform is re-attached to the retractor capturing the bag between the access port cap/platform and the retractor ring. The tether attached to the second ring 20 of the bag 10 grasped from the vaginal canal which is now opened because the uterus has been detached. The second ring 20 of the bag 10 is pulled through the vaginal opening and a second access port cap/platform is attached to the second ring 20. The second ring 20 may be compressed into a low-profile orientation to facilitate removal of the second ring 20. The access port cap/platform is smaller to fit the smaller second ring 20. A scope is inserted through the second access port cap/platform into the bag 10. The second opening 14 is smaller in order to be sized and configured for placement along the vaginal canal and/or for the insertion of a narrow long instrument such as a scope for observation or a power or manual morcellating instrument for morcellation of the uterus inside the bag. Alternatively, a trocar may be inserted through the second access port cap/platform and a scope inserted through the trocar. In yet another variation, an access port cap/platform is not employed and a balloon trocar is inserted into the second opening 14 through which a scope is inserted. In another variation, a scope is inserted into the bag 10 without an access port cap/platform or retractor. In another variation, a retractor may be placed inside the second opening 14 of the bag 10 and the vaginal canal retracted together with the bag 10 with the retractor. Or, alternatively, the second opening 14 of the bag 10 is pulled through the lumen of a retractor already in position within the vaginal canal.

A morcellator is inserted through the first access port cap/platform and morcellation of the specimen is commenced under observation via the scope inserted through the vaginal canal and through the second opening 14 in the bag 10 advantageously providing an unobstructed view of the procedure. This procedure constitutes morcellation through the umbilicus or other incision site in the abdominal region. An alternative to morcellating through the umbilicus is morcellating through the vaginal canal which will be described further below.

After the morcellation through the umbilicus or other incision site is completed, the bag 10 is removed from the patient by first removing the access port cap/platform at the vaginal canal attached to the smaller second ring 20. If a retractor is employed at the vaginal opening, it is also removed. The second opening 14 of the bag is sealed prior to removal of the bag by various methods which will be described in greater detail below. For example, the sidewall 16 near the second opening 14 may be rolled-up and tucked into one or more pockets or the sidewall 16 may be sealed by tying the distal end of the bag 10 into a knot. The first access port cap/platform and retractor, if one is employed, are removed at the umbilicus or other abdominal incision. With the second opening 14 of the bag sealed, the entire bag 10 is removed from through the abdominal incision. At the point of removal, most of the uterus or tissue specimen is already removed or reduced in size by the morcellation process making removal of large specimens easy. Sealing the second opening 14 prior to removal of the bag prevents the bag contents from spilling out. Hence, the system remains fully contained.

In another variation of morcellation through the umbilicus or other abdominal location, after the bag 10 is inserted into the abdominal cavity and a specimen is inserted into the first opening 12. Before the first ring 18 is pulled to the abdominal surface of the patient, the access port cap/platform is removed from the retractor and also, the retractor is removed. Then, the first ring 18 is squeezed into a low-profile configuration and a proximal portion of the bag 10 is pulled out through the umbilicus with the remainder of the bag with the specimen inside it remaining inside the abdominal cavity. The retractor is re-inserted into the mouth of the bag 10 and then the tissue is advantageously retracted together with the sidewall 16 of the bag 10 as shown in FIG. 6. The access port cap/platform is re-attached to the retractor ring as shown in FIG. 6. The proximal portion of the bag 10 overlays the retractor and first ring 18 of the bag 10 is resident outside of the patient.

As an alternative to morcellation through the umbilicus, morcellation of the tissue specimen, such as the uterus, through the vaginal canal will now be described. The bag 10 is inserted through the incision in the umbilicus or other abdominal location. A retractor may be inserted into the incision and the surrounding tissue retracted. The access port cap/platform is re-attached to the first ring of the retractor and the body cavity is re-insufflated to allow for visualization of the procedure via a scope inserted through the access port cap/platform or secondary incision. The detached tissue specimen such as the uterus is inserted into the first opening 12 of the bag 10 with graspers. The tether attached to the first ring 18 is pulled to bring the larger first ring 18 through the vaginal canal instead of through the umbilical incision. The first ring 18 of the bag 10 and a portion of the sidewall 16 near the first ring 18 is pulled out of the vaginal canal. A retractor is inserted into the first opening 12 of the bag 10 and the vaginal canal is retracted together with the bag 10 in the location of the retractor by rolling the first ring about itself to wind the sidewall around the first ring of the retractor. An access port cap/platform is attached to the retractor ring. Alternatively, a retractor may be placed before the bag 10 is pulled through the vaginal opening in which case the access port cap/platform captures the bag 10 against the first ring of the retractor. The tether attached to the smaller second ring 20 of the bag 10 is grasped from the umbilical incision or other abdominal incision. The second ring 20 of the bag 10 is pulled through the umbilical incision or other abdominal incision and a second access port cap/platform is attached to the second ring 20. The second access port cap/platform is smaller to fit the smaller second ring 20 relative to the first access port cap/platform. A scope is inserted through the second access port cap/platform into the bag 10 to observe the morcellation process. Alternatively, a trocar may be inserted through the second access port cap/platform and a scope inserted through the trocar. Alternatively, a balloon trocar may be employed without an access cap/platform or retractor or simply the scope may be inserted into the bag 10 at the second opening 14 resident at the umbilical or other incision. A morcellator is inserted through the first access port cap/platform through the vaginal canal and morcellation of the specimen is commenced under observation via the scope that is inserted through the umbilical first incision and through the second opening 14 in the bag 10 advantageously providing an unobstructed view of the procedure. The bag 10 is removed from the patient by removing the first access port cap/platform attached to the retractor at the vaginal opening. The retractor at the vaginal opening is also removed. Any retractor or second access port cap/platform at the second opening 14 is removed. The second opening 14 of the bag 10 is sealed by various methods which will be described in greater detail below. For example, the sidewall 16 near the second opening 14 may be rolled-up and tucked or the sidewall 16 may be tied into a knot. With the second opening 14 sealed, the entire bag 10 is removed through the vaginal canal. At the point of removal, most of the uterus or tissue specimen is already removed or reduced in size by the morcellation process.

Figure 2:
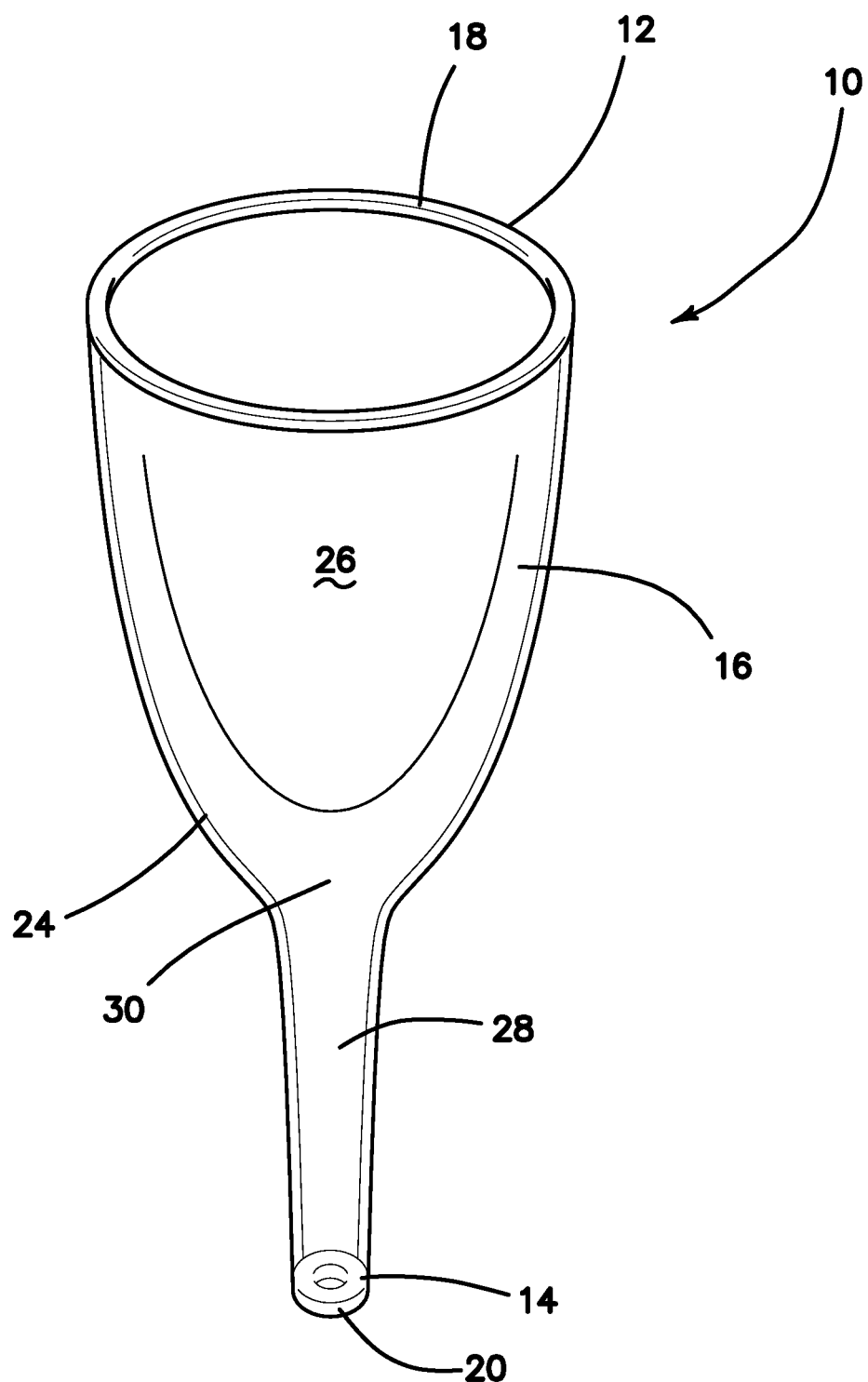
FIG. 2 is a top perspective view of a containment bag according to the present invention.

Turning now to FIG. 2, another containment bag 10 variation will now be described using like numbers to designate like parts of the invention. The bag 10 of FIG. 2 may also be used in any one or more of the methods described above. The bag 10 includes a first opening 12, also called a mouth, and a second opening 14 interconnected by a sidewall 16. A first ring 18 is provided at the first opening 12 and a second ring 20 is provided at the second opening 14. The rings 18, 20 are connected to the sidewall 16 by enclosing the rings 18, 20 in a pocket formed by the sidewall 16 heat sealed onto itself and/or with adhesive. The sidewall 16 is formed of any suitable flexible material including polymer, fabric, polymer reinforced with fabric, mesh, nylon, fibers and the like. The first opening 12 is larger than the second opening 14 and, accordingly, the first ring 18 is larger than the second ring 20. The sidewall 16 forms a funnel-like shape configuration dividing the lumen of the bag 10 into a first compartment 26 and a second compartment 28. The first compartment 26 is substantially parabolic, funnel-like in shape having curved sidewalls when the bag 10 is in a natural undeflected orientation. The sidewall 16 is formed by heat-sealing the sidewall material longitudinally forming one or more seams along the length of the bag 10. At the intersection of the first compartment 26 and second compartment 28, there is a reduced diameter location entryway 30 that advantageously reduces the amount of specimen passing therethrough and, as a result, creates a base 24 also called a bottom or floor or semi-floor for the bag 10 upon which a surgical tissue specimen may be supported for morcellation with the small entryway preventing tissue specimen from readily moving into the second compartment 28. The curved sidewall 16 helps retain the specimen at the base 24 forming a reservoir-like configuration. From the intersection 30 to the second opening 14, the cross-sectional opening is substantially constant and/or gradually increases or decreases to create a tubular, sleeve-like section of the bag 10 that is sized and configured for placement through the vaginal canal and that is much narrower than the first compartment 26 which has a larger cross-sectional opening along the first compartment 26. A first tether and tag may be attached to the first ring 18 and a second tether and tag may be attached to the second ring 20 to facilitate placement of the bag 10 and to facilitate removal of the bag 10.

Figure 3A:
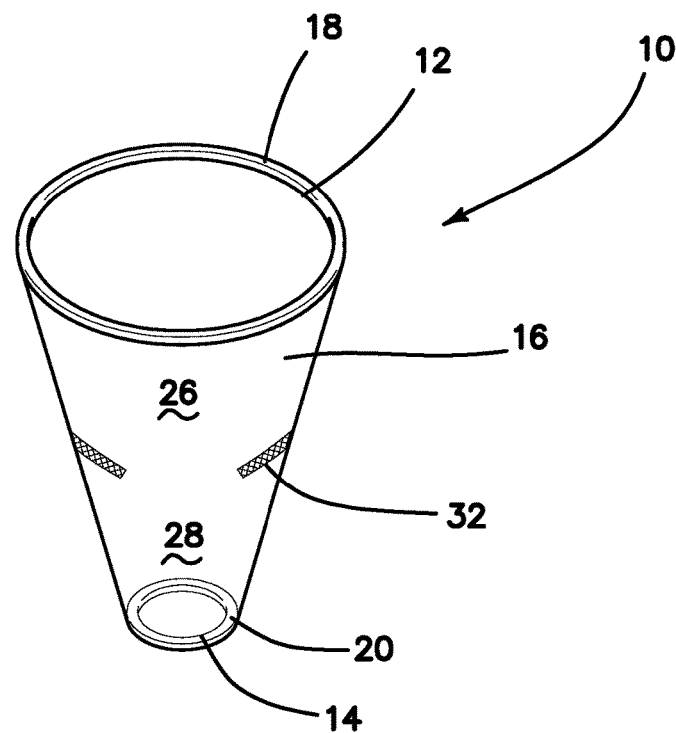
FIG. 3A is a top perspective view of a containment bag according to the present invention.
Figure 3B:
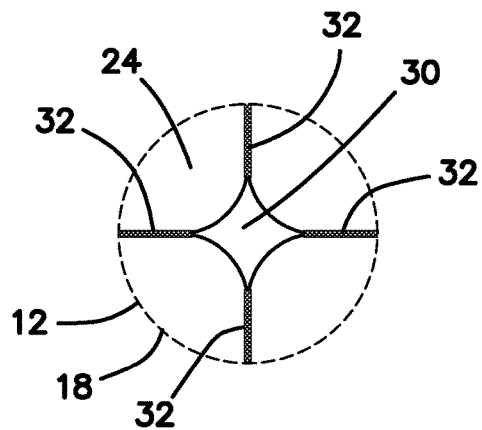
FIG. 3B is a top view of a containment bag according to the present invention.
Figure 3C:
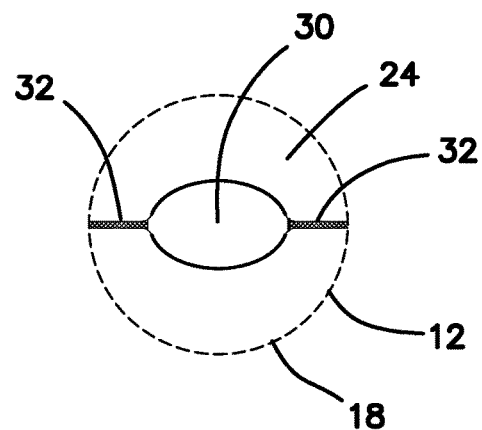
FIG. 3C is a top view of a containment bag according to the present invention.

Turning now to FIGS. 3A-3C, there is shown another containment bag 10 according to the present invention. The containment bag 10 includes a first opening 12, also called a mouth, and a second opening 14 interconnected by a sidewall 16. A first ring 18 is provided at the first opening 12 and a second ring 20 is provided at the second opening 14. The rings 18, 20 are connected to the sidewall 16 by enclosing the rings 18, 20 in a pocket formed by the sidewall 16 heat sealed onto itself and/or with adhesive. The sidewall 16 is formed of any suitable sheet of flexible material including but not limited to polymer, polymer reinforced with fabric, mesh, nylon, fibers and the like. The first opening 12 is larger than the second opening 14 and the sidewall 16 forms a frusto-conical configuration. Accordingly, the first ring 18 is larger than the second ring 20. The sidewall 16 is formed by heat-sealing the sidewall material longitudinally forming one or more seams along the length of the bag 10. The bag 10 includes one or more inwardly extending lateral seams 32 reducing the lumen of the bag 10 at a location between the first opening 12 and the second opening 14. The seams 32 are formed into the sidewall 16 by selectively hot-sealing portions of the sidewall 16 together to reduce the diameter of the sidewall 16 in the location of the seam. Four seams 32 spaced around the sidewall 16 are shown in FIG. 3B and two seams 32 are shown oppositely disposed in FIG. 3C. The seams 32 function to reduce the diameter of the bag 10 at a location anywhere including midway between the two openings 12, 14 and as a result creates a base 24 also called a bottom or floor or semi-floor for the bag 10 upon which a surgical tissue specimen may be supported. In general, the seams 32 function to close the sidewall 16 and create two compartments in the bag 10, a first proximal compartment 26 and a second distal compartment 28, separated by the seams 32. At the intersection of the first compartment 26 and second compartment 28 there is a reduced entryway 30 that advantageously reduces the amount of specimen passing therethrough and, as a result, creates a base 24 or semi-base. A first tether and tag may be attached to the first ring 18 and a second tether and tag may be attached to the second ring 20 to facilitate placement of the bag 10 and to facilitate removal of the bag 10.

Figure 4:
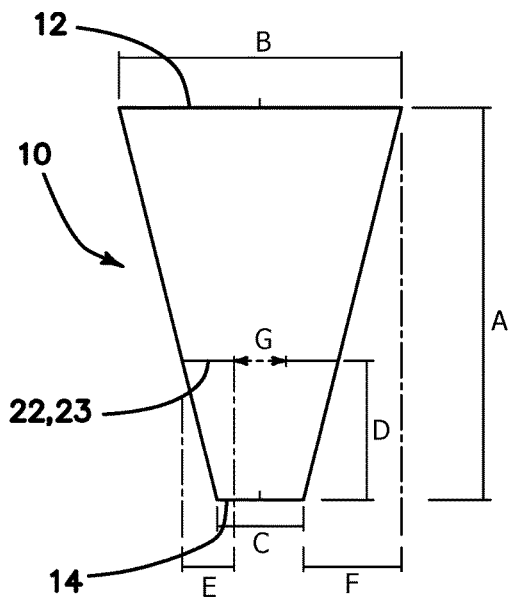
FIG. 4 is a side view of a containment bag according to the present invention.

Turning now to FIG. 4, there is shown a containment bag 10 for the purposes of showing the various dimensions of the bag 10 according to the invention. The dimensions are not limited to the exact configuration for the bag 10 but approximately the same dimensions may be used for any one or more the bag variations disclosed herein. The length A of the bag 10 is approximately 20.0 inches. The diameter B at the first opening 12 is approximately 9.0 inches. The diameter C at the second opening 14 is approximately 5.0 inches. The distance D to the seams 32 or fastener 22 from the second opening 14 is approximately 8.0 inches. The diameter G of the entryway 30 is approximately 1.5 inches. The rings 18, 20 are rigid, resilient and flexible and made of plastic capable of assuming a low-profile, compressed configuration from a relaxed, normal, undeformed high-profile expanded configuration. The low-profile configuration is elongated and oval with the opening reduced in side and configured for easy insertion through a small incision. The high-profile configuration is substantially circular but may be of any shape. The rings 18, 20 are capable of supporting the bag sidewall 16 opening the bag sidewall 16 as the ring 18, 20 moves from a low-profile configuration to a high profile configuration. The rings 18, 20 are resilient and tend to spring back to their undeformed high-profile configuration. A clinician can easily compress the ring 18, 20 to reduce its size for insertion through an incision into a body cavity.

Figure 5A:
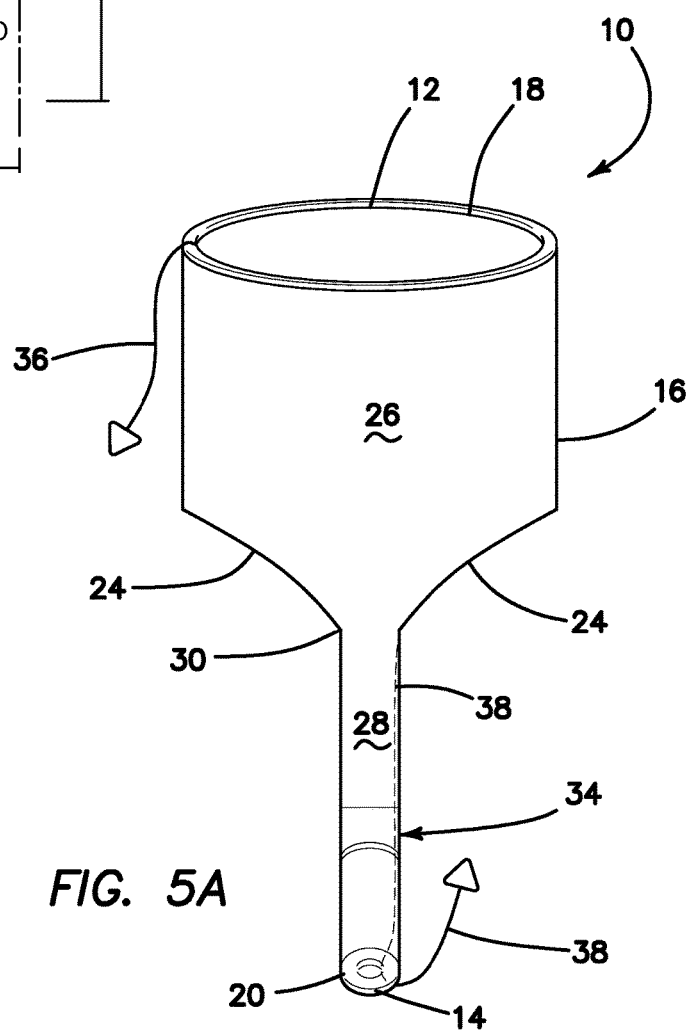
FIG. 5A is a top perspective view of a containment bag according to the present invention.
Figure 5B:
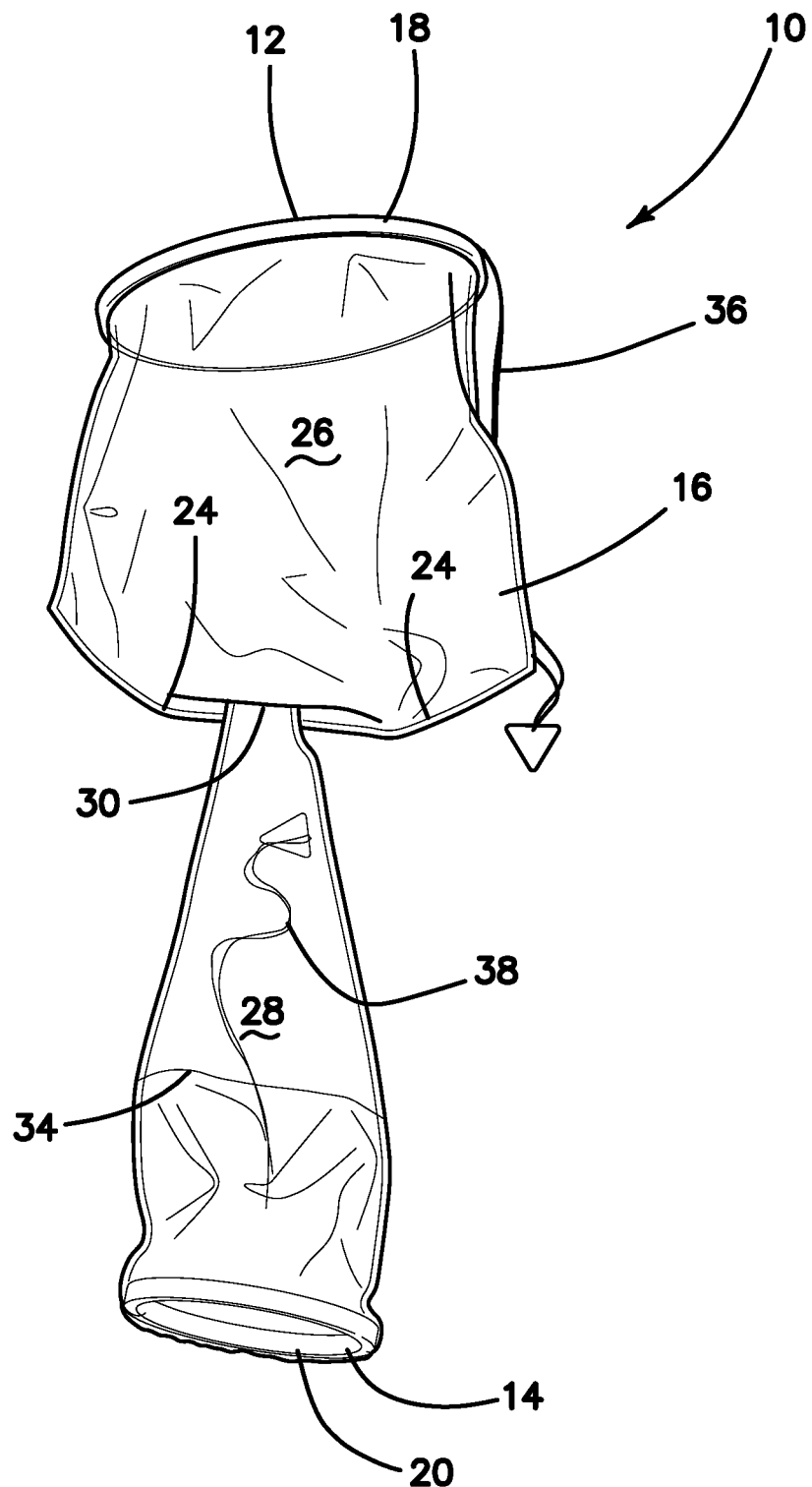
FIG. 5B is a top perspective view of a containment bag according to the present invention.

Turning now to FIGS. 5A-5B, there is shown another variation of the containment bag 10 wherein like reference numbers are used to describe like parts. The containment bag 10 includes a first opening 12, also called a mouth, and a second opening 14 interconnected by a sidewall 16. A first ring 18 is provided at the first opening 12 and a second ring 20 is provided at the second opening 14. The rings 18, 20 are connected to the sidewall 16 by, for example, enclosing the rings 18, 20 in a pocket formed by the sidewall 16 heat sealed onto itself and/or with adhesive. The sidewall 16 is formed of any suitable flexible material including fabric, polymer, polymer reinforced with fabric, mesh, nylon, fibers and the like. The first opening 12 is larger than the second opening 14. Accordingly, the first ring 18 is larger than the second ring 20. The sidewall 16 is formed by heat-sealing the sidewall material longitudinally forming one or more seams along the length of the bag 10. As shown in FIGS. 5A-5B, the bag 10 is formed into a first compartment 26 and a second compartment 28 with an entryway 30 at their intersection. The first compartment 26 has a proximal section that is substantially cylindrical in shape with a vertical sidewall 16 connected to a distal section that is funnel-like in shape having an angled sidewall 16 when the bag 10 is in a normal undeflected orientation as shown. The distal section that is funnel-like in shape is connected to the second compartment 28 via the entryway 30. The entryway 30 is sized and configured to permit a scope to pass. A scope would be typically inserted through the second opening 14 into the second compartment 28 and extended all the way to near the entryway 30 for observation of morcellation taking place in the first compartment 26. Therefore, the entryway 30 is sized as small as possible to prevent escape of specimen from the first compartment 26 and to form a large enough base 24 to support a specimen and large enough to receive the scope shaft. The angled sidewall 16 of the funnel-like distal section of the first compartment 26 forms the base 24 also called a bottom or floor or semi-floor for the bag 10 upon which a surgical tissue specimen may be supported. The entryway 30 is as small as the diameter of a 5-10 mm scope. In the variation shown in FIG. 5B, the diameter of the entryway 30 is smaller than the diameter of the second opening 14. The larger diameter at the second opening 14 compared to the diameter at the entryway 30 facilitates the second ring 20 being rolled upon itself to reduce the length of the second compartment 28. A third ring (not shown) may be further provided near the second ring 20 such that the second ring 20 and the third ring serve as a built-in, integral retractor of the like described above. The larger second opening 14 relative to the diameter at the entryway 30 also facilitates insertion of instruments and retraction of tissue. The sidewall 16 of the second compartment 28 angles outwardly progressively with distance from the entryway 30 to the second opening 20. The bag 10 of FIGS. 5A-5B is shown provided with a seal mechanism 34 configured to seal the second opening 20 so that specimen does not spill from the bag 10. The various possible seal mechanisms 34 that can be including in this variation as well as in any variation of the containment bag 10 will be described in greater detail below. A first tether/tag 36 may be attached to the first ring 18 and a second tether/tag 38 may be attached to the second ring 20 to facilitate placement of the bag 10 and to facilitate removal of the bag 10.

Figure 7A:
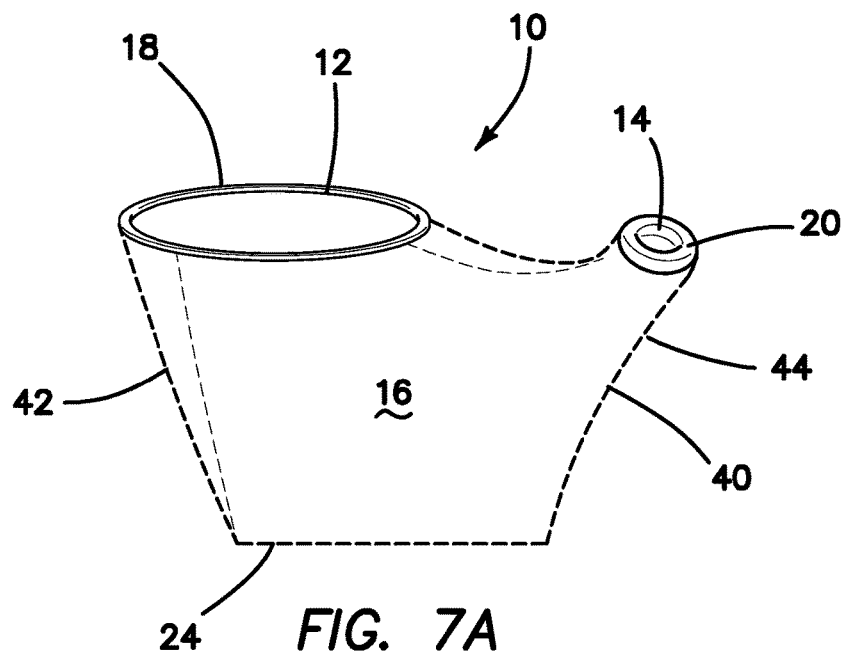
FIG. 7A is a top perspective view of a containment bag according to the present invention.
Figure 7B:
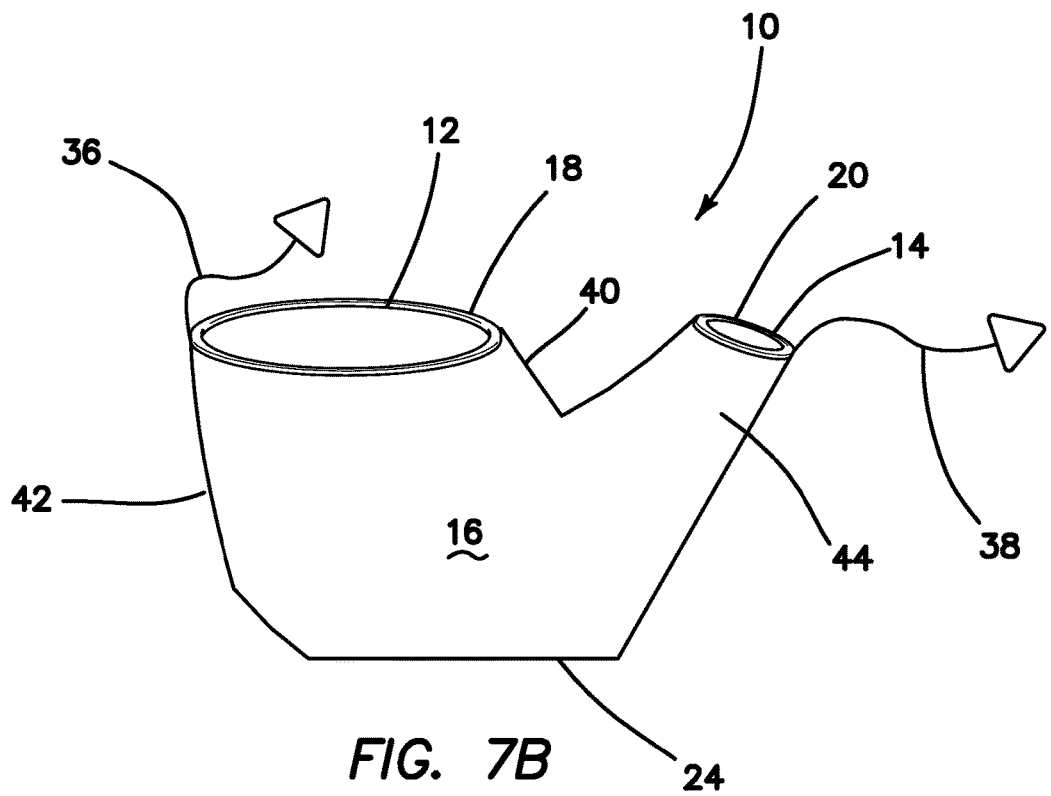
FIG. 7B is a top perspective view of a containment bag according to the present invention.
Figure 7E:
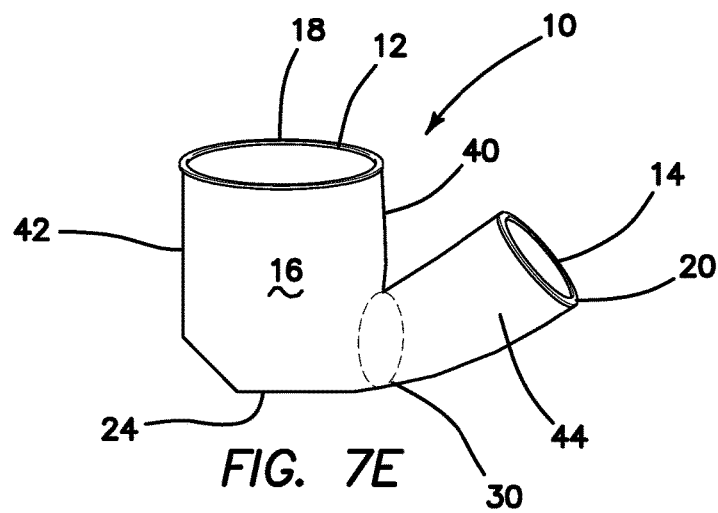
FIG. 7E is a top perspective view of a containment bag according to the present invention.
Figure 7F:
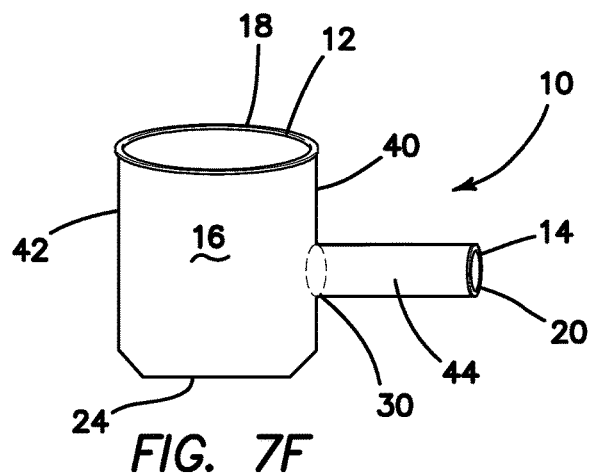
FIG. 7F is a top perspective view of a containment bag according to the present invention.
Figure 7G:
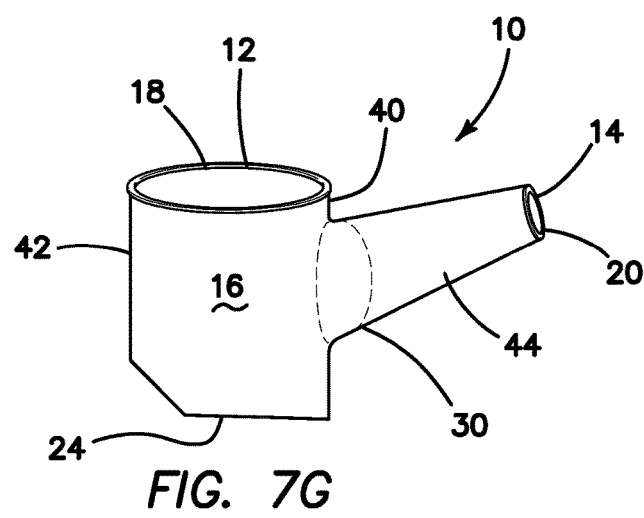
FIG. 7G is a top perspective view of a containment bag according to the present invention.
Figure 7H:
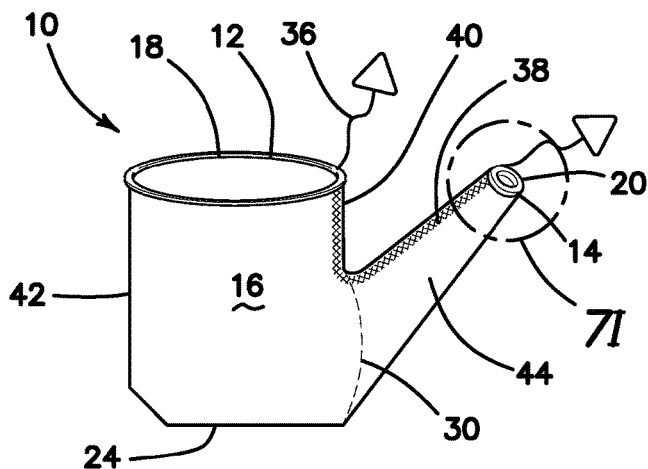
FIG. 7H is a top perspective view of a containment bag according to the present invention.
Figure 7I:
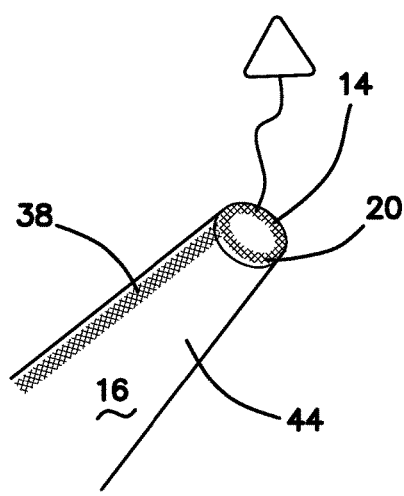
FIG. 7I is a sectional view taken along 7I of FIG. 7H of a containment bag according to the present invention.
Figure 7J:
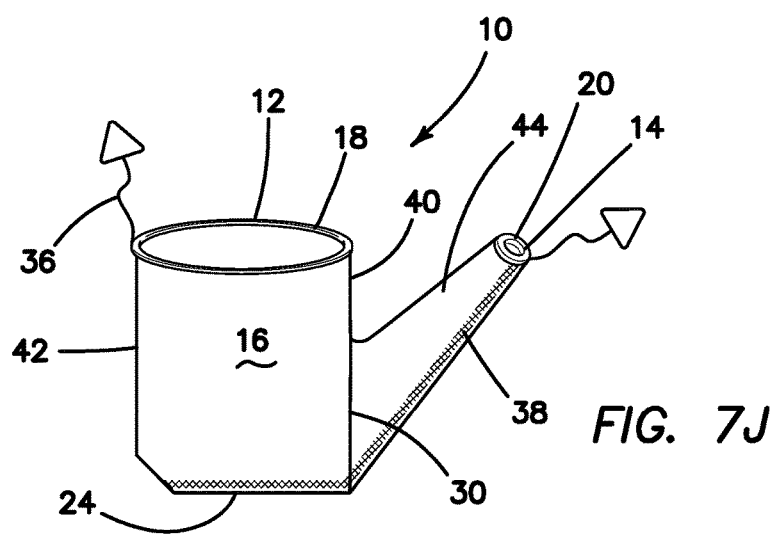
FIG. 7J is a top perspective view of a containment bag according to the present invention.
Figure 7K:
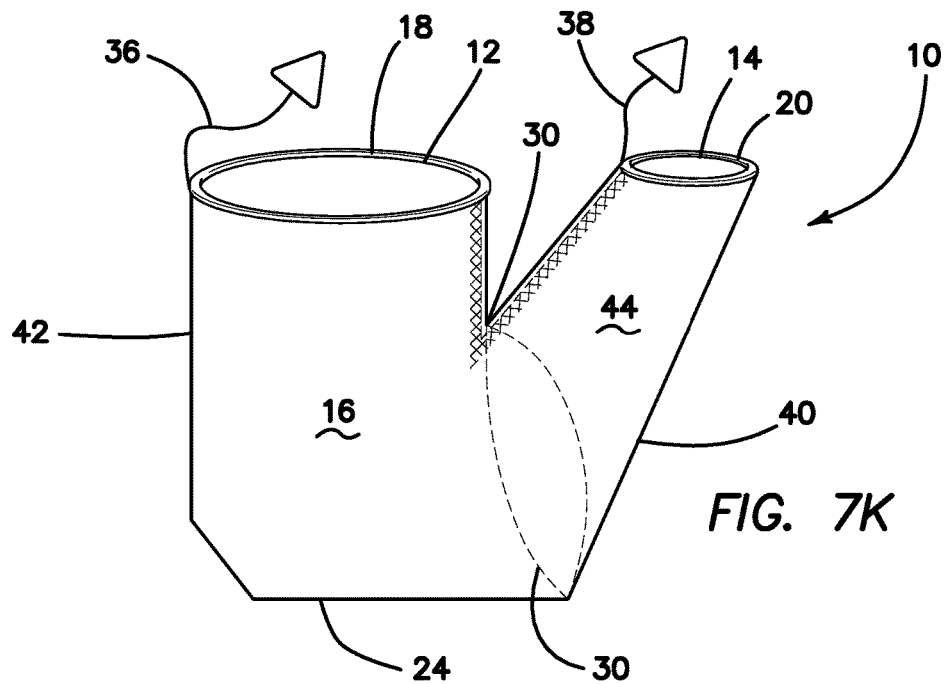
FIG. 7K is a top perspective view of a containment bag according to the present invention.
Figure 7L:
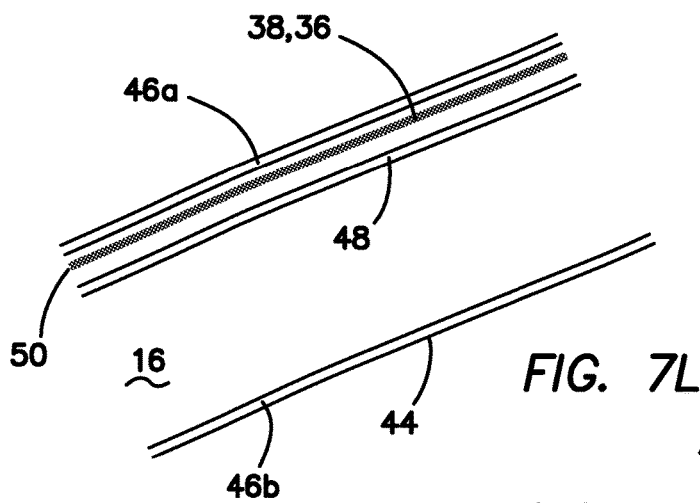
FIG. 7L is a sectional view of a containment bag according to the present invention.
Figure 7M:
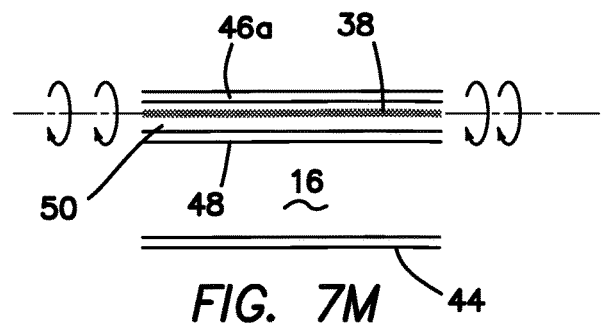
FIG. 7M is a sectional view of a containment bag according to the present invention.
Figure 7N:
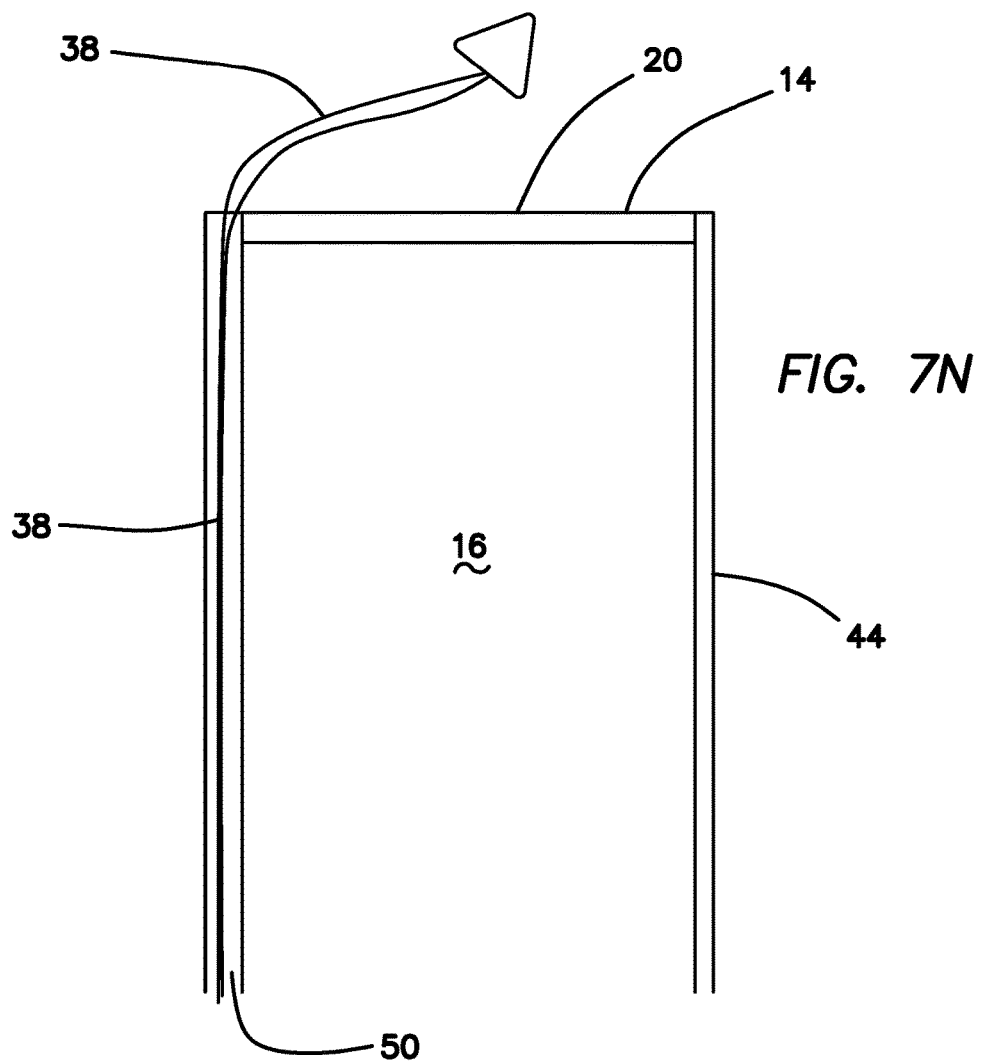
FIG. 7N is a sectional view of a containment bag according to the present invention.
Figure 7O:
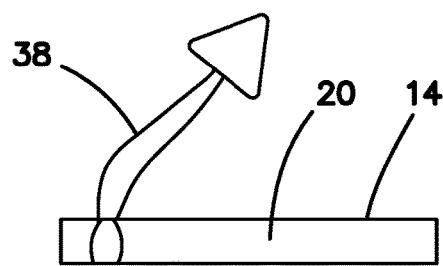
FIG. 7O is a sectional view of a containment bag according to the present invention.
Figure 7P:
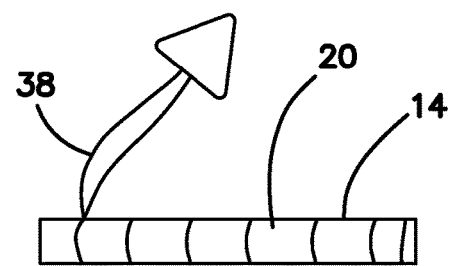
FIG. 7P is a sectional view of a containment bag according to the present invention.
Figure 7Q:
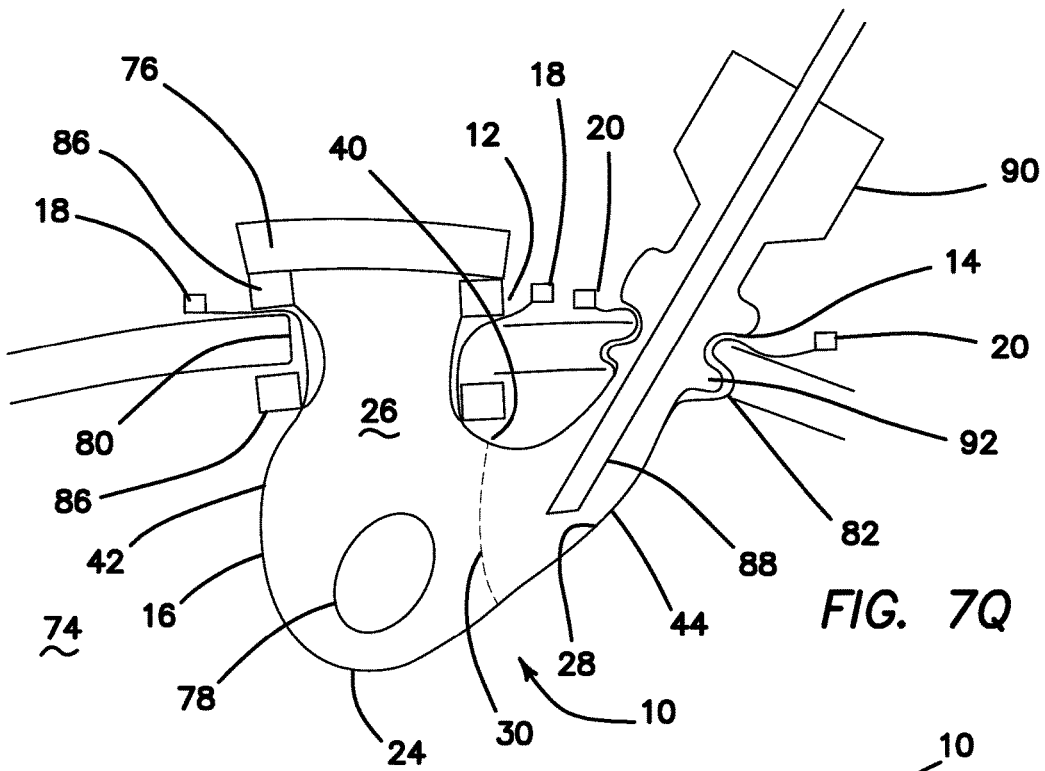
FIG. 7Q is a schematic of two retractors, a scope, trocar, tissue specimen, and containment bag inside a patient according to the present invention.
Figure 7R:
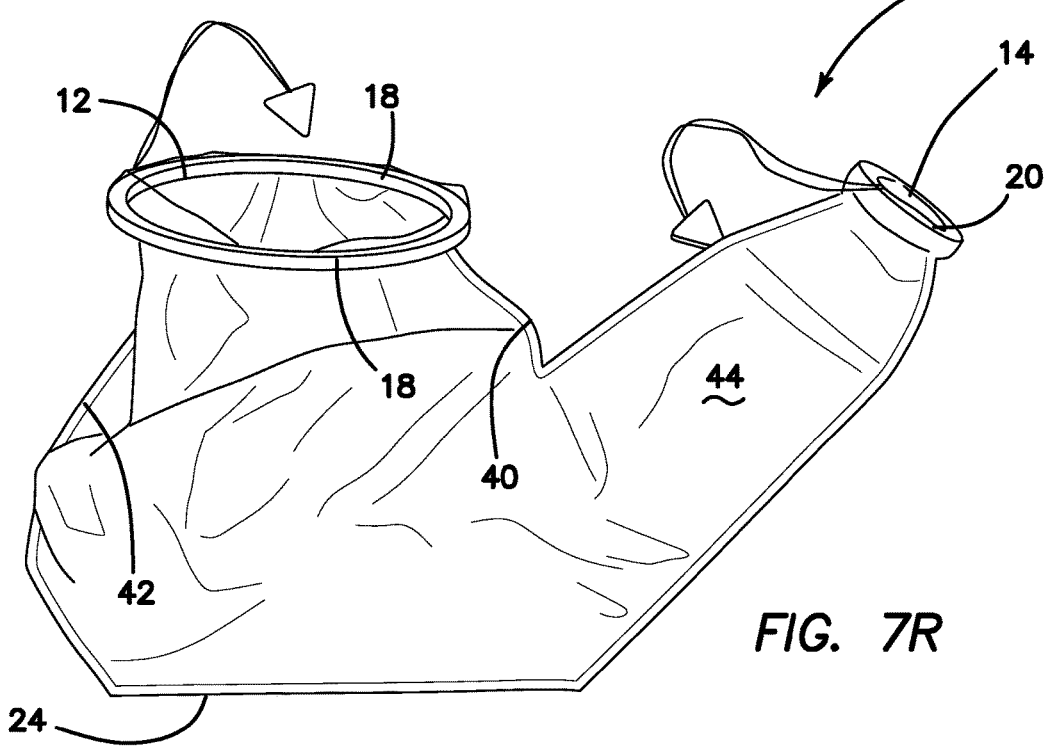
FIG. 7R is a top perspective view of a containment bag according to the present invention.

Turning now to FIGS. 7A-7R, there is shown a containment bag 10 according to the present invention. The containment bag 10 includes a first opening 12, also called a mouth, and a second opening 14 interconnected by a sidewall 16. A first ring 18 is provided at the first opening 12 and a second ring 20 is provided at the second opening 14. The rings 18, 20 are connected to the sidewall 16 by, for example, enclosing the rings 18, 20 in a pocket formed by the sidewall 16 heat sealed onto itself and/or with adhesive. The sidewall 16 is formed of any suitable flexible material including but not limited to fabric, polymer, polymer reinforced with fabric, mesh, nylon, fibers and the like. The first opening 12 is larger than the second opening 14. The sidewall 16 forms a teapot shape wherein the second opening 14 forms the opening at the spout or neck of the vessel. The sidewall 16 includes a base 24 configured for supporting a tissue specimen. Unlike the previous variations described above in which the first opening 12 and second opening 14 were substantially coaxial or otherwise described as being in alignment with each other along a longitudinal axis of the bag 10 when the bag 10 is laid flat or suspended in air in an undeflected orientation, in this variation, the first opening 12 and the second opening 14 are adjacent to each other or have longitudinal axes that are parallel or angled with respect to each other wherein the first ring 18 defines a first central longitudinal axis perpendicular to the radial plane of the ring 18 and/or opening 12 and the second ring 20 defines a second central longitudinal axis perpendicular to the radial plane of the ring 18 and/or opening 14. The openings 12, 14 are eccentric or nonconcentric. The base 24 defines a first side 40 and a second side 42 relative to the base and first opening 12. The second opening 14 is formed in the first side 40 of the bag 10. The first side 40 of the bag 10 may form an extension neck 44 of various sizes, shapes, lengths, and positional locations with respect to the side 40 and base 24. In FIG. 7A, the second opening 14 is slightly lower than the first opening 12 as measured from the base 24. In FIG. 7B, the second opening 14 is at approximately the same height from the base 24 as the first opening 12. In FIG. 7C, the second opening 14 is higher from the base 24 relative to the first opening 12 and also includes a narrower and longer neck extension 44 leading to the second opening 14 compared to a shorter neck extension 44 shown in FIGS. 7A, 7B and 7D. In FIG. 7E, the neck extension 44 is positioned at the bottom of the side 40 closer to the base 24. The angle of the neck extension 44 with respect to the base 24 in FIG. 7E is less than the angle of the neck extension 44 with respect to the base 24 in FIGS. 7A, 7B, 7C or 7D. In one such variation of FIG. 7E, one side of the neck extension 44 is contiguous with the base 24 forming a larger effective base. The angle of the neck extension 44 is substantially equal to the base 24 and the neck extension 44 is positioned a distance or height from the base 24. In FIG. 7F, the neck extension 44 is located in the middle of the side 40. In such a variation, the base 24 forms a larger bowl having wide sides for containing the specimen 16 and, advantageously, preventing movement of specimen into the neck extension 44. In FIG. 7G, the neck extension is located at the top of the side 40 near the first opening 12 and a greater distance from the base 24. Still referencing FIGS. 7A-7R, the size of the entryway 30 or intersection between with the neck extension 44 may vary. For example, in FIG. 7A, the entryway is larger than in FIG. 7B, similar to the difference in the entryway in FIGS. 7C and 7D. In FIG. 7F, the entryway 30 is very small and located between the first opening 12 and the base 24 or substantially midway along the first side 40. In FIG. 7E, the entryway 30 is near and contiguous with the base 24. In FIG. 7G, the entryway 30 is near the first opening 12.

Turning now to FIGS. 7H-7P, the various tethers/tags and their various configurations will now be described. Each bag 10 includes at least one of a first tether 36 and an optional tag associated with the first opening 12 and a second tether 38 with an optional tag associated with the second opening 14. Some figures in this description show no tether, one tether at the first opening, one tether at the second opening, or a tether at both of the first and second openings; however, the invention is not so limited and any number of tethers and combinations are within the scope of the present invention, regardless of whether a figure shows such a combination of various tether locations and tether exclusions or inclusions. A tether can include a string such as one made of nylon, a tab, a film, a tape, a lead or the like. A tag is attached to the proximal end of the string. The tag is a piece of plastic that facilitates locating and grasping the tether. The tether may or may not include a tag. Furthermore, the word "tether" may be interchanged with the word "tab" and vice versa. In FIG. 7B, a first tab 36 is shown at the second side 42 and a second tab 38 at the second opening 14. In one variation, the first tab 36 is connected to the first ring 18 and the second tab 38 is connected to the second ring 20.

In FIG. 7H, a first tab 36 is interconnected with a second tab 38 wherein the first tab 36 is located at the first opening 12 and exits at the first side 40 and the second tab 38 extends along the neck extension 44 and out at the second opening 14. In FIG. 7H, the first tab 36 and the second tab 38 are the same tab, the free ends of which extend out from the bag 10 and include tags as shown and may or may not be attached fixedly to their respective rings 18, 20. In another variation, the first tab 36 and the second tab 38 are formed with separate tabs. The one or more tabs are fixed relative to the bag 10 and/or respective ring 18, 20. Of course, as mentioned above, the tabs may be tabs, strings, tethers, film, tape, lead and the like. FIG. 7I shows an enlarged section of the second opening 14 of FIG. 7H, wherein the second tab 38 is wrapped around the second ring 20 before exiting at the second opening 14. The first tab 36 may also be similarly wrapped around the first ring 18. In a variation in which the first tab 36 and the second tab 38 are separate tabs, the first tab 36 may be connected to the first ring 18 and not extend along the first side 40 of the bag 10. In another variation in which the first tab 36 and the second tab 38 are separate tabs, the first tab 36 is fixed to the first ring 18 and or to the sidewall 16 and, if fixed to the sidewall 16 it may extend along the sidewall 16 by any distance. In one variation, the first tab 36 extends along the first side 40 of the sidewall 16 to approximately near the intersection of the sidewall 16 and the neck extension 44. This configuration is advantageous because when the first tab 36 is pulled, the sidewall 16 portion that is above the neck extension 44 is pulled upwardly bringing the bag 10 closer to the abdominal wall and will scrunch together that portion of the sidewall 16 above the neck extension 44 making removal of the bag 10 from the abdominal cavity easier. Also, the second tab 38 may also extend along only a portion the neck extension 44. The neck extension 44 is a distinct tubular, sleeve-like arm that branches from the main bag first compartment 26 and extends laterally outwardly from the sidewall 16 in a straight or angled orientation to interconnect the second opening 14 with the first compartment 26 via an intersection called an entryway 30 that is located between the first opening 12 and the second opening 14.

In FIG. 7J, the bag 10 includes a first tab 36 at the second side 42 exiting at the first opening 12 and a second tab 38 exiting the second opening 14. The second tab 38 extends along the bottom of the neck extension 44 and runs contiguously along the base 24 as shown and may or may not interconnect with the first tab 36.

In FIG. 7K, the bag 10 includes a first tab 36 at the first opening 12 and second side 42 adjacent and above the neck extension 44 and a second tab 38 at the second opening 14. The second tab 38 extends along the length of the neck extension 44 and upwardly along the first side 40 to the first opening 12 but does not exit at the first opening 12. Also, FIG. 7K illustrates a relatively large and deep specimen receiving portion in the lateral and vertical direction because the base 24 extends contiguously into the neck extension 44 at the first side 40. The first side 40 is shown in FIG. 7K to extend from the first opening 12 approximately one third of the length of the first side 40 wherein the specimen receiving portion rises approximately two thirds upwardly from the base 24 along the length of the first side 40. Having a large specimen receiving portion which is the case in variations in which the base 24 is contiguous with the neck extension 44 prevents twisting of the neck extension 44 because the neck extension 44 is smaller at the second opening 14 compared to the width of the neck extension 44 at an entryway 30 formed by the intersection of the neck extension 44 with the first side 40. Therefore, the neck extension 44 flares out or widens in diameter with distance towards the bag 10 and decreases in size or narrows in diameter with distance towards the second opening 14. A scope that is inserted in through the second opening 14 can land the distal end of the scope near the base 24 to observe that careful morcellation is proceeding without compromise to the bag walls. Also, a zero degree scope may be employed easily to observe morcellation taking place inside the bag. Referring back to FIG. 7F, there is shown a neck extension 44 that has approximately the same width or diameter at the second opening 14 as at the entryway 30 formed by the intersection of the neck extension 44 with the first side 40. The wider entryway 30 advantageously provides a larger specimen viewing and receiving location and also minimizes twisting of the neck extension 44 about itself.

Turning now to FIGS. 7L and 7M, the configuration of the tab with respect to the bag 10 will be described in greater detail wherein the neck extension 44 is shown for illustrative purposes and the same configuration may be applied to anywhere in the bag 10 where a tab is located including the sidewall 16, first side 40, and second side 42. The sidewall 16 will have a primary seam 46a, 46b formed along the edges of the bag. The primary seam 46a, 46b is formed by adhesive and/or hot sealing two sides of the bag sidewall 16 together. The primary seam 46a, 46b helps define the shape of the bag 10. A secondary seam 48 is shown adjacent to a primary seam 46a and spaced apart from the primary seam 46a to form a channel 50 for the tab 36, 38. Of course, in some areas of the bag 10, there may be no primary seam 46a, 46b, in which case, the secondary seam 48 is formed near the edge of the sidewall 16. The tab 36, 38 may be fixed within the channel 50 or may be free to translate within the channel 50. FIG. 7M illustrates the axis of the tab 38 which defines an axis of rotation about which the neck extension 44 would tend to rotate. The presence of a tab 38 at the neck extension 44 advantageously permits a rotated or twisted neck extension 20 to be quickly straightened by simply pulling the tether 38 at the proximal end where the tag is located. The tab 38 may be at anywhere around the neck extension 44. In one variation, the tab 38 is along at least a portion of top of the neck extension 44. This configuration advantageously permits the second tab 38 to be lifted by raising the tag at the end of the tab 38 and allowing the weight of the remainder of the neck extension 44 that is wrapped or tangled about itself along and around the longitudinal axis of the neck extension 44 to unfurl and unflip in a relatively downwardly direction to open the lumen of the neck extension 44. The unfurling or untangling of the neck extension 44 is preferably performed while the neck extension 44 is inside an insufflated patient cavity and before the second ring 20 is pulled into a position such as through an incision or body orifice such as the vagina. After the second ring 14 is resident outside the patient, untwisting the neck extension 44 becomes more difficult due to pressure from the adjacent tissue margin onto the neck extension 44. The tab 38 along at least a portion of the neck extension 44 greatly assists in quickly orienting and positioning the neck extension relative to the anatomy. Pulling or lifting the tab 38 untwists the neck extension 44 and prevents it from interfering with the scope when it is inserted and also when the scope is viewing specimen. The tab 36, 38 may be contrast colored against the rest of the bag sidewall so that the user can view the tab 36, 38 to discern if the position of the neck extension 44 is correct. For example, a user will see the colored tab 36, 38 and if it is oriented along a bottom end of the neck extension 44 or does not form a straight line, for example, the user will know that there is one or more twists in the neck extension 44 and that the tab 36, 38 needs to be pulled such that the tab 36, 38 is a straight line along the top of the neck extension 44. In lieu, of a tab 36, 38 serving as an indicator for the proper orientation of the bag 10, the bag 10 itself may be printed with indicator markers such as lines and arrows in contrast color to provide information to the user about the position of the bag 10 and/or neck extension 44.

Figure 24A:
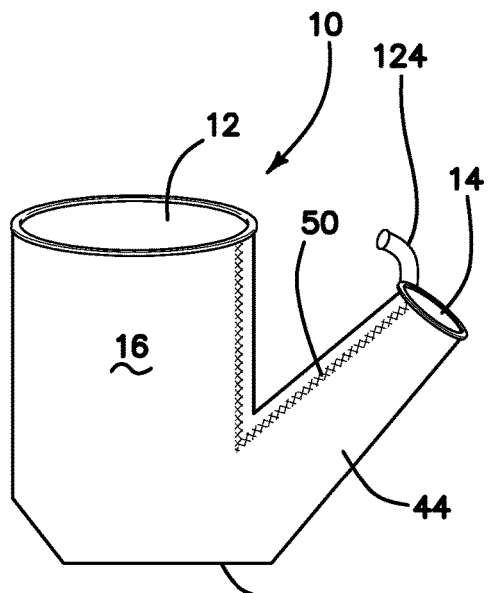
FIG. 24A is a top perspective view of a containment bag with a channel according to the present invention.
Figure 24B:
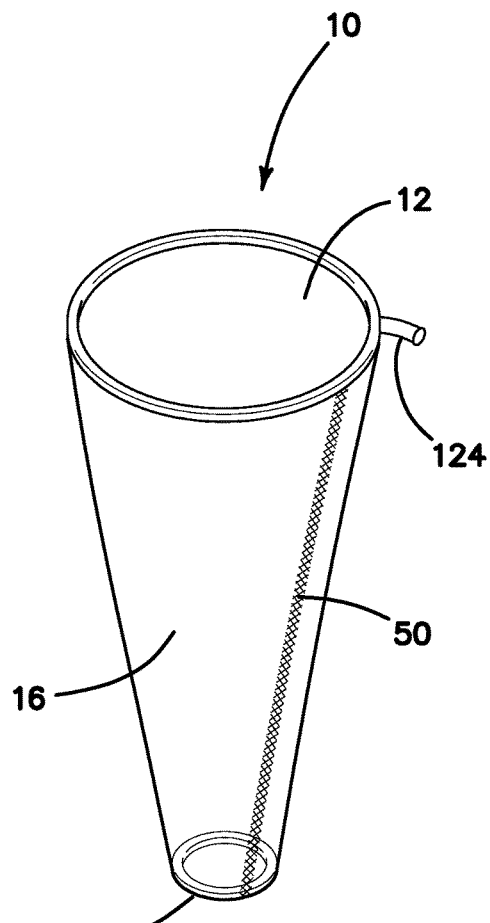
FIG. 24B is a top perspective view of a containment bag with a channel according to the present invention.
Figure 24C:
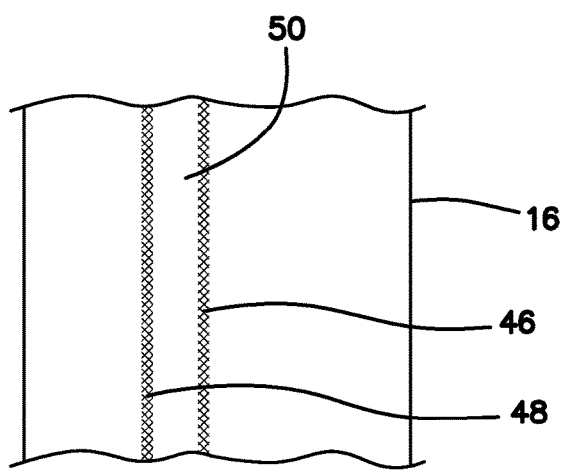
FIG. 24C is a sectional view of a containment bag with a channel according to the present invention.

In another variation, and with reference to FIGS. 24A, the channel 50 along the neck extension 44 can be connected to a source of insufflation fluid, which when delivered into the channel 50, unfurls the neck extension 44 into the proper orientation and direction. The channel 50 may extend only along the neck extension 44 or along the sidewall 16 of the bag 10. In FIG. 24A, the channel 50 is shown to extend along both the neck extension 44 and sidewall 16 to the first opening 12 from the second opening 14. The proximal end of the channel 50 can have a connector 124 configured for connection to the source of insufflation fluid and resident outside the patient, for example near the first opening 12 as shown in FIG. 24B or near the second opening 14 as shown in FIG. 24A. In both FIG. 24A and FIG. 24B, the channel 50 extends from the first opening 12 to the second opening 14. The channel 50 can be applied for any variation of bag 10 described herein and is not limited to the sleeve-like and two-headed bags as shown in FIGS. 24A and 25B. One or more channels 50 may be provided that are interconnected or separated. The channels 50 are shown to be straight but may also form a pattern suitable for insufflation or include a plurality of spaced apart rings around the neck extension 44 or other part of the bag 10. The channel 50 is formed by heat sealing a portion of the bag together, as described above, to form a primary seam 46 and a secondary seam 48 as shown in FIG. 24C. The channel 50 may also be a separate tube attached internally or externally to the bag 10.

In another variation, a connector 124 is provided at the proximal end of the bag at or near the first opening 12 that is configured to perform one or more of the following functions: insufflating the bag 10, insufflating a second bag 10, insufflating an inner bag, insufflating an outer bag, insufflating the abdominal cavity, and insufflating the channel 50. For example, as shown in FIG. 25, a Y-shaped connector 124 connected to a source of insufflation fluid can divert insufflation fluid into the interior of the bag 10 and into the abdominal cavity 74 outside the bag 10 via a trocar 90 or insufflation needle. An optional access port cap/platform 76 may be used to seal the first opening 12 and the connector 124 may be connected to the cap/platform 76 or to the bag 10 itself. Insufflation of both the bag 10 and abdominal cavity 74 creates an equal pressure. The bag 10 acts as a membrane and the organs in the abdominal cavity are advantageously moved away from the bag 10, thereby, protecting the organs from inadvertent morcellation. In another example, the connector 124 can be a three-way connector to direct insufflation fluid into the abdominal cavity 74, into the bag 10 and into the channel 50 to unfurl the neck extension 44. Another variation is shown in FIG. 26 in which the system includes a first bag 10 containing the specimen 78 and a second bag 11 that contains the first bag 10. The first bag 10 or inner bag 10 is located inside the second bag 11 or outer bag 11. A connector 124 is configured to deliver insufflation fluid to one or more of the first bag 10 and second bag 11. Preferably, both the first bag 10 and the second bag 11 are insufflated via the connector 124. An access port cap/platform 76 is provided to seal insufflation pressure within the first bag 10 and the connector 124 may be connected directly to the each bag 10, 11 or via the cap/platform 76 for delivery of insufflation fluid to the first bag 10 and directly to the second bag 11 for delivery of insufflation fluid to the second bag 11. The connector 124 in FIG. 126 may be a three-way connector 124 and further deliver insufflation fluid into the abdominal cavity 74. The double-bag system of FIG. 26 advantageously provides added protection in the event the inner bag 10 is accidentally punctured with surgical instruments. In such an event, containment of the specimen would not be breached as the outer bag 11 would retain the specimen in a closed system.

Turning now to FIGS. 7N-7P, there is shown more detail of the tether/tab configuration at either the first opening 12 or the second opening 14 or both. For illustrative purposes, the second opening 14 and a section of the neck extension 44 is shown in FIG. 7N. The tab 38 extends inside a channel 50 and exits at the second opening 14. Placement of the tab 38 inside the channel 50 is for exemplary purposes and the tab may be integrally formed with the bag. In FIG. 7O, the detail of the second ring 20 is shown for illustrative purposes and the same configuration may be applied to the first ring 18 at the first opening 12. In FIG. 7O, the tether 38 is tied or wrapped around the second ring 20. A knot may also be formed. In FIG. 7P, the tether 38 is looped around the second ring 20 multiple times forming multiple windings before exiting at the second opening 14. A knot may also be formed in the variation of FIG. 7P to secure the tether 38 to the second ring 20. The tether may be attached anywhere along the ring and/or bag and the same may be applied to the first opening 12. FIG. 7Q illustrates the bag 10 of FIGS. 7A-7R in use which will be described in greater detail below. FIG. 7R illustrates a containment bag 10 as described herein according to the present invention.

Figure 8A:
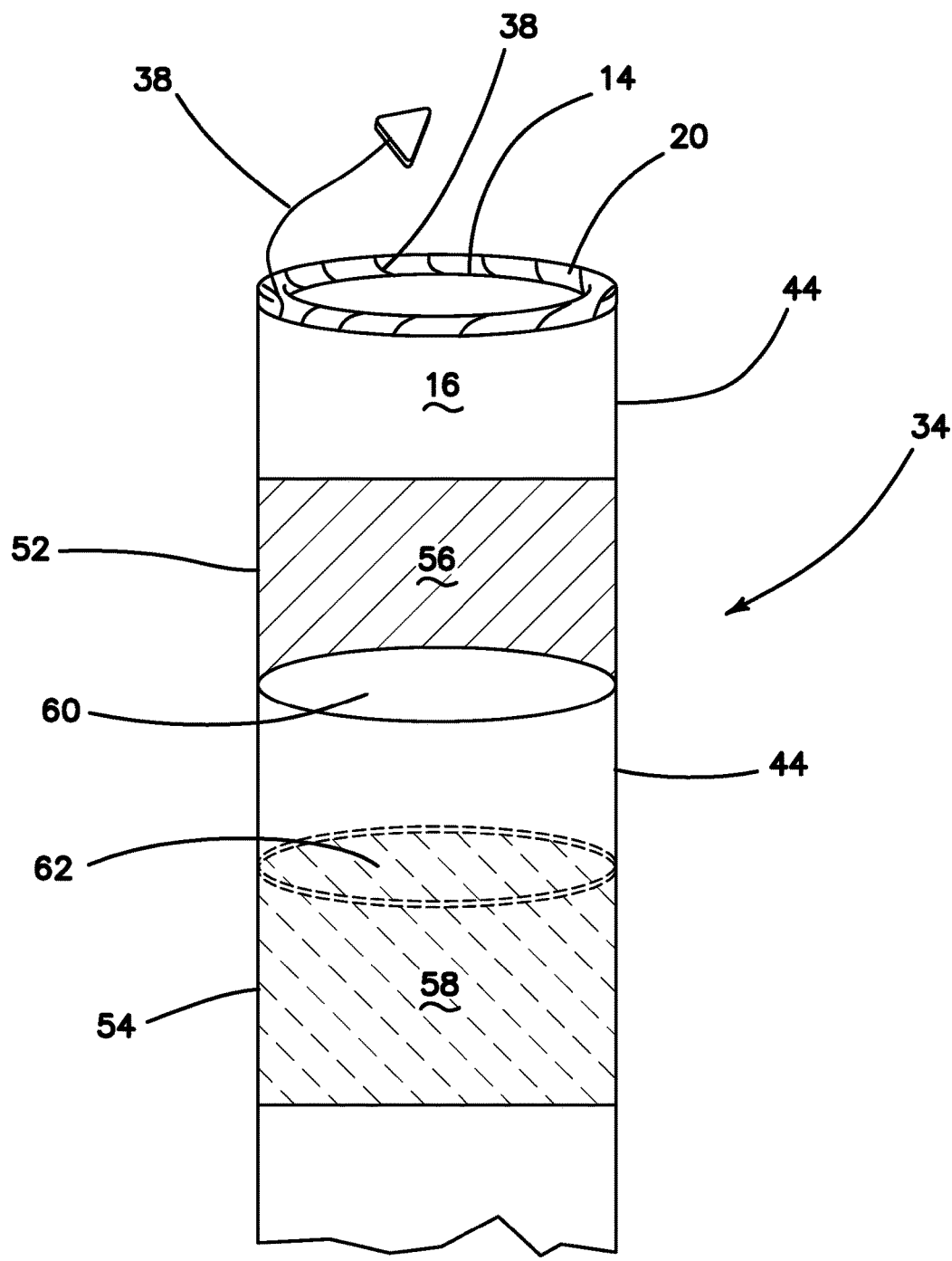
FIG. 8A is a sectional view of a containment bag according to the present invention.

Turning now to FIG. 8A, the seal mechanism 34 applicable to the neck extension 44 or second compartment 28 will be described in greater detail. The seal mechanism 34 is configured to seal off the second opening 14 of any bag variation shown herein. When the morcellation is completed and the bag 10 is ready for removal, it will be removed from either an incision in the abdominal wall such as at the umbilicus or it will be removed through the vaginal opening or other orifice. As such, the bag 10 will be pulled out at one end; hence, the opposite end must be sealed off to maintain a closed system and prevent specimen from spilling out. The seal mechanism 34 will be described with respect to the second opening 14 as that is preferred location for the seal mechanism 34. The seal mechanism 34 includes a first pocket 52 and a second pocket 54. The first pocket 52 is located on one side of the bag 10 and the second pocket 54 is generally located on the opposite side of the bag 10; however, the invention is not so limited. The first pocket 52 is formed by attaching a first patch 56 to the outer surface of the sidewall 16. The first patch 56 is attached with adhesive or by heat sealing the first patch 56 to the sidewall 16. In one variation, the first patch 52 is attached along three sides of its perimeter leaving one side of the perimeter detached and serving as part of the mouth to the first pocket 52. The first patch 52 is shown with cross hatch marks in FIG. 8A. The second pocket 54 is formed by attaching a second patch 58 to the outer surface of the sidewall 16 on the opposite side of the first patch 56. The second patch 58 is attached with adhesive or by heat sealing the second patch 58 to the sidewall 16. In one variation, the second patch 58 is attached along three sides of its perimeter leaving one side of the perimeter detached and serving as part of the mouth to the second pocket 54. The second patch 58 is shown with dashed hatch marks in FIG. 8A. The mouth 60 of the first pocket 52 faces distally away from the second opening 14 and the mouth 62 of the second pocket 54 faces proximally toward the second opening 14. Therefore, the pocket openings 60, 62 face each other. Also, the pocket openings 60, 62 are aligned longitudinally along the with the second opening 14 such that the first pocket 52 is distally located from the second opening 14 and the second pocket 54 is distally located from the first pocket 52.

Figure 8B:
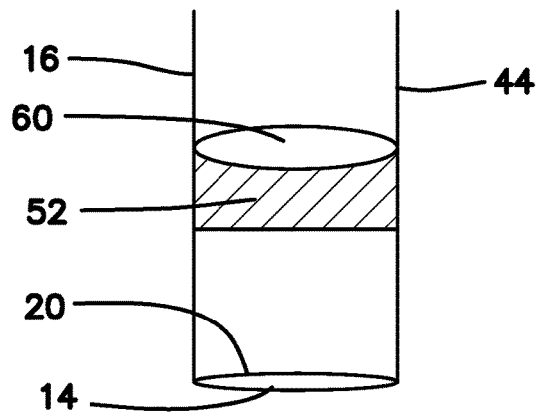
FIG. 8B is a sectional view of a containment bag according to the present invention.
Figure 8C:
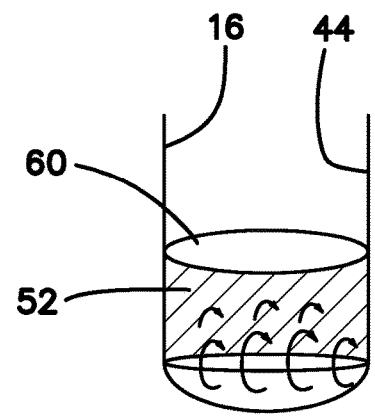
FIG. 8C is a sectional view of a containment bag with a portion of the containment bag rolled according to the present invention.
Figure 8D:
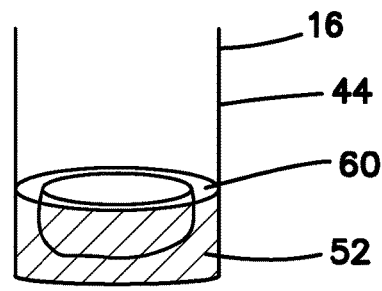
FIG. 8D is a sectional view of a containment bag with a portion of the containment bag rolled and inserted into a first pocket according to the present invention.
Figure 8E:
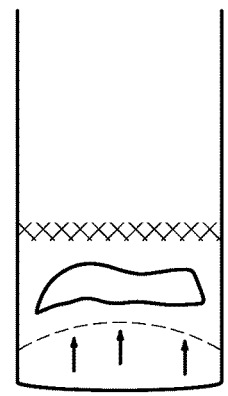
FIG. 8E is a sectional view of a containment bag with a portion of the containment bag rolled and inserted into a first pocket and a second pocket according to the present invention.

In use and with reference to FIGS. 8B-8E, the resilient second ring 20 is squeezed into a low-profile configuration as shown in FIG. 8B. The second ring 20 is rolled distally such that the sidewall 16 of the neck extension 44 is rolled onto the second ring 20 all the way over the first pocket 52 to the distally facing first mouth 60 as shown in FIG. 8C. The rolled up neck extension 44 is inserted into the first pocket 52 as shown in FIG. 8D. Then the first pocket 52 with contents is folded over towards the back side and the first pocket 52 is inserted/tucked into the second pocket 54 as shown in FIG. 8E. The first pocket 52 is inserted into the second pocket 54 such that the second pocket 54 encompasses the first pocket 52 and its contents. The tucking of the first pocket 52 into the second pocket 54 advantageously prevents the rolled bag from snagging onto anything during post morcellation bag retrieval. This configuration of the bag 10 and method advantageously seals the contents including fluids inside the bag 10 and prevents them from escaping through the second opening 14 during bag 10 removal. The resilient second ring 20 when squeezed is biased to expand to its enlarged high-profile configuration. Advantageously, such resiliency of the second ring 20 biases the second ring 20 together with the sidewall 16 rolled onto it towards the inside walls of the first pocket 52. The resiliency of the second ring 20 creates a locking feature and sealing effect as the second ring 20 tends outwardly and pushes portions of the sidewall 16 against adjacent portions of the rolled-up sidewall 16. Hence, rolling of the bag 10 and the resilient second ring 20 creates a seal.

Figure 9:
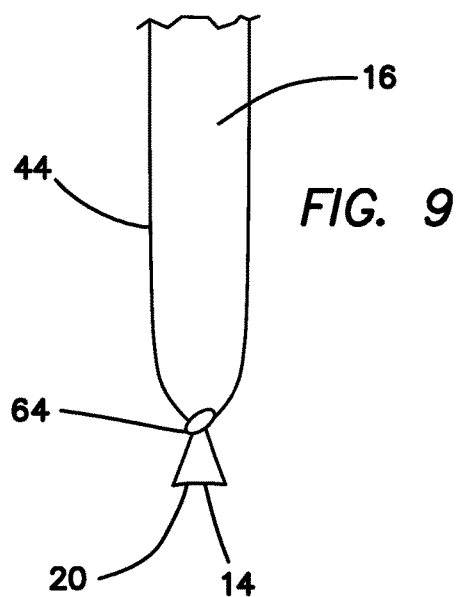
FIG. 9 is a sectional view of a containment bag with a tied end according to the present invention.
Figure 10:
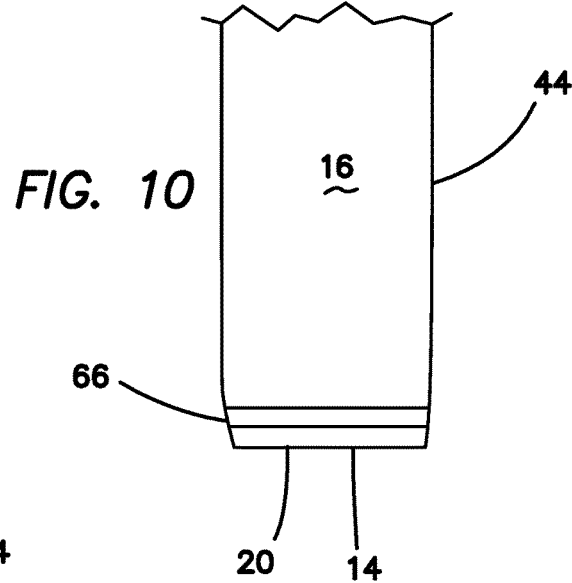
FIG. 10 is a sectional view of a containment bag with a sealed end according to the present invention.
Figure 11:
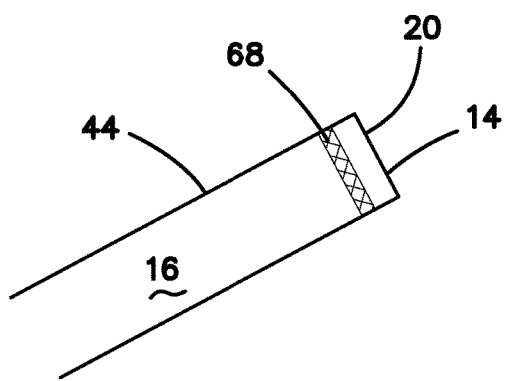
FIG. 11 is a sectional view of a containment bag having an interlocking releasable seal at one end according to the present invention.
Figure 12:
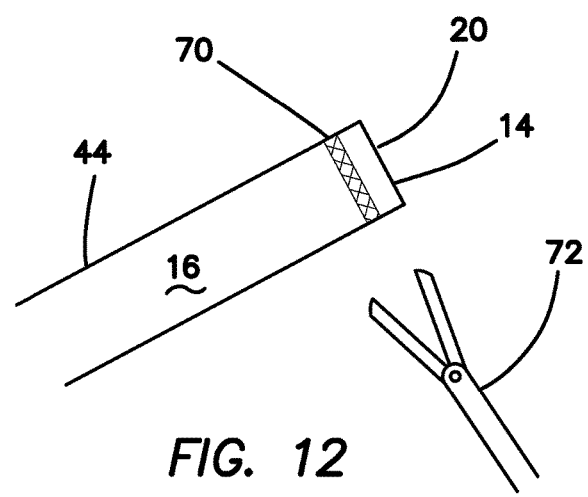
FIG. 12 is a sectional view of a containment bag configured to be heat sealed and sectional view of an instrument used to heat-seal the containment bag according to the present invention.

Other constructions and methods for sealing the second opening 20 will now be described. Turning now to FIG. 9, there is shown another method for sealing the second opening 14 of the containment bag 10 in which a knot 64 is tied at the distal end. In another variation, the distal end of the bag 10 is provided with double-sided tape 66 which seals the second opening 14 at a distance proximal to the second ring 20 as shown in FIG. 10. Turning to FIG. 11, an interlocking ridge and groove 68 is provided in which the groove is formed on one inner surface of the sidewall 16 and the ridge is formed on an opposite inner surface of the sidewall 16. The ridge is configured to interlock with the groove when pressed together by a user's fingers or by employing a zipper. In FIG. 12, a seal 70 is created by employing a bipolar instrument 72 to deliver electrical current or heat to heat seal or melt the opposite sidewalls 16 at the neck extension 44 together to seal the bag 10. In such a variation, the bag 10 is made of suitable material such as thermoplastic and the instrument 72 is set so as to not burn or melt the bag 10 too much.

Figure 22:
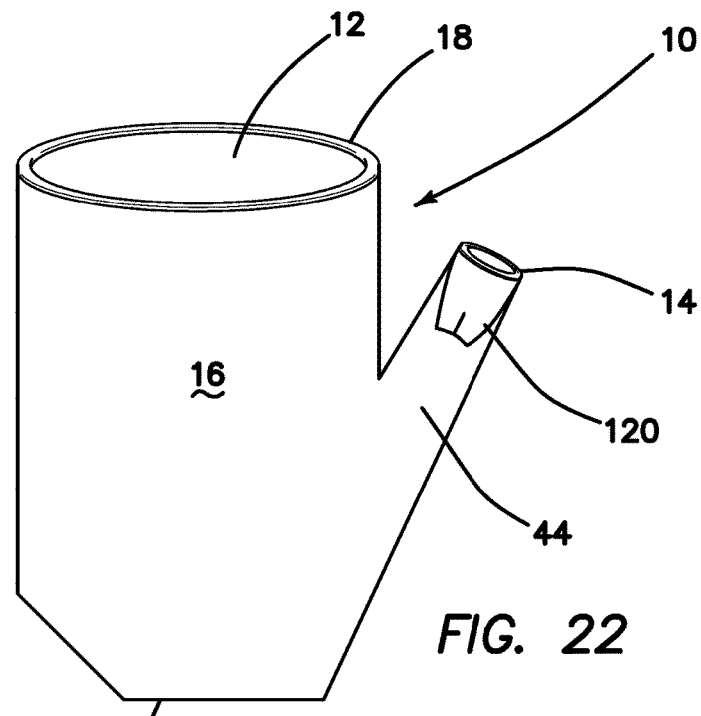
FIG. 22 is a top perspective view of a seal at an opening of a containment bag according to the present invention.
Figure 23:
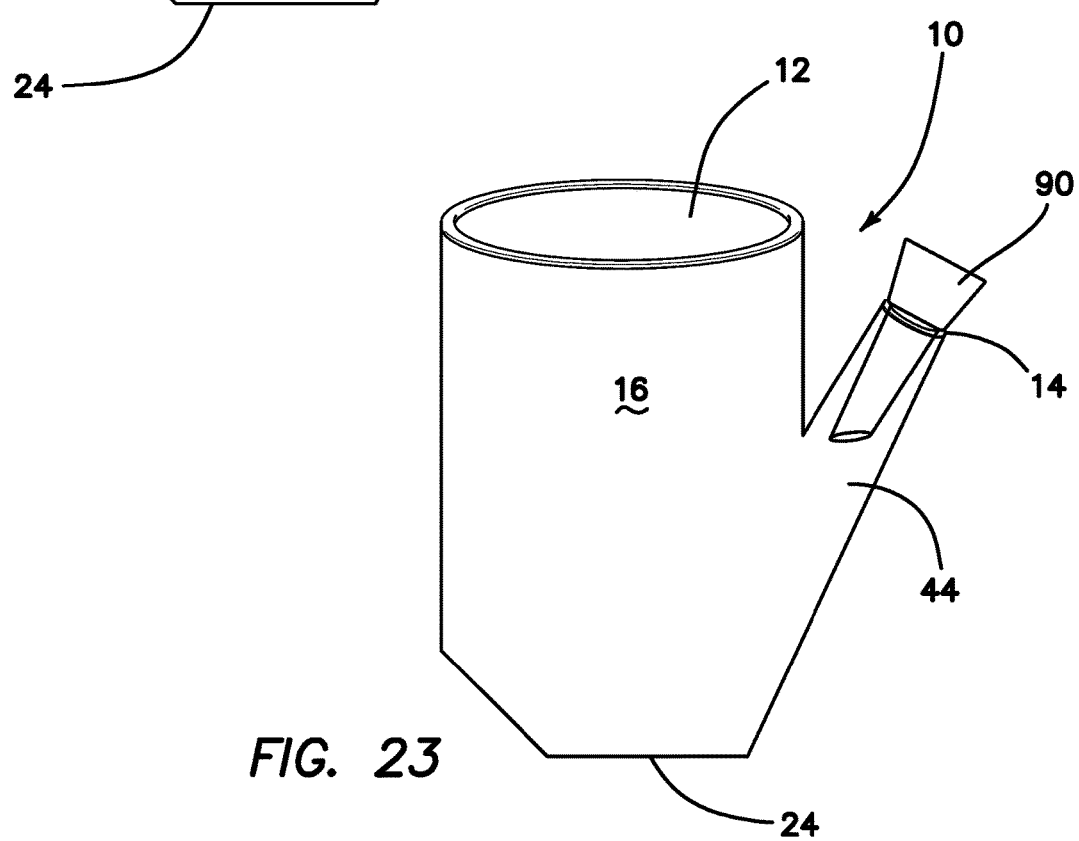
FIG. 23 is a top perspective view of a trocar at an opening of a containment bag according to the present invention.

In use, after the uterus has been detached as described above, the insertion and removal of a containment bag 10 of the like described with respect to FIGS. 7-12 will now be described. Aspects of this method may also apply to any bag variation described herein. The containment bags 10 of FIGS. 7A-7R will be referred to as dual-head bags 10 for ease of reference and to differentiate from the tube-like bags of FIGS. 1-6. Firstly, any trocar is removed from the umbilical incision. Any one of the dual-head bags 10 of FIGS. 7A-7R is inserted through the umbilical incision and the trocar is re-inserted. The trocar may be inserted directly into the umbilical incision or through an access port cap/ platform connected to a retractor placed in the incision. Referring back to FIG. 7Q, the abdominal cavity is re-insufflated via the access port cap/platform 76 or through the trocar in order to provide a better view for positioning the bag 10. A scope is inserted through the umbilical incision 80 and the detached uterus 78 is inserted into the bag 10 with graspers. A second incision 82 is made through the abdominal body wall 84 in a location medial-to-lateral of the umbilicus. A surgical grasper is inserted through the second incision 82 and the tether at the second opening 14 is grasped and pulled through the second incision 82 pulling the neck extension 44 towards the abdominal body wall 84. The smaller second ring 20 is pulled through the second incision 82. In one variation, if the neck extension 44 is sufficiently long, the second ring 20 can be pulled through the vaginal canal and opening. The tether attached to the larger first ring 18 is pulled toward the umbilical incision. As the first opening 12 of the bag 10 is drawn towards the abdominal body wall 84, the trocar and/or the access port cap/platform 76 are removed and the first ring 18 and a proximal portion of the bag 10 is pulled through the umbilical incision. If a retractor 86 is in position at the umbilical incision, the retractor 86 may be removed before the first ring 18 is pulled through. If the retractor 86 is removed, the first ring 18 is brought to the surface of the abdominal body wall 84 and the retractor 86 is inserted into the first opening 12 of the bag 10. The adjacent tissue and the bag 10 in the location of the umbilical incision 80 is retracted with the retractor 86 as shown in FIG. 7Q. The access port cap/ platform 76 is then connected to the retractor 86 by snapping the access port cap/platform 76 under or over the first ring of the retractor 86. The bag 10 is held firmly in place between the retractor 86 and tissue wall 84 at the umbilical incision. If the retractor 86 is not removed, the bag 10 is pulled through the lumen of the retractor 86 and laid over the first ring of the retractor outside the abdominal wall. The access port cap/platform 76 is re-attached by snapping the access port cap/platform 76 either under/over the first ring 18 of the bag 10 or the first ring of the retractor 86. If the access port cap/platform 76 is snapped under/over the first ring of the retractor 86, the bag sidewall 16 will be captured between the retractor 86 and the access port cap/platform 76 holding it in position. If the retractor 86 is not be used at all, in which case, the bag 10 is inserted into the umbilical incision 80 or if a retractor 86 is used initially to insert the dual-head bag 10, it may not be re-inserted into the bag 10 at the first opening 12 as described above. In such a situation, the first ring 18 of the bag 10 is pulled through the umbilical incision 80 and overlaid onto the abdominal body wall 84. The access port cap/platform 76 is attached directly to the first ring 18 of the dual-head bag 10. A morcellator is inserted into the dual-head bag 10 through the first opening 12 and a scope 88 is inserted through the second opening 14 and into the neck extension 44 towards the entryway 30 to the first compartment 26. The scope 88 may be inserted directly into the dual-head bag 10 or through a trocar 90 placed inside the second opening 14 as shown in FIG. 7Q. FIG. 20 also illustrates in greater detail a trocar 90 inserted into the second opening 14 of the bag 10. The bag 10 is pulled through an incision that is small enough to fit a trocar 90 such that the bag sidewall 16 is sealed against the tissue margin 45 by the trocar 90 so that insufflation gas does not escape from the abdominal cavity 74 as shown in FIG. 20. FIG. 23 illustrates a trocar 90 configured to be removably and sealingly attached at the second opening 14. In FIG. 23, an attachment feature at the end of the neck extension 44 sealingly snaps and locks onto the trocar 90 to maintain a pressure and prevent insufflation fluid from escaping from inside the bag 10 or inside the abdominal cavity 74. Alternatively, as shown in FIG. 21, at least a proximal portion of the neck extension 44 along with the second ring 20, if one is employed, is pulled through the cannula lumen of the trocar 90. In this manner, a seal against the tissue margin 45 is provided by the trocar 90 being inserted into an incision that is equally sized or smaller than the outer diameter of the trocar 90 to prevent the escape of insufflation gases inside the abdominal cavity 74. In one variation, the trocar 90 is provided with a balloon 92 which retracts the tissue along with the sidewall 16 of the bag 10 located in the second incision 82. Alternatively, an access port cap/platform may be attached to the second ring 20 and the scope 88 inserted through the access port cap/platform with or without a trocar 90. In another variation, at least one seal 120 is provided at the second opening 14 as shown in FIG. 22. The seal 120 may be removably fitted with the second opening such as in a snap-fit or twist-and-lock configuration. More than one seal can also be provided in a seal assembly fitted and connected the second opening 14. The seal assembly may include a zero seal that prevents escape of gas and fluid across the seal when no instrument is inserted through the zero seal. The zero seal may be a double duckbill type valve or other valve. The seal assembly may further include an instrument seal that seals against an inserted instrument to prevent escape of fluid and gas across the seal. Also, a seal shield may be provided to protect the seal from being damaged due to impingement with an instrument. The morcellation of the uterus 78 is commenced while under unobstructed observation via the scope 88. After morcellation is completed, the morcellator, the scope 88 and trocar 90 (if used) are removed from the second opening 14. The neck extension 44 is sealed by closing the second opening 14 according to any one of the methods described above to prevent any particles of specimen or fluid remaining inside the bag from escaping the bag 10 during the removal of the bag 10 from the patient. The second ring 20 of the bag 10 is inserted into the abdominal cavity 74 through the second incision 82. In one variation, the neck extension 44 is rolled up and tucked into the first and second pockets 52, 54 or, alternatively, the neck extension 44 is tied into a knot 64. Any access port cap/platform 76 and/or retractor 86 at the umbilical incision 80 are removed and the dual-head bag 10 is removed out of the body cavity 74 through the umbilical incision 80. This same procedure may be employed for the tube-like bags 10 throughout the specification such as those shown in FIGS. 1-6. The containment bag 10 and methods effectively create a contained morcellation system wherein morcellation, either manual or power, is carried out inside a closed system provided by the containment bag 10 and its placement within the anatomy. The openings to the bag 10 are sealed and the procedure carefully performed to prevent inadvertent scattering of tissue throughout the abdominal cavity. The containment bag 10 advantageously also provides a portal into the bag via the neck extension or second opening through which a scope can be inserted to further monitor the morcellation procedure making sure that the bag integrity is not broken during the process. This provides to the surgeon an extra safety precaution with direct observation of the surgical morcellation field while maintaining a closed system. The angle of observation via the neck extension or second opening provides the viewer a clear and lateral view of both the bag and the specimen and their position with respect to morcellation instruments throughout the morcellation. Also, the systems and variations of the present invention provide an easy way to deploy the bag internally into position.

After a uterus is detached laparoscopically, a bag 10 is inserted into the abdominal cavity 74 either vaginally or abdominally. At the point of bag insertion, pneumoperitoneum may be lost. After the bag is inserted, pneumoperitoneum is re-established. The detached uterus is placed inside the bag 10 and the bag 10 is laparoscopically manipulated to pull the bag openings through the desired locations which may include any one or more of the following locations: umbilicus incision, abdominal incision, lateral incision and vaginal opening. The tether/tab is pulled and a trocar is placed into the second opening 14 or the second opening 14 is capped with an access platform or port or the second opening 14 is pulled through the lumen of the trocar 90. All the bag openings are then closed and sealed and insufflation is introduced into the bag and/or abdominal cavity. The specimen inside the bag is then morcellated. Morcellation may be carried out using power or manual morcellation methods and instruments. The second opening 14 and other bag port openings are sealed off except for one opening, such as the first opening 12, that will be pulled to remove the bag such as through the incision at the umbilicus. The bag port openings are sealed to prevent any specimen from escaping containment inside the bag 10 as the bag is being removed. The bag is removed by being pulled through the abdominal incision such as an incision at the umbilicus. Additional variations of the invention will now be described for which the methods and features described above can be applied in whole or in part to the variations that follow and vice versa.

Figures 13, 15:
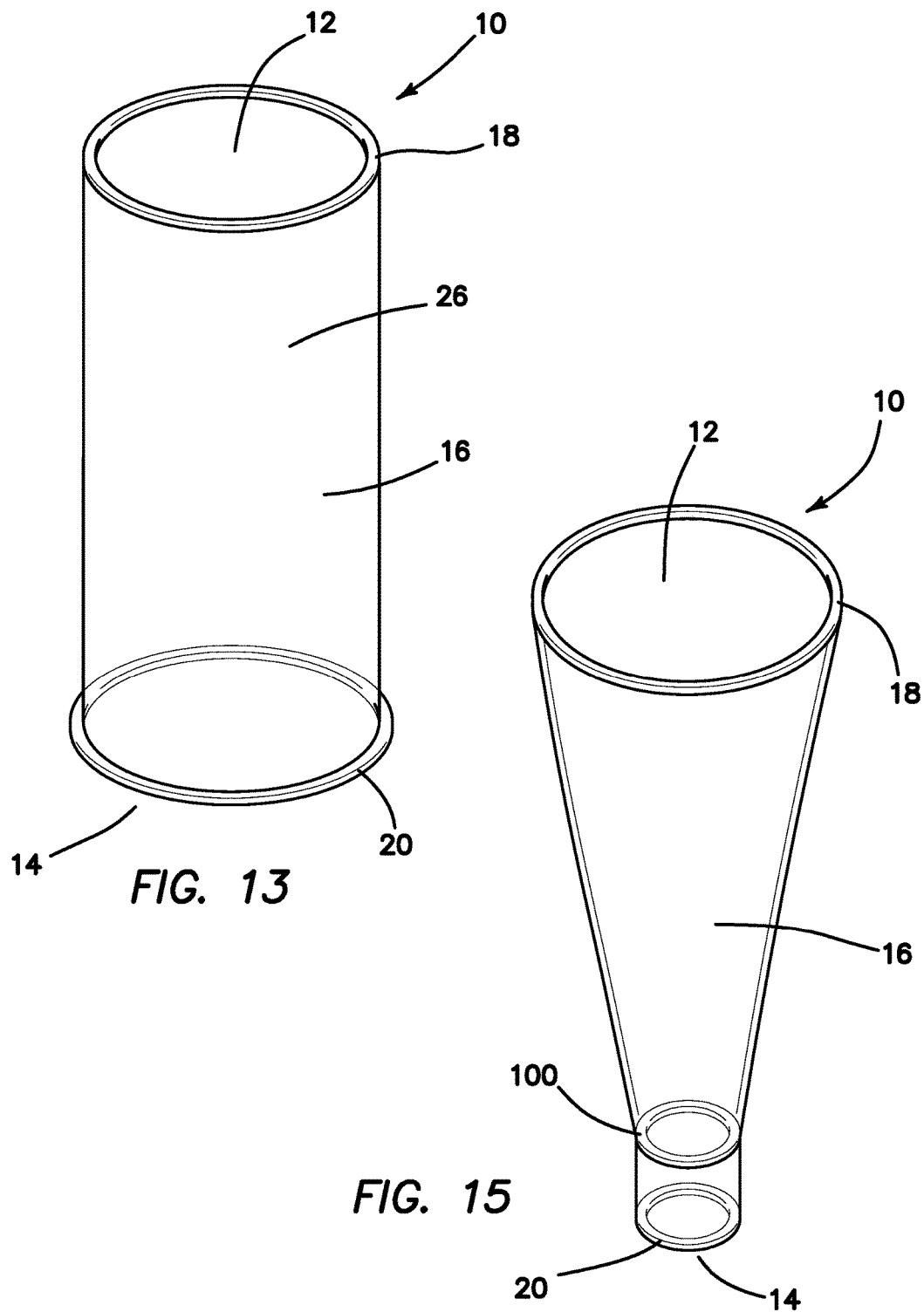
FIG. 13 is a top perspective view of a containment bag according to the present invention.
FIG. 15 is a top perspective view of a containment bag having two rings at one end according to the present invention.

Turning now to FIG. 13, there is shown a containment bag 10 according to the present invention wherein like parts are referenced with like numerals. The containment bag 10 includes a first opening 12, also called a mouth, and a second opening 14 interconnected by a sidewall 16. A first ring 18 is provided at the first opening 12 and a second ring 20 is provided at the second opening 14. The first ring 18 and the second ring 20 have substantially the same diameters. The rings 18, 20 are resilient and capable of deflection into a low-profile configuration for insertion through ports/incisions having diameters that smaller than the rings 18, 20. The sidewall 16 of the bag 10 has a substantially cylindrical tube-like shape having a constant diameter that is substantially the same diameter as the rings 18, 20. The sidewall 16 defines a central lumen that can also be called a first compartment 26 between the first opening 12 and the second opening 14. The bag 10 of FIG. 13 is bi-directional compared to the bag 10, for example, of FIG. 1A wherein the smaller second opening 14 seats more readily within and at the vaginal opening or other orifice than a bag with a larger second opening 14. However, if any one of the openings 12, 14 is too small it will be difficult to insert the specimen into the bag 10.

Turning now to FIGS. 14A-14C, a method of using a containment bag 10 according to the present invention will be described. In one variation, a tube-like sleeve bag 10 such as shown in FIGS. 1-6 and 13 is provided. A tissue specimen 78, such as a uterus, is detached and the bag 10 is inserted through an abdominal incision or orifice into a body cavity. The bag 10 is placed such that the first ring 18 is resident outside the patient at the location of the abdomen or orifice. A surgical instrument 94, such as surgical graspers, is inserted into the first opening 12 of the bag 10 and into the lumen of the bag 10. The specimen 78 is grabbed and pulled through the second opening 14 of the bag 10 into the lumen of the bag 10 as shown in FIG. 14A. The proximal end of the instrument 94 is manipulated outside the patient to open and close the jaws of the grasper at the distal end of the instrument. The specimen 78 is released inside the lumen compartment 26 as shown in FIG. 14B. The instrument 94 is then moved distally past the specimen 78 to grab the second ring 20 of the bag 10. The second ring 20 is grasped by the graspers 94 and pulled proximally into the lumen compartment 26 as shown in FIG. 14B. The second ring 20 is pulled along inside the lumen of the bag 26 proximally past the specimen 78 as shown in FIG. 14C and to the surface outside the patient creating a fold in the sidewall 16 inwardly into the lumen of the bag 10. After being pulled outside the patient, the second ring 20 can then be placed to the side of the first ring 18. The one or more fold divides the bag 10 and creates within the bag 10 a first pouch 96 that contains the specimen 78 and a second pouch 98 adjacent to the first pouch 96. The bag 10 is invaginated, inverted, turned or, otherwise, folded back into itself up the lumen toward the first ring 18 to form the pockets 96, 98. This action also advantageously pulls the specimen 78 closer to the first ring 18 where the specimen 78 can be more readily visualized and morcellated. To assist the morcellation, a scope (not shown) may be inserted into the second pouch 98 to observe the specimen 78 located in the first pouch 96 across the sidewall 16. Alternatively, a scope is inserted into the second opening 14 of the bag 10 and into the abdominal cavity and the specimen 78 is observed outside the first pouch 96. In another variation of the method, after the uterus is detached, the bag 10 may be inserted through the vaginal opening and the bag 10 positioned such that the first ring 18 is located outside the patient at the vagina. This method and bag 10 can be employed with any specimen, orifice or incision and is not limited to the uterus, vaginal opening and abdominal incision. Of course, the bag can be placed into any incision or orifice and pulled from any incision or orifice including the same incision or secondary incision.

Turning now to FIG. 15 there is shown a containment bag 10 according to the present invention wherein like parts are referenced with like numerals. The containment bag 10 includes a first opening 12, also called a mouth, and a second opening 14 interconnected by a sidewall 16. A first ring 18 is provided at the first opening 12 and a second ring 20 is provided at the second opening 14. Either one or more of the first end and the second end of the bag 10 includes a third ring 100 located near the first ring 18 or the second ring 20, respectively. For example, in FIG. 15, a third ring 100 is located near the second end of the bag 10 near the second ring 20. The second ring 20 is located at the distal second end of the bag 10 and the third ring 100 is spaced proximally from the distal second end by a distance configured for retraction purposes. Together with the second ring 20, the third ring 100 forms a retractor built-in with the bag 10. When positioned within the anatomy as described above, the second ring 20 will reside outside the patient such as outside the vaginal opening while the third ring 100 will reside inside the patient. The second ring 20 is resilient and capable of being flipped about itself to wrap the intermediate sidewall located between the second ring 20 and the third ring 100 around the second ring 20, thereby, retracting a tissue margin at the orifice, or incision to facilitate removal of a specimen placed inside the bag 10. The bag 10 of FIG. 15 is shown to have a frusto-conical shape; however, the employment of a third ring 100 is not limited to a bag 10 having this shape and can be used in any of the bag 10 variations described herein including the two-headed variations. Of course, in an alternate variation, the third ring 100 may be position near the first ring 18 and configured to serve the same built in retraction function. In another variation, a fourth ring (not shown) is provided adjacent to the first ring 18 and a third ring 100 is located near the second ring 20 such that retraction of tissue can take place at both ends of the bag 10.

Figure 16:
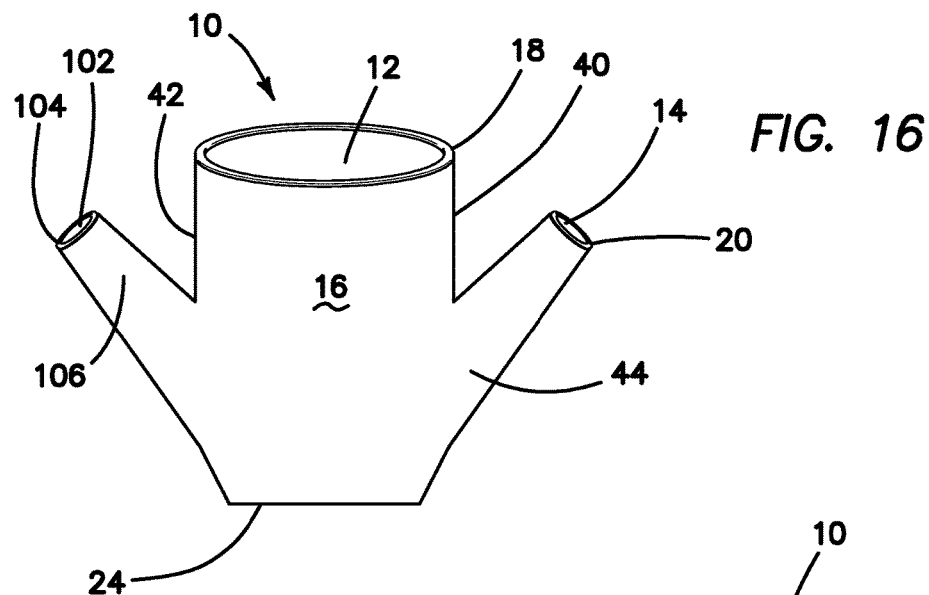
FIG. 16 is a top perspective view of a containment bag having three openings according to the present invention.

Turning now to FIG. 16, there is shown another containment bag 10 variation according to the present invention wherein like reference numbers are used to describe like parts. The bag 10 of FIG. 16 is similar to the teapot-like containment bag configurations of FIGS. 7A-7R having a neck extension 44. The bag 10 includes a first opening 12 and a second opening 14 interconnected by a sidewall 16. A first ring 18 is provided at the first opening 12 and a second ring 20 is provided at the second opening 14. The bag 10 further includes a third opening 102 and a third ring 104 at the third opening 102. The sidewall 16 includes a base 24 configured for supporting a tissue specimen. The first opening 12, second opening 14 and third opening 102 are adjacent to each other or have longitudinal axes that are angled with respect to each other wherein the first ring 18 defines a first central longitudinal axis perpendicular to the radial plane of the ring 18 and/or opening 12, the second ring 20 defines a second central longitudinal axis perpendicular to the radial plane of the ring 18 and/or opening 14 and the third ring 104 defines a third central longitudinal axis perpendicular to the radial plane of the ring 104 and/or opening 102. The openings 12, 14, 104 are eccentric. The base 24 defines a first side 40 and a second side 42 relative to the base 24 and first opening 12. The second opening 14 is formed in the first side 40 of the bag 10 and the third opening 102 is formed in the second side of the bag 10. The first side 40 of the bag 10 may form an extension neck 44 of various sizes, shapes, lengths, and positional locations with respect to the side 40 and base 24 interconnecting the first opening 12 with the second opening 14 and the second side 42 of the bag 10 may form a neck extension 106 of various sizes, shapes, lengths and positional locations with respect to the side 42 and base 24 interconnecting the first opening 12 with the third opening 102 and, of course, to the interior of the bag 10. In use, the bag 10 of FIG. 16 is positioned with respect to the anatomy such that the first opening 12 is at the abdomen such as inserted through an umbilical incision and resident with the first ring 18 outside the patient. The second opening 14 serves as a lateral port positioned at a lateral incision in the abdomen or at a lateral orifice such as the vagina with the second opening 14 and second ring 20 residing outside the patient. The third opening 102 also serves as a lateral port positioned at a lateral incision in the abdomen.

Figure 17:
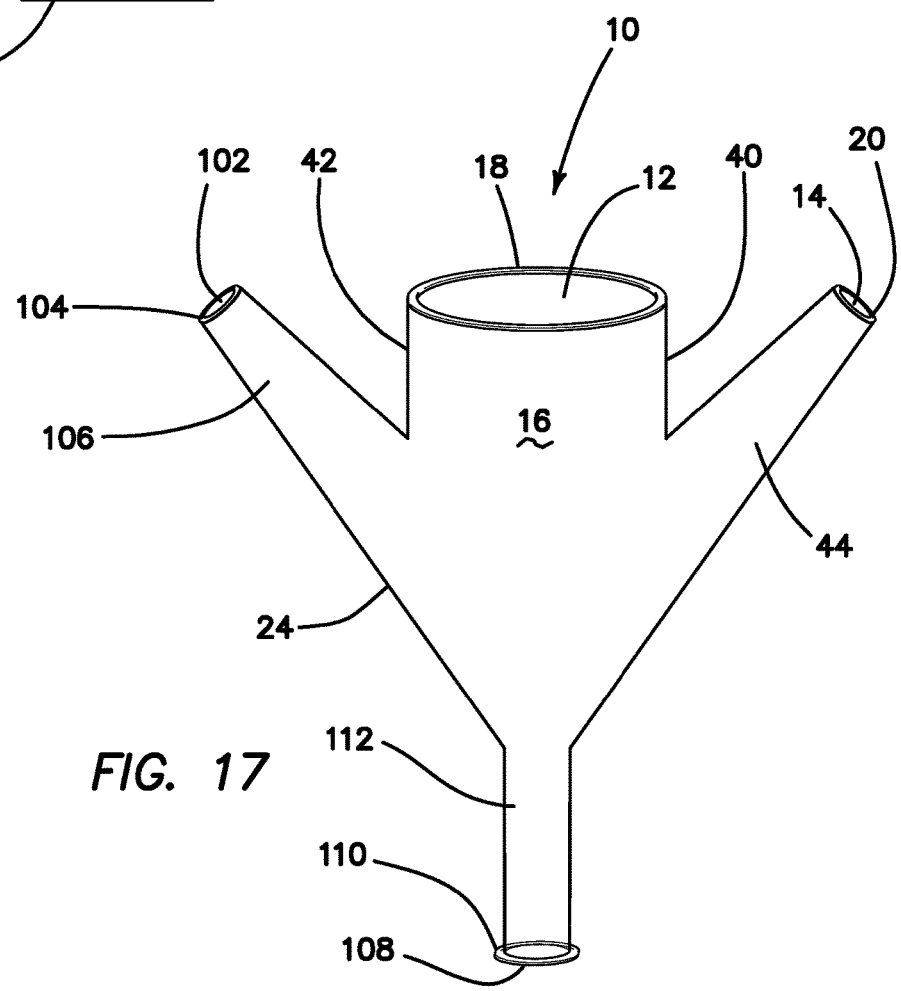
FIG. 17 is a top perspective view of a containment bag having four openings according to the present invention.

FIG. 17 illustrates yet another variation of the bag 10 further having a fourth opening 108 and a fourth ring 110 located at the fourth opening 108. The fourth opening 108 defines a fourth central longitudinal axis perpendicular to the radial plane of the ring 110 and/or opening 108. The fourth longitudinal axis may or may not be parallel to the first longitudinal axis associated with the first opening. The fourth opening 108 is substantially coaxial with the first opening 12 making the bag 10 of FIG. 17 a hybrid bag that combines the teapot-like bags of FIGS. 7A-7R and the sleeve-like bags of FIGS. 1-6, 13 and 15. The fourth opening 108 is formed in the base 24 of the bag 10 and the base 24 may form an extension neck 112 of various sizes, shapes, lengths, and positional locations with respect to the base 40 and base 24 interconnecting the first opening 12 with the fourth opening 108. In use, the bag 10 of FIG. 17 is positioned with respect to the anatomy such that the first opening 12 is at the abdomen such as inserted through an umbilical incision and resident with the first ring 18 outside the patient. The second opening 14 serves as a lateral port positioned at a lateral incision in the abdomen with the second opening 14 and second ring 20 residing outside the patient. The third opening 102 also serves as a lateral port positioned at a lateral incision in the abdomen and the fourth opening 108 is position at a lateral orifice such as the vagina.

Figure 18A:
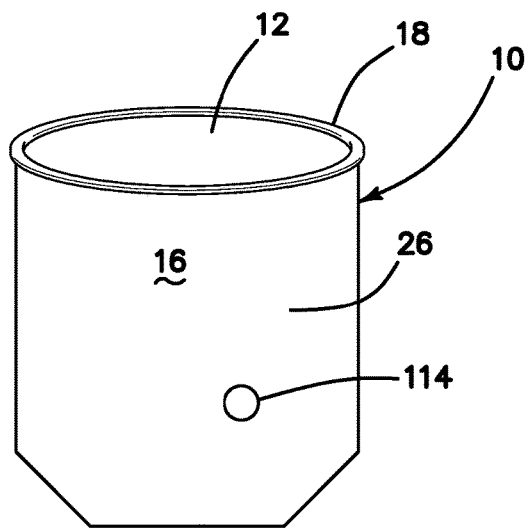
FIG. 18A is a top perspective view of a containment bag having a scope window according to the present invention.
Figure 18B:
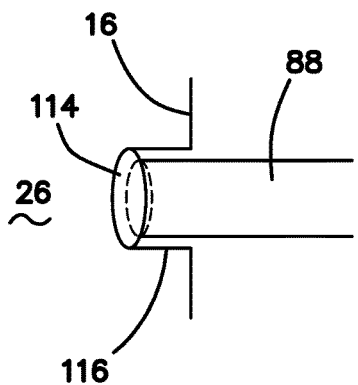
FIG. 18B is a sectional view of a scope at a scope window of a containment bag according to the present invention.

Turning now to FIGS. 18A and 18B, there is shown a containment bag 10 having at least a first opening 12 and sidewall 16 defining at least an interior first compartment 26 accessible via at least the first opening 12. A resilient first ring 18 is provided at the first opening 12. The bag 10 includes at least one window 114 of clear, transparent glass or plastic through which visualization of the contents of the compartment 26 is possible from outside the bag 10 via a scope 88. The window 114 may include a lens that provides an improved visualization when a scope 88 is placed next to the lens as shown in FIG. 18B. The window 114 and/or lens may be flush with the exterior sidewall 16 of the bag 10 or recessed at the end of an inwardly extending port 116 as shown in FIG. 18B. The port 116 is cylindrical and sized slightly larger than the distal end of the scope 88. The inwardly extending port 116 provides a closer visualization of the bag contents and also provides a resting ledge for the scope 88.

Figure 19A:
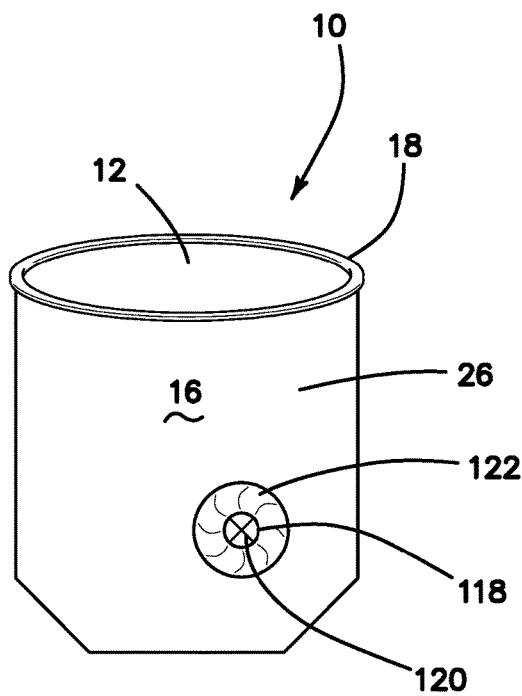
FIG. 19A is a top perspective view of a containment bag with a sealed port according to the present invention.
Figure 19B:
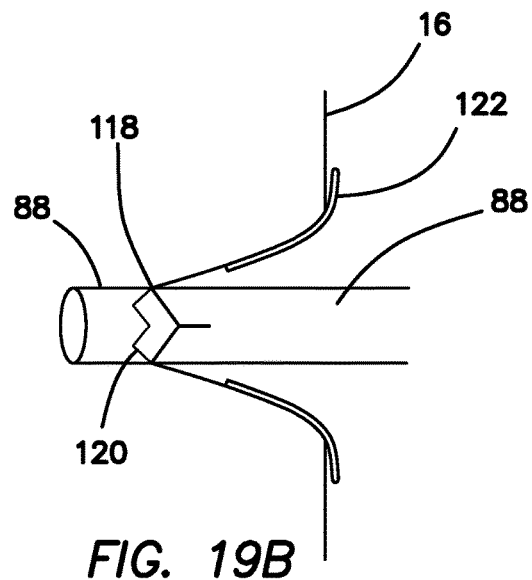
FIG. 19B is a sectional view of a scope inserted past a sealed port of a containment bag according to the present invention.

Turning now to FIGS. 19A and 19B, there is shown a containment bag 10 having at least a first opening 12 and sidewall 16 defining at least an interior first compartment 26 accessible via at least the first opening 12. A resilient first ring 18 is provided at the first opening 12. The bag 10 includes at least one port 118 in the sidewall 16 providing access to the interior compartment 26. The port 118 is fitted with at least one seal 120. More than one seal can also be provided in a seal assembly fitted and connected to the port 118. The seal assembly may include a zero seal that prevents escape of gas and fluid across the seal when no instrument is inserted through the zero seal. The zero seal may be a double duckbill type valve or other valve. The seal assembly may further include an instrument seal that seals against an inserted instrument to prevent escape of fluid and gas across the seal. Also, a seal shield may be provided to protect the seal from impingement with an instrument. Surrounding the seal 120 and port 118 may be a circumferential reinforcement 122 of plastic having a disk-like or funnel-like shape. The reinforcement 122 is made of stiffer plastic relative to the sidewall 16 of the bag 10. The reinforcement 122 provides a smooth funnel shaped entry to guide an instrument in through the seal 120 and port 118. Also, the reinforcement 122 provides a platform for connecting the seal 120 or seal assembly to the bag 10. As shown in FIG. 19B, an instrument, such as a scope 88, is inserted in through the port 118 to perform surgical procedures inside the bag 10 or to observe a specimen undergoing morcellation inside the bag. The seal 120 on the bag 10 will maintain any pressure differential across the bag 10 sidewall if, for example, the abdomen and/or bag 10 are insufflated.

Turning now to FIGS. 27-29, there is shown a containment bag 10 according to the present invention with different means for retaining the neck extension 44 in a retracted configuration to facilitate insertion of the bag 10 into the abdominal cavity. In FIG. 27, a perforation 126 is provided in the sidewall 16 at a location between the neck extension 44 and a first side of the bag 10. The perforation 126 extends downwardly such that the first opening 12 of the bag 10 remains interconnected to the second opening 14. The perforation 126 is configured such that integrity of the bag is not compromised by providing a reinforcement that prevents further perforation. The bag 10 is delivered into the abdominal cavity and then the perforation 126 is perforated inside the abdominal cavity with a surgical instrument or by pulling a tab/tether 38 at the second opening or a tab/tether located along the perforation 126. Following the perforation, the neck extension 44 is positioned in the anatomy. In another variation shown in FIG. 28, a clip 128 is used to hold the neck extension 44 close to the first side 40 of the bag 10 to facilitate insertion into the abdominal cavity. Once inside the patient, the clip 128 is removed and the neck extension 44 is placed in the anatomy. In another variation shown in FIG. 29, adhesive 130 such as an adhesive strip is used to hold the neck extension 44 close to the first side 40 of the bag 10 during deployment. The neck extension 44 may be pulled to release the adhesive from the neck extension 44 so that it may be placed in the anatomy.

Figure 30:
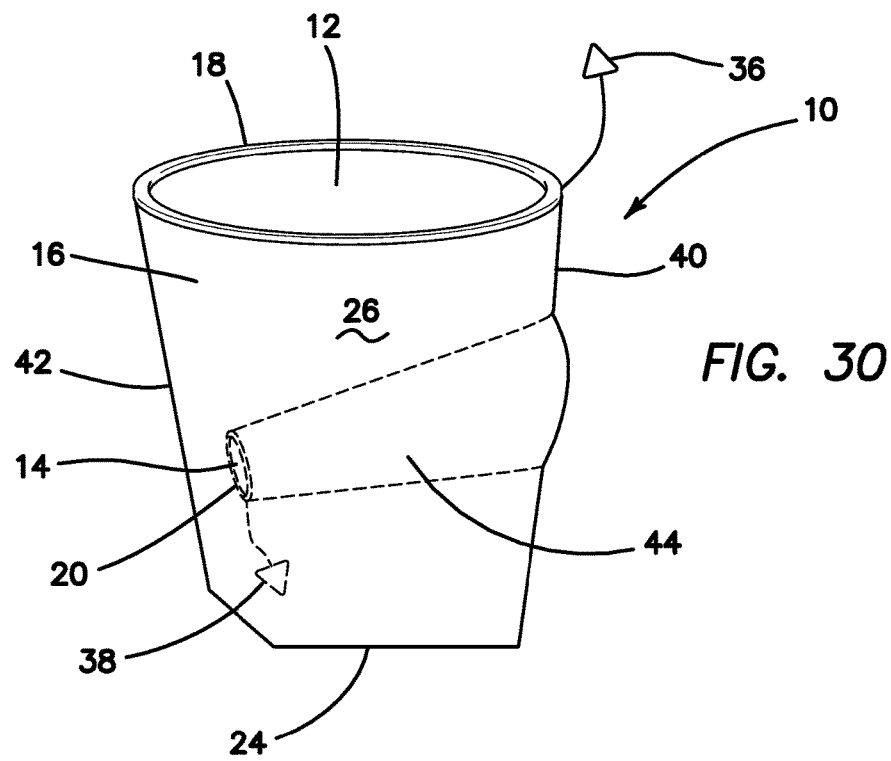
FIG. 30 is a top perspective view of a containment bag with inverted neck extension according to the present invention.
Figure 31:
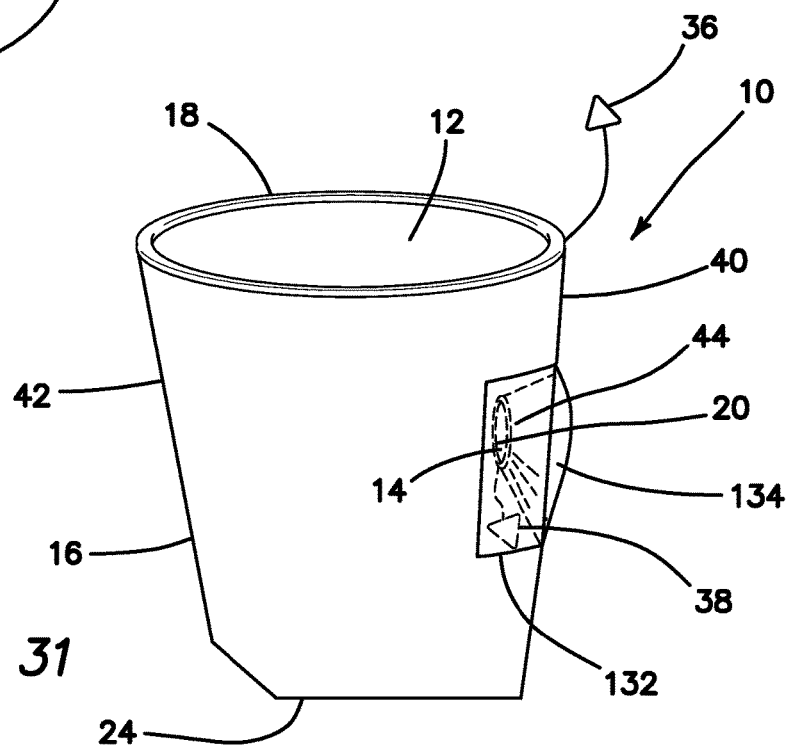
FIG. 31 is a top perspective view of a containment bag with an external pocket for a neck extension according to the present invention.

Turning now to FIG. 30, there is shown a bag 10 according to the present invention in which the neck extension 44 is inverted into the interior or first compartment 26 of the bag 10 to facilitate delivery of the bag 10 into the abdominal cavity. The bag 10 includes an undeployed configuration in which the neck extension 44 is inverted into itself and placed into the interior of the bag such that the neck extension 44 does not protrude from the first side 40. The tab 38 may be pulled outwardly to place the bag 10 in a deployed configuration. In another variation shown in FIG. 31, a pocket 132 is provided on the outer surface of the bag sidewall 16 adjacent to the intersection with the neck extension 44. The neck extension may be folded in an accordion-like fashion and inserted into the pocket opening 134 and placed inside the pocket 132 in an undeployed configuration. While in the undeployed configuration, the bag 10 is easily delivered through an incision or orifice without the neck extension 44 becoming caught up or in the way. The tab 38 is pulled out when inside the patient to extract the neck extension 44 into a deployed configuration for placement in the anatomy.

Figure 32A:
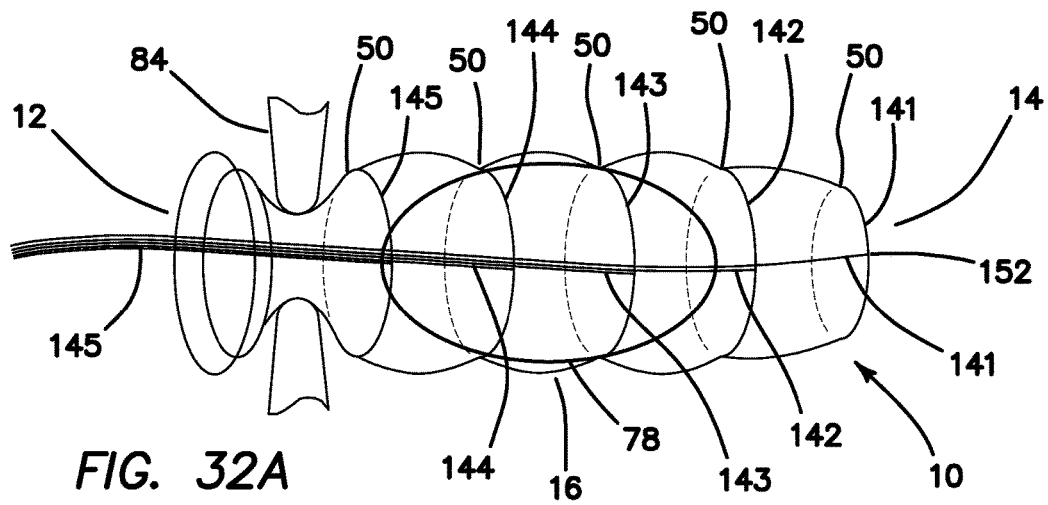
FIG. 32A is a schematic of a specimen inside a containment bag with drawstrings according to the present invention.
Figure 32B:
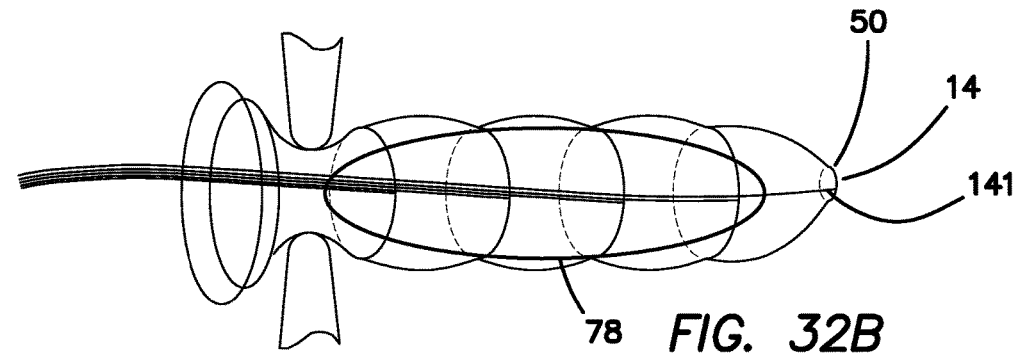
FIG. 32B is a schematic of a specimen inside a containment bag with drawstrings activated to reduce the diameter of the containment bag and specimen according to the present invention.
Figure 32C:
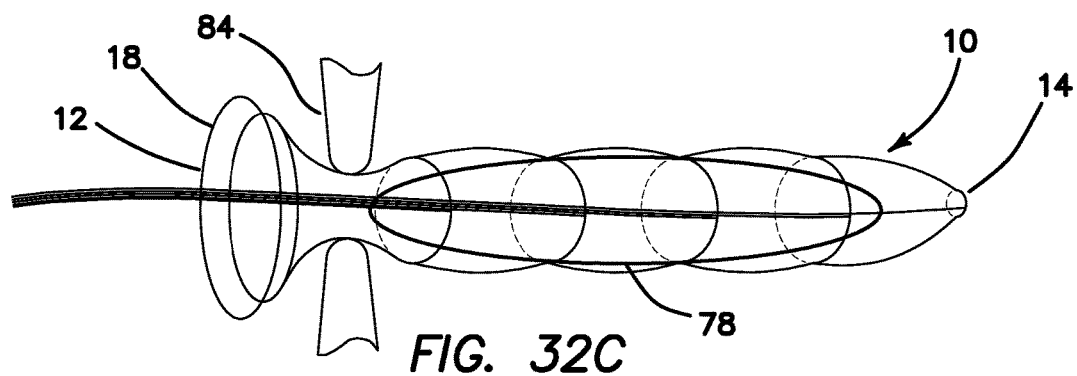
FIG. 32C is a schematic of a specimen inside a containment bag with drawstrings activated to reduce the diameter of the containment bag and specimen according to the present invention.
Figure 33A:
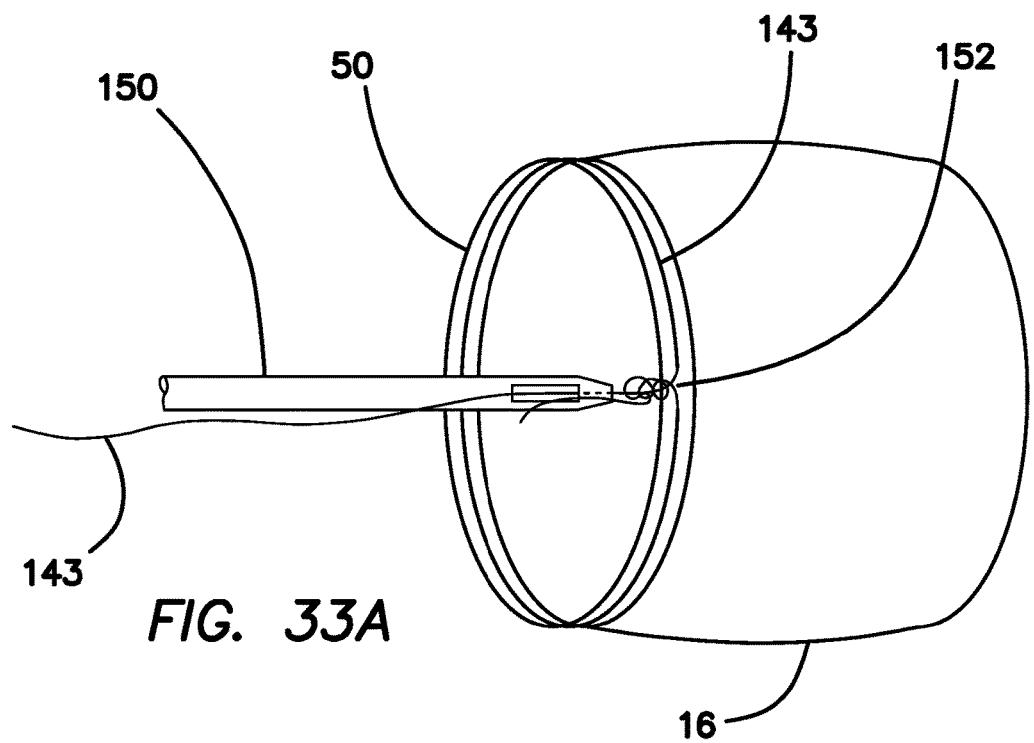
FIG. 33A is a schematic of a knot pusher and drawstring in an open configuration around the circumference of a containment bag according to the present invention.
Figure 33B:
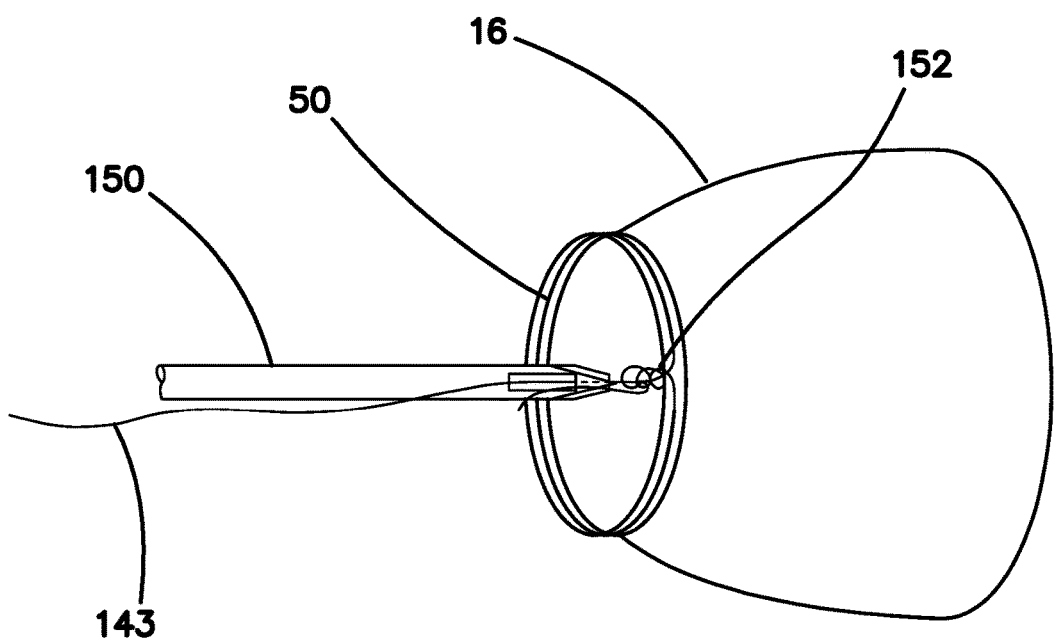
FIG. 33B is a schematic of a knot pusher and drawstring in a reduced or activated configuration around the circumference of a containment bag according to the present invention.

Turning now to FIGS. 32-33, a containment bag 10 includes a first opening 12 at a proximal end and a second opening 14 at a distal end interconnected by a sidewall 16 that is gas-tight and non-porous such as made from a flexible polymer into continuous tubular, thin-walled, elongate structure defining an interior lumen. A resilient, semi-rigid or rigid ring 18 may be provided at the first opening 12 and a resilient, semi-rigid ring 20 may be provided at the second opening 14 as described above with respect to the tubular, sleeve-like containment bags 10. The first opening 12 is sized and configured to allow insertion of surgical instruments into and through the elongate tubular body lumen. The second opening 14 is sized and configured to allow an inserted surgical instrument to pass through and distally beyond the second opening 14. The second opening 14 is additionally provided with a circumferential channel 50 having a drawstring 141 within. The circumferential drawstring 141 is sized and configured to close the second opening 14 when activated. The activation procedure comprises the placement of a "knot-pushing" device 150 proximally upon a portion of the drawstring 141 and advancing the device 150 distally to push a slip-knot 152 along the drawstring 141 until the second opening 14 is closed. A plurality of drawstring channels 50 are arranged about the entire length of the elongate tubular sidewall 16 and spaced at preferred intervals. Any number of channels 50 is within the scope of the invention to provide a substantially fixed location for at least the circumferential portion of the drawstring. Other means known to one having ordinary skill in the art for arranging the drawstring circumferential around the sidewall 16 such as belt-like loops exterior or interior to the sidewall 16 are within the scope of the present invention. A separate drawstring 141, 142, 143, 144, 145 is provided in each of the circumferential channels 50 and a portion of each drawstring extends along the longitudinal length of the bag 10 toward the proximal end. The longitudinal portion of the drawstrings may reside inside the lumen of the bag 10, outside the bag 10, or in a specialized channel, plurality of loops or a tube alongside the length of the bag 10. Each of the drawstrings also includes a slip-knot 152 preferably along a longitudinal location of the drawstring. The invention is not limited to a slip-knot 152. A compression grommet may be used to slide along the drawstring to cinch the circumferential drawstring portion. Also, a flexible plastic rack and toothed wedge may be employed. Each of the drawstrings 141, 142, 143, 144, 145 may be acted upon sequentially starting from the distal-most drawstring 141 to the proximal-most drawstring 145. Or, alternatively the drawstrings may be acted upon simultaneously or little-by-little as needed or in any order to reduce the diameter of the elongate tubular body 16 to effect reduction of the specimen 78 in the same manner as the closure of the second opening 14 with the knot pusher 150 described above. FIGS. 33A and 33B are exemplary illustrations of the activation of one drawstring 143. Only a portion of the tubular bag sidewall 16 is shown in FIGS. 33A, 33B for illustrative purposes and the same illustrations are applicable to any of the drawstrings in the bag 10. FIG. 33A shows the knot pusher 50 in a position adjacent to the slip knot 152 with the drawstring 143 extending circumferentially within a channel 50 and longitudinally along the length of the bag 10. The bag 10 has a first diameter at the drawstring 143 location inside the channel 50. FIG. 33B illustrates the knot pusher 150 advanced distally to cinch and reduce the diameter of the bag 10 to a second diameter smaller than the first diameter at the location of the drawstring 143 inside the channel 50. In one variation of the bag, the second opening 14 is absent from the bag 10 and specimen is placed into the first opening 12 and the first opening 12 and first ring 18 are pulled back up through the incision or orifice and the cinching can commence.

In use, the second opening 14 of the bag 10 is inserted into a surgical incision or natural orifice and placed within a body cavity 74. An anatomical structure 78 such as a tumor, tissue specimen, uterus or other tissue structure that has been mobilized or a surgical specimen may be drawn into the second opening 14 using an elongate surgical grasper, forceps or the like. Once the specimen 78 is within the elongate tubular body 16, the second opening 14 is closed by acting upon the drawstring 141 associated with the second opening 14. The specimen or isolated mass 78 may, in some cases, be too large, bulky or oddly shaped to be easily removed through the surgical incision or natural orifice. In this instance, a surgeon may attempt to reduce or re-shape the mass 78 so that it may be removed. There are several ways to do this. A first method may comprise the use of surgical scissors or knives to slice the mass 78 into manageable portions while within the containment bag or sleeve 10. A second method 78 is to use the drawstrings to compress the mass. A third method includes the use of a mechanical chopping or slicing device often referred to as a morcellator. Generally speaking, great care must be taken when performing these steps to avoid compromising the containment vessel or sleeve 10. The second opening 14 may be pulled through another incision or orifice to create a closed system prior to commencing morcellation.

Figure 34A:
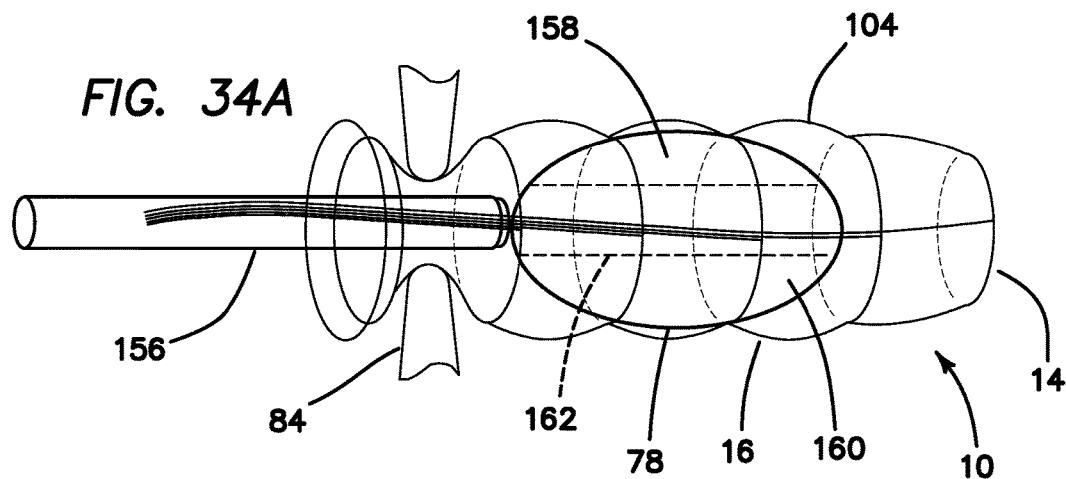
FIG. 34A is a schematic of a specimen inside a containment bag with drawstrings and a coring instrument inserted into the containment bag placed across a body wall according to the present invention.
Figure 34B:
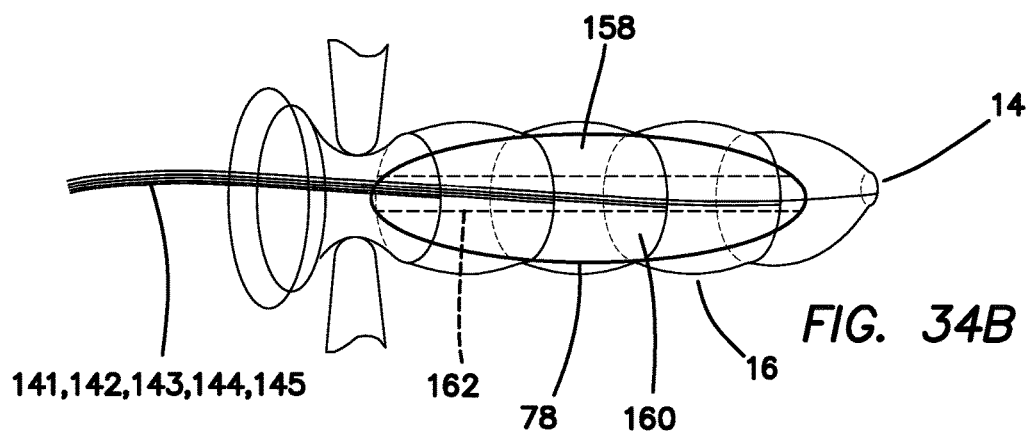
FIG. 34B is a schematic of a specimen inside a containment bag with drawstrings in a reduced or activated configuration according to the present invention.
Figure 34C:
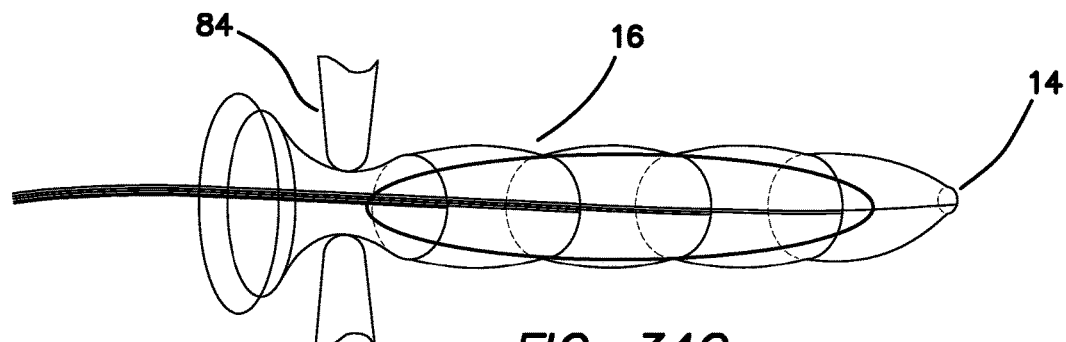
FIG. 34C is a schematic of a specimen inside a containment bag with drawstrings in a reduced or activated configuration according to the present invention.

With reference now to FIGS. 34-36, methods of using the containment bag having multiple drawstrings, cinches, or belts will be described. These methods minimize the potential for contacting the sidewall 16 of the bag 10 with a mechanical cutting element. Firstly, the subject mass 78 is drawn into the containment vessel 10 either through the second opening 14, if one is provided, or otherwise, through the first opening 12. Secondly, the distal second opening 14 of the bag 10, if one is provided, is closed in the manner described above using a knot pusher 150 to push a knot 152 and cinch the diameter with the circumferential portion of the drawstring 141. Thirdly, as shown in FIG. 34A, a cutting or "coring" instrument 156 is inserted into the first opening 12 and used to cut or "core" through the mass 78 one or more times while avoiding the margins 158, 160 of the mass 78 that may be in contact with the sidewall 16 of the bag 10. Fourthly, the cutting or "coring" device 156 may be removed from the vessel bag 10 as shown in FIG. 34B leaving an elongate empty core 162 reflected by the dotted lines in FIG. 34B. Fifthly, the plurality of drawstrings 141, 142, 143, 144, 145 may be acted upon individually or collectively to squeeze the mass 78 within the vessel bag 10 into an elongate shape having a reduced cross-sectional area as a result of the closing of the empty core with the cinching of drawstrings as shown in FIG. 34C. The reduced mass 78 is then withdrawal through the incision or orifice associated with the first opening 12 either by removing the entire bag 10 or removing the reduced mass 78 from inside the bag 10. The plurality of tightened drawstrings 141, 142, 143, 144, 145 advantageously prevents the mass 78 from shifting distally during removal of the bag 10 through an incision or orifice and creating a bolus at the distal or closed second opening 14 of the bag 10. Hence, the specimen 78 is retained with the drawstrings in a relatively fixed manner.

Figure 35A:
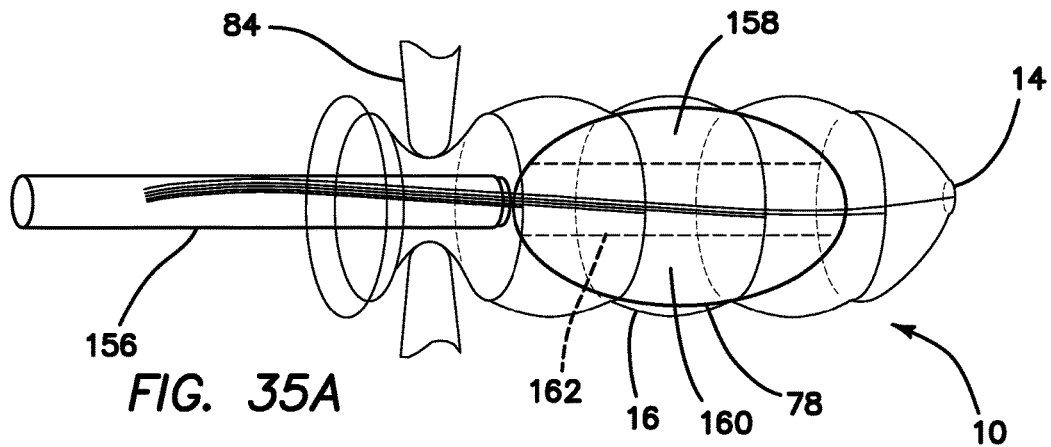
FIG. 35A is a schematic of a specimen inside a containment bag with drawstrings and a coring instrument inserted a first time into the containment bag according to the present invention.
Figure 35B:
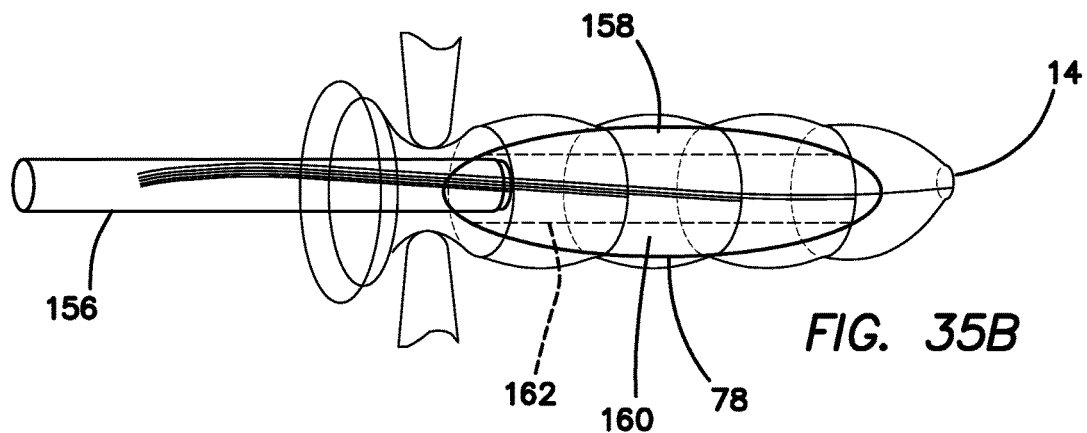
FIG. 35B is a schematic of a specimen inside a containment bag with drawstrings in a reduced or activated configuration and a coring instrument inserted a second time into the containment bag according to the present invention.
Figure 35C:
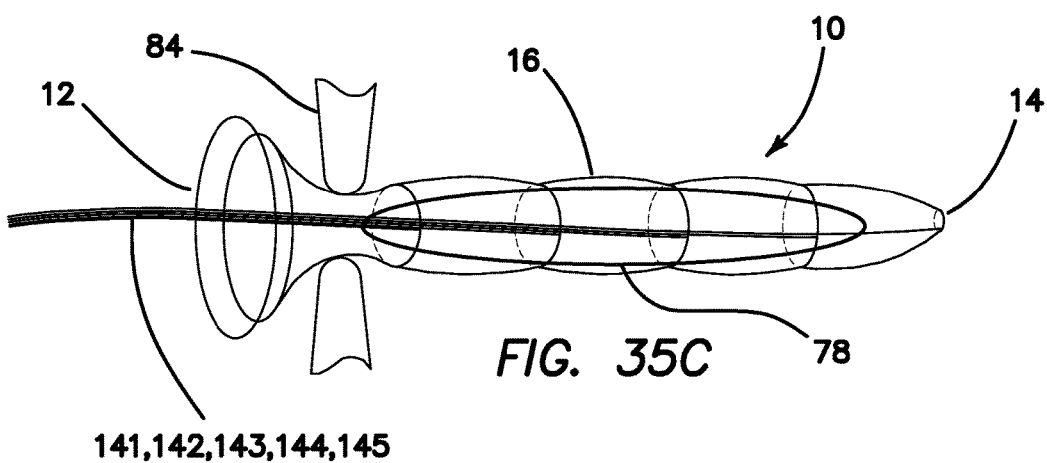
FIG. 35C is a schematic of a specimen inside a containment bag with drawstrings in a reduced or activated configuration according to the present invention.
Figure 36A:
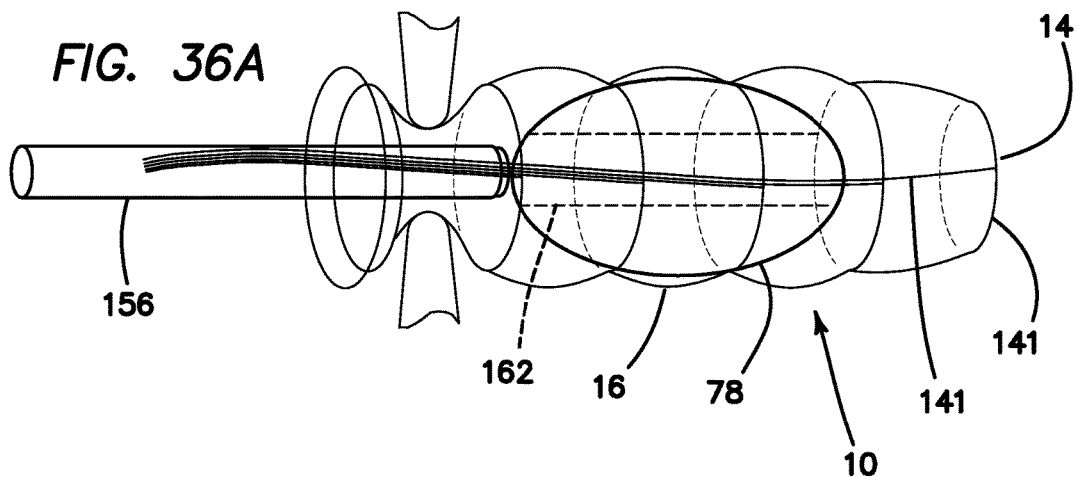
FIG. 36A is a schematic of a specimen inside a containment bag with drawstrings and a coring instrument inserted a first time into the containment bag according to the present invention.
Figure 36B:
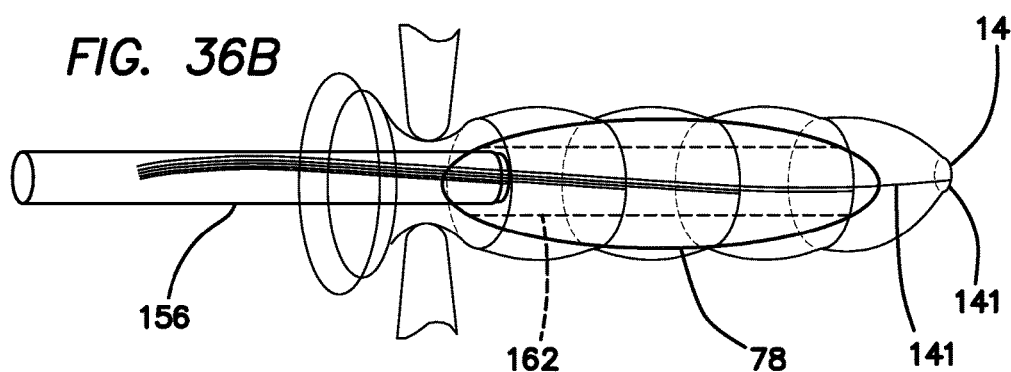
FIG. 36B is a schematic of a specimen inside a containment bag with drawstrings in a reduced or activated configuration and a coring instrument inserted a second time into the containment bag according to the present invention.
Figure 36C:
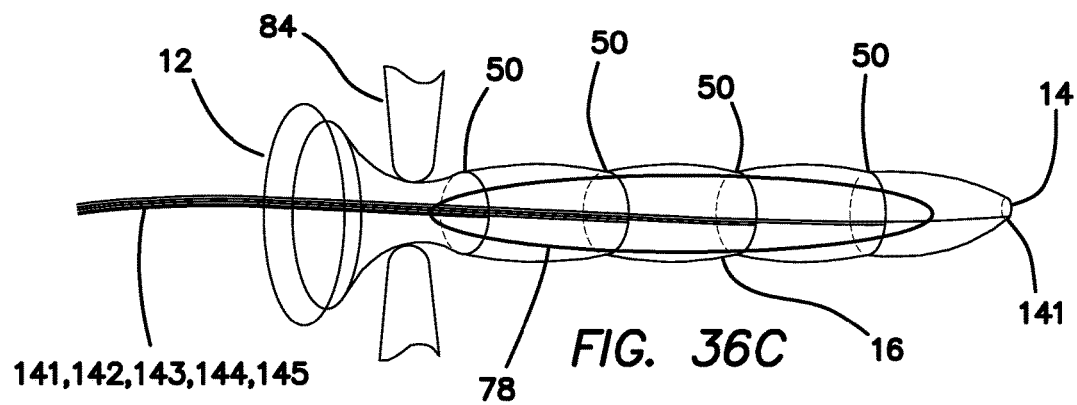
FIG. 36C is a schematic of a specimen inside a containment bag with drawstrings in a reduced or activated configuration according to the present invention.

Turning now to FIGS. 35A and 36A, a relatively large mass 78 is cored with the coring instrument 156 leaving behind an empty core 162. In FIG. 36A, the second opening 14 is shown as a variation in which the second opening 14 remains open compared to FIG. 35A such as in a benign surgical environment of if the bag 10 contained inside another bag. The drawstrings are acted to reduce the diameter of the specimen 78 by effectively squeezing closed the empty core 162 as shown in FIGS. 35B and 36B. In the instance where a contained mass 78 remains excessively large or inappropriately shaped after the drawstrings 141, 142, 143, 144, 145 have been first acted upon, the cutting or "coring" morcellator device 156 may be reinserted to further reduce the mass 78 as shown in FIGS. 35B and 36B to make a second empty core 162. The drawstrings 141, 142, 143, 144, 145 may then be further acted upon a second time and tightened again to further reduce the profile of the contained mass 78 for removal by squeezing closed the empty second core 162 as shown in FIGS. 35C and 36C. The specimen 78 is removed through the incision or orifice with the bag 10 while inside the bag 10 or the specimen is removed from the inside of the bag 10 through the first opening 12 and through the incision or orifice. In these instances, the constrictive nature of the containment bag 10 obviates the need to completely morcellate the contained mass or specimen 78 for removal or retrieval and effectively uses the margins 158, 160 of the mass as a buffer zone protecting the sidewall 16 from inadvertent contact with the coring instrument. The margins 158, 160 or portions of the mass 78 that are in contact with the sidewall 16 of the containment vessel 10 may be left, thereby, avoiding the potential for cutting, tearing or snagging the vessel sidewall 16.

Various examples of bags and devices for inserting, deploying and/or retrieving bags to be included or integrated into the morcellation system in which the entire systems, portions of the systems or combinations of the systems and/or components thereof arranged to provide a containment of object to be morcellated in accordance with various embodiments of the present invention are described in U.S. patent application Ser. No. 08/540,795, filed Oct. 11, 1995; Ser. No. 11/549,701, filed Oct. 16, 2006; Ser. No. 11/549,971, filed Oct. 16, 2006; Ser. No. 12/902,055, filed Oct. 11, 2010; and Ser. No. 13/252,110, filed Oct. 3, 2011; the entire disclosures of which are hereby incorporated by reference as if set forth in full herein. Additional bag variations are described in greater detail in U.S. Provisional Patent Application Nos. 61/970,436, 62/014,038, 62/024,698 filed on Mar. 26, 2014, Jun. 18, 2014 and Jul. 15, 2014, respectively, all of which are herein incorporated by reference in their entireties. Also, in the same capacity and incorporated by reference in their entireties are U.S. Provisional Patent Application Nos. 61/970,436, 62/014,038, 62/024,698 filed on Mar. 26, 2014, Jun. 18, 2014 and Jul. 15, 2014, respectively.

It is understood that various modifications may be made to the embodiments of the containment system disclosed herein. Therefore, the above description should not be construed as limiting, but merely as exemplifications of preferred embodiments. Those skilled in the art will envision other modifications within the scope and spirit of the present disclosure.

We claim:

1. A tissue containment bag, comprising:
   a first opening and a second opening interconnected by a sidewall of flexible material;
   the sidewall defining a first interior compartment configured for receiving a tissue specimen through the first opening into the first interior compartment;
   the sidewall forming an elongated hollow, sleeve-like neck extension defining a second interior compartment having a proximal end interconnected with the first interior compartment and a distal end interconnected with the second opening; the second opening being in fluidic communication with the second interior compartment; the second interior compartment being in fluidic communication with the first interior compartment and the first interior compartment being in fluidic communication with the first opening;
   the proximal end of the neck extension being connected to the sidewall of the first interior compartment at a first side; the neck extension extendable laterally in a direction away from the first side; and
   an external pocket provided on an outer surface of the sidewall adjacent to an entryway intersection between the first interior compartment and the second interior compartment, said external pocket is sized and configured to contain the neck extension in a folded configuration.

2. The tissue containment bag of claim 1 further including a first ring connected to the sidewall at the first opening and configured to keep the first opening in an open configuration; and a second ring connected to the neck extension at the second opening and configured to keep the second opening in an open configuration; wherein at least one of the first ring and second ring is resiliently compressible into a low profile configuration.

3. The tissue containment bag of claim 1 wherein the diameter of the neck extension is constant from the proximal end to the distal end.

4. The tissue containment bag of claim 1 further including a tether connected to the sidewall along a length of at least a portion of the neck extension.

5. The tissue containment bag of claim 1 further including a tether connected to the sidewall and extending along the neck extension from the second opening to the proximal end of the neck extension.

6. The tissue containment bag of claim 1 further including a tether connected to the sidewall extending from the second opening along a top portion of the neck extension to the proximal end of the neck extension and upwardly along a length of the sidewall to the first opening.

7. The tissue containment bag of claim 1 further including a tether connected to the sidewall along a top length of at least a portion of the neck extension.

8. The tissue containment bag of claim 1 wherein the first interior compartment comprises a base defining the first side and a second side relative to the first opening and the base; wherein the neck extension is formed at various positional locations with respect to the first side and the base.

9. The tissue containment bag of claim 8 wherein the intersection of the neck extension is contiguous with the base or is at the base.

10. The tissue containment bag of claim 1 wherein a first longitudinal axis is defined by a radial plane of the first opening when the bag is in an undeflected configuration; a second longitudinal axis being defined by a radial plane of the second opening when in the undeflected configuration; the first and second longitudinal axes being parallel or angled with respect to each other.

11. The tissue containment bag of claim 10 wherein the sidewall at the first interior compartment has a width perpendicular to the first longitudinal axis and a length along the first longitudinal axis; the neck extension having a width perpendicular to the second longitudinal axis and a length along the second longitudinal axis; the width of the neck extension being smaller than the width of the first interior compartment.

12. The tissue containment bag of claim 1 wherein the entryway intersection is defined by the proximal end of the neck extension at the first interior compartment.

13. The tissue containment bag of claim 1 further comprising a perforation located between the neck extension and the first side to retain the neck extension in a configuration for delivery; the perforation being configured to detach at least a portion of the neck extension into an extended deployed configuration.

14. The tissue containment bag of claim 1 wherein the sidewall forms an elongated hollow, sleeve-like second neck extension defining a third interior compartment having a proximal end interconnected with the first interior compartment and a distal end interconnected with a third opening; the third opening being in fluidic communication with the first interior compartment.

15. A tissue containment bag, comprising:
   a first opening and a second opening interconnected by a sidewall of flexible material;
   the sidewall defining a first interior compartment configured for receiving a tissue specimen through the first opening into the first interior compartment;
   the sidewall forming an elongated hollow, sleeve-like neck extension defining a second interior compartment having a proximal end interconnected with the first interior compartment and a distal end interconnected with the second opening; the second opening being in fluidic communication with the second interior compartment; the second interior compartment being in fluidic communication with the first interior compartment and the first interior compartment being in fluidic communication with the first opening;

the proximal end of the neck extension being connected to the sidewall of the first interior compartment at a first side; the neck extension extendable laterally in a direction away from the first side;

wherein the neck extension includes a sealing mechanism for sealing off the second opening by rolling a resilient ring connected to the sidewall at the second opening, said sealing mechanism comprises a first pocket having a first pocket mouth and a second pocket having a second pocket mouth, wherein the first and second pockets are connected to an outer surface of the neck extension such that the first pocket mouth faces the second pocket mouth.

16. The tissue containment bag of claim 15 wherein the first pocket mouth faces the proximal end of the neck extension on one side of the neck extension.

17. The tissue containment bag of claim 16 wherein the second pocket mouth faces the distal end of the neck extension on an opposite side of the neck extension; the second pocket being located distally from the first pocket; the first and second pockets being sized and configured to receive at least a portion of the distal end of the neck extension.

18. The tissue containment bag of claim 15 wherein the resilient ring is compressible into a low profile configuration.

19. The tissue containment bag of claim 15 wherein the proximal end of the neck extension at the first interior compartment defines an entryway intersection between the first interior compartment and the second interior compartment.

20. The tissue containment bag of claim 15 wherein the first interior compartment comprises a base defining the first side and a second side relative to the first opening and the base; wherein the neck extension is formed at various positional locations with respect to the first side and the base.

* * * * *